US007164002B2

(12) United States Patent
Lazarus et al.

(10) Patent No.: US 7,164,002 B2
(45) Date of Patent: Jan. 16, 2007

(54) FVIIA ANTAGONISTS

(75) Inventors: Robert A. Lazarus, Millbrae, CA (US); Henry R. Maun, San Francisco, CA (US)

(73) Assignee: Genentech, Inc., South San Francisco, CA (US)

(*) Notice: Subject to any disclaimer, the term of this patent is extended or adjusted under 35 U.S.C. 154(b) by 141 days.

(21) Appl. No.: 10/356,257

(22) Filed: Jan. 30, 2003

(65) Prior Publication Data

US 2004/0087767 A1 May 6, 2004

Related U.S. Application Data

(60) Provisional application No. 60/355,420, filed on Feb. 6, 2002.

(51) Int. Cl.
C07K 1/00 (2006.01)
C07K 14/00 (2006.01)
C07K 17/00 (2006.01)

(52) U.S. Cl. .................................... 530/350
(58) Field of Classification Search ............... 530/350
See application file for complete search history.

(56) References Cited

U.S. PATENT DOCUMENTS

| 3,972,859 A | 8/1976 | Fujino et al. |
| 4,105,603 A | 8/1978 | Vale, Jr. et al. |
| 4,399,216 A | 8/1983 | Axel et al. |
| 5,116,964 A | 5/1992 | Capon et al. |
| 5,122,614 A | 6/1992 | Zalipsky |
| 5,288,931 A | 2/1994 | Chang et al. |
| 5,336,603 A | 8/1994 | Capon et al. |
| 5,583,111 A | 12/1996 | Hemberger et al. |
| 5,714,147 A | 2/1998 | Capon et al. |
| 5,759,954 A | 6/1998 | Taguchi et al. |
| 5,834,244 A | 11/1998 | Dennis et al. |
| 5,843,739 A | 12/1998 | Slabas et al. |
| 5,863,893 A | 1/1999 | Dennis et al. |
| 5,880,256 A | 3/1999 | Dennis et al. |
| 6,087,487 A | 7/2000 | Vlasuk et al. |
| 2004/0214272 A1 | 10/2004 | La et al. |

FOREIGN PATENT DOCUMENTS

| EP | 0 307 247 | 8/1994 |
| EP | 0 278 776 | 5/1997 |
| WO | WO 89/05859 | 6/1989 |
| WO | WO 90/01940 | 3/1990 |
| WO | WO 90/03390 | 4/1990 |
| WO | WO 91/11514 | 8/1991 |
| WO | WO 95/00541 | 1/1995 |
| WO | WO 96/40779 | 12/1996 |
| WO | WO 97/20939 | 6/1997 |
| WO | WO 00/04148 | 1/2000 |
| WO | WO 01/01749 | 1/2001 |
| WO | WO 01/10892 | 2/2001 |

OTHER PUBLICATIONS

Abrahmsen, "Analysis of signals for secretion in the staphylococcal protein A" *The EMBO Journal* 4:3901-3906 (1985).
Appleyard, R.K., "Segragation of new lysogenic types during growth of a doubly lysogenic strain derived from *Escherichia coli* K12" *Genetics* 39:440-452 (1954).
Badimon et al., "Hirudin and Other Thrombin Inhibitors: Experimental Results and Potential Clinical Applications" *Trends Cardiovasc. Med.* 1(6) :261-267 (1991).
Banner et al., "The crystal structure of the complex of blood coagulation factor VIIa with soluble tissue factor" *Nature* 380:41-46 (1996).
Bone, R. C., "Modulators of Coagulation: A Critical Appraisal of Their Role In Sepsis" *Arch Intern Med* 152:1381-1389 (1992).
Carson and Brozna, "The role of tissue factor in the production of thrombin" *Blood. Coag. Fibrinol* 4:281-292 (1993).
Carter et al., "Improved Oligonucleotide Site-Directed Mutagenesis Using M13 Vectors" *Nucl. Acids Res.* 13(12):4431-4443 (Jun. 25, 1986).
Carter, "American Chemical Society Symposium Series No. 427" *Protein Purification: From Molecular Mechanisms to Large-Scale Processes.*, Ladisch et al., Eds., Chapter 13, pp. 181-193 (1990).
Castellanos-Serra ete al., "Expression and folding of an interleukin-2-proinsulin fusion protein and its conversion into insulin by a single step enzymatic removal of the C-peptide and the N-terminal fused sequence" *FEBS Letters* 378:171-176 (1996).
Clackson et al., "In vitro selection from protein and peptide libraries" *Trends Biotechnol.* 12:173-184 (1994).
Colman, R. W., "The Role of Plasma Proteases In Septic Shock" *The New England J. of Med.* 320(18):1207-1209 (1989).
Creasey et al., "Tissue Factor Pathway Inhibitor Reduces Mortality from *Escherichia coli* Septic Shock" *J. Clin. Invest.* 91:2850-2860 (1993).
Cunningham and Wells, "High-Resolution Epitope Mapping of hGH-Receptor Interactions by Alanine-Scanning Mutagenesis" *Science* 244:1081-1085 (1989).
Davie et al., "The Coagulation Cascade: Initiation, Maintenance, and Regulation" *Biochemistry* 30(43):10363-10370 (1991).
Davie, E.W., "Biochemical and Molecular Aspects of the Coagulation Cascade" *Thrombosis and Haemmostasis* 74:1-6 (1995).
Dennis et al., "Binding interactions of kistrin with platelet glycoprotein IIb-IIIa: analysis by site-directed mutagenesis" *Proteins: Structure, Function, and Genetics* 15(3):312-321 (1993).
Dennis et al., "Peptide Exosite Inhibitors of Factor VIIa as Anticoagulants." *Nature* 404:465-470 (Mar. 2000).
Dennis et al., "Selection and Characterization of a New Class of Peptide Exosite Inhibitors of Coagulation Factor VIIa." *Biochemistry* 40:9513-9521 (2001).

(Continued)

*Primary Examiner*—Karen Cochrane Carlson
*Assistant Examiner*—Agnes Rooke
(74) *Attorney, Agent, or Firm*—Merchant & Gould P.C.

(57) ABSTRACT

This invention provides novel compounds which prevent or block a FVIIa mediated or associated process or event such as the catalytic conversion of FX to FXa, FVII to FVIIa or FIX to FIXa. In particular aspects, the compounds of the invention bind Factor VIIa (FVIIa), its zymogen Factor VII (FVII). The invention also provides pharmaceutical compositions comprising the novel compounds as well as their use in diagnostic, therapeutic, and prophylactic methods.

27 Claims, 11 Drawing Sheets

OTHER PUBLICATIONS

Dickinson et al., "Influence of Cofactor Binding and Active Site Occupancy on the Conformation of the Macromolecular Substrate Exosite of Factor VIIa" *J. Mol. Biol.* 277:959-971 (1998).

Edgington, T.S. et al., "The Structural Basis of Function of the TFVIIa Complex in the Cellular Initiation of Coagulation" *Thrombosis and Haemostasis* 78:401-405 (1997).

Eigenbrot, C. et al., "The Factor VII Zymogen Structure Reveals Reregistration of B Strands during Activation" *Structure* 9:627-636 (2001).

Engels et al., "Gene Synthesis" *Agnew. Chem. Int. Ed. Engl.* 28:716-734 (1989).

Ganong, "Regulation of Gastrointestinal Function" *Review of Medical Physiology*, Lange, 13 edition, Los Altos, California, Chapter 26, pp. 411-414 (1987).

Graham et al., "Characteristics of a Human Cell Line Transformed by DNA from Human Adenovirus Type 5" *J. Gen Virol.* 36:59-72 (1977).

Greene, "Protection for the Amino Group" *Protective Groups in Organic Synthesis*, 2nd edition, New York:John Wiley & sons pp. 309-405 (1991).

Harris, J.L., "Definition and Redesign of the Extended Substrate Specificity of Granzyme B" *Journal of Biological Chemistry* 273:27364-27373 (1998).

Haskel et al., "Prevention of Arterial Reocclusion After Thrombolysis With Recombinant Lipoprotein-Associated Coagulation Inhibitor" *Circulation* 84(2);821-827 (1991).

Holst et al., "Antithrombotic Properties of a Truncated Recombinant Tissue Factor Pathway Inhibitor in an Experimental Venous Thrombosis Model" *Haemostasis* 23 (Suppl. 1):112-117 (1993).

Houghten., "General Method for the Rapid Solid-Phase Synthesis of Large Numbers of Peptides: Specificity of Antigen-Antibody Interaction at the Level of Individual Amino Acids." *Proc. Natl. Acad. Sci. USA* 82:5131-5135 (Aug. 1985).

Hsiao et al., "High-frequency transformation of yeast by plasmids containing the cloned yeast ARG4 gene" *Proc. Natl. Acad. Sci. USA* 76:3829-3833 (1979).

Husbyn et al., "Peptides corresponding to the second epidermal growth factor-like domain of human blood coagulation factor VII: synthesis, folding and biological activity" *J. Peptide Res.* 50:475-482 (1997).

Ke, S.H., "Optimal Subsite Occupancy and Design of a Selective Inhibitor of Urokinase" *Journal of Biological Chemistry* 272:20456-20462 (1997).

Kelley et al., "A Soluble Tissue Factor Mutant Is a Selective Anticoagulant and Antithrombotic Agent" *Blood* 89(9):3219-3227 (1997).

Kelley, R.F., "Folding of Eukaryotic Proteins Produced in *Escherichia Coli* " *Genetic Engineering Principles and Methods*, Setlow, J.M., New York, New York:Plenum Press vol. 12:1-19 (1990).

Kelly et al., "$Ca^{2+}$ Binding to the First Epidermal Growth Factor Module Coagulation Factor VIIa Is Important for Cofactor Interaction and Proteolytic Function" *Journal of Biological Chemistry* 272:17467-17472 (1997).

Kridel, S. J., "A Substrate Phage Enzyme-Linked Immunosorbent Assay to Profile Panels of Proteases" *Analytical Biochemistry* 294:176-184 (2001).

Kunkel et al., "Efficient site-directed mutagenesis using uracil-containing DNA" *Methods in Enzymology* 204:125-139 (1991).

Kunkel et al., "Rapid and Efficient Site-specific Mutagenesis Without Phenotypic Selection" *Methods in Enzymology* 154:367-382 (1987).

Lee et al., "Potent Bifunctional Anticoagulants: Kunitz Domain-Tissue Factor Fusion Proteins" *Biochemistry* 36(19):5607-5611 (1997).

Lehninger, A.L., "The amino acid building blocks of protein" *Biochemistry*, 2nd edition, New York, New York:Worth Publishers pp. 71-92 (1975).

Lowman and Wells, "Affinity Maturation of Human Growth Hormone by Monovalent Phage Display" *J. Mol. Biol.* 234:564-578 (1993).

Lowman, H., "Bacteriophage display and discovery of peptide leads for drug development" *Annual Review of Biophysics and Biomolecular Structure* 26:401-424 (1997).

Mann, K.G., "Biochemistry and Physiology of Blood Coagulation" *Thrombosis and Haemostasis* 82:165-174 (1999).

Mather et al., "Culture of Testicular Cells in Hormone-Supplemented Serum-Free Medium" *Annals N.Y. Acad. Sci.* 383:44-68 (1982).

Mather, J.P., "Establishment and Characterization of two Distinct Mouse Testicular Epithelial Cell Lines" *Biol. Reprod.* 23:243-252 (1980).

Matthews et al., "Substrate phage: selection of protease substrates by monovalent phage display" *Science* 260:1113-1117 (1993).

Merrifield, R.B., "Solid Phase Peptide Synthesis: The Synthesis of a Tetrapeptide" *J. Am. Chem Soc.* 85:2149-2154 (1964).

Messing et al., "A system for shotgun DNA sequencing" *Nucleic Acid Research* 9:309-321 (1981).

Neuenschwander et al., "Importance of Substrate Composition, pH and Other Variables on Tissue Factor Enhancement of Factor VIIa Activity" *Thrombosis and Haemostasis* 70:970-977 (1993).

Nilsson and Abrahmsen, "Fusions to Staphylococcal Protein A" *Meth. Enzymol.* 185:144-161 (1990).

Nilsson et al., "A synthetic IgG-binding domain based on staphylococcal protein A" *Protein Eng.* 1:107-113 (1987).

Nilsson et al., "Integrated production of human insulin and its C-peptide" *Journal of Biotechnology* 48:241-250 (1996).

O'Brien, D. et al., "Factor VIII-Bypassing Activity of Bovine Tissue Factor Using the Canine Hemophilic Model" *J. Clin. Invest.* 82:206-211 (1988).

Paborsky et al., "Lipid Association, but Not the Transmembrane Domain, Is Required for Tissue Factor activity" *Journal of Biological Chemistry* 266:21911-21916 (1991).

Pelton et al., "Design and Synthesis of Conformationally Constrained Somatostatin Analogues with High potency and Specificity for µ Opoid Receptors" *J. Med. Chem.* 29:2370-2375 (1986).

Presta et al., "Generation of a Humanized, High Affinity Anti-Tissue Factor Antibody for Use as a Novel Antithrombotic Therapeutic." *Thrombosis and Haemostasis.* 85(3):379-389 (Mar. 2001).

Rapaport and Rao, "Initiation and Regulation of Tissue Factor-Dependent Blood Coagulation" *Arterioscler. Thromb.* 12(10):1111-1121 (1992).

Rapaport and Rao, "The Tissue Factor Pathway: How It Has Become a "Prima Ballerina"" *Thrombosis and Haemostasis* 74:7-17 (1995).

Roberge, M. et al., "A Novel Exosite on Coagulation Factor VIIa and Its Molecular Interactions with a New Class of Peptide Inhibitors" *Biochemistry* 40:9522-9531 (2001).

Roberts and Vellaccio, "Unusual Amino Acids in Peptide Synthesis" *The Peptide: Analysis, Synthesis, Biology, Gross and Meiehofer*, Academic Press, Inc., New York, New York, Chapter 6, vol. 5:341-449 (1983).

Roy et al., " Self-association of Tissue Factor as Revealed by Chemical Cross-linking" *Journal of Biological Chemistry* 266:4665-4668 (1991).

Sambrook et al. *Molecular Cloning: A Laboratory Manual*, 2 edition, New York:Cold Spring Harbor Laboratory Press pp. 1.21-1.52 (1989).

Shaw et al., "A General Method for the Transfer of Cloned Genes to Plant Cells" *Gene* 23:315-330 (1983).

Smith B.J., "Enzymatic Methods for Cleaving Proteins" *Methods Mol. Biol.* 32:289-296 (1994).

Smith, G. P., "Surface presentation of protein epitopes using bacteriophage expression systems" *Curr. Opin. Biotechno.* 2(5):668-673 (1991).

Smith, M.M., "Rapid Identification of Highly Active and Selective Substrates for Stromelysin and Matrilysin Using Bacteriophage Peptide Display Libraries" *J. Bio. Chem.* 270:6440-6449 (1995).

Starovasnik et al., "Antibody variable region binding by Staphylococcal protein A: Thermodynamic analysis and location of the Fv binding site on E-domain" *Protein Sci.* 8:1423-1431 (1999).

Stewart, J.M. and Young, J.D. *Solid Phase Peptide Synthesis*, 2nd edition, Pierce Chemical Co. pp. 1-6 (1984).

Suva, L.J. et al., "A Parathyroid Hormone-Related protein Implicated in Malignant Hypercalcemia: Cloning and Expression" *Science* 237:893-896 (1987).

Urlaub et al., "Isolation of Chinese hamster cell mutants deficient in dihydrofolate reductase activity" *Proc. Natl. Acad. Sci. USA* 77:4216-4220 (1980).

Van Solingen, "Fusion of Yeast Spheroplasts" *J. Bact.* 130:946-947 (1977).

Varadarajan et al., "Cloning, expression in *Escherichia coli*, and reconstitution of human myoglobin" *Proc. Natl. Acad. Sci. USA* 82:5681-5684 (1985).

Wearley L.L., "Recent Proggress in Protein and Peptide Delivery by Noninvasive Routes" *Crot. Rev. in Ther. Drug Carrier Systems* 8:331-394 (1991).

Wells, J. et al., "Importance of Hydrogen-Bond Formation in Stabilizing the Transition State of Subtilisin" *Philos. Trans. Royal Soc. London Ser. A* 317:415-423 (1986).

Wells, J.A. et al., "Cassette Mutagenesis: An Efficient Method for Generation of Multiple Mutations at Defined Sites" *Gene* 34:315-323 (1985).

Zoller, "Oligonucleotide-directed mutagenesis using M13-derived vectors: an efficient and general procedure for the production of point mutations in any fragment of DNA" *Nucl. Acids Research* 10:6487-6500 (1982).

Capon et al., "Designing CD4 Immunoadhesins for AIDS Therapy" *Nature* 337:525-531 (1989).

Cwirla et al., "Peptides on phage" a vast library of peptides for identifying ligands *Proc. Natl. Acad. Sci. USA* 87(16):6378-6382 (1990).

Dennis and Lazarus, "Kunitz Domain Inhibitors of Tissue Factor-Factor VIIa; I. Potent Inhibitors Selected from Libraries by Phage Display" *Journal of Biological Chemistry* 269(35):22129-22136 (1994).

Dennis and Lazarus, "Kunitz Domain Inhibitors of Tissue Factor-Factor VIIa; II. Potent and Specific Inhibitors by Competitive Phage Selection" *Journal of Biological Chemistry* 269(35):22137-22144 (1994).

Hagen et al., "Characterization of a cDNA coding for human factor VII" *Proc. Natl. Acad. Sci. USA* 83:2412-2416 (1986).

Harlos et al., "Crystal structure of the extracellular region of human tissue factor" *Nature* 370:662-666 (1994).

Higashi et al., "Identification of Regions of Bovine Factor VII Essential for Binding Tissue Factor" *Journal of Biological Chemistry* 269L18891-18898 (1994).

Lowman et al., "Molecular Mimics of Insulin-Like Growth Factor I (IFG-1) for inhibiting IGF-1; IGF-Binding Protein Interactions" *Biochemistry* 37(25):8870-8878 (1998).

Lowman et al., "Selecting High-Affinity Binding Proteins by Monovalent Phage Display" *Biochemistry* 30(45):10832-10838 (1991).

Muller et al., Structure of the Extracellular Domain of Human Tissue Factor: Location of the Factor VIIa Binding Site: *Biochemistry* 33(36):10864-10870 (1994).

Oming et al., "A peptide sequence from the EBF-2 like domain of FVII inhibits TF-dependnet FX activation" *Thrombosis Research* 86(1):57-67 (1997), Scott and Smith, "Searching for peptide ligands with an epitope library" *Science* 249:386-390 (1990).

Wells and Lowaman, "Rapid evolution of peptide and protein binding properties *in vitro*" *Curr. Opin. Bioltechnol.* 3:355-362 (1992).

Wildgoose et al., "Identification of a Calcium Binding Site in the Protease Domain of Human Blood Coagulation Factor VII: Evidence for its role in Factor VII-Tissue Factor Interaction" *Biochemistry* 32:114-119 (1993).

Fig. 10

| | SEQ ID NO: |
|---|---|
| SEEWEVLCWTWEDCR | 2 |
| AEWEVLCWTWETCER | 3 |
| EAWEVLCWTWETCER | 4 |
| EEAEVLCWTWETCER | 5 |
| EEWAVLCWTWETCER | 6 |
| EEWEALCWTWETCER | 7 |
| EEWEVACWTWETCER | 8 |
| EEWEVLCATWETCER | 9 |
| EEWEVLCWAWETCER | 10 |
| EEWEVLCWTAETCER | 11 |
| EEWEVLCWTWATCER | 12 |
| EEWEVLCWTWEACER | 13 |
| EEWEVLCWTWETCAR | 14 |
| EEWEVLCWTWETCEA | 15 |
| EEWEVLCWTWETCER | 16 |
| EEWEILCWTWETCER | 17 |
| EEWEVICWTWETCER | 18 |
| EEWEVMCWTWETCER | 19 |
| EEWEVVCWTWETCER | 20 |
| EEWEVLCFTWETCER | 21 |
| EEWEVLCLTWETCER | 22 |
| EEWEVLCMTWETCER | 23 |
| EEWEVLCWTFETCER | 24 |
| EEWEVLCWTLETCER | 25 |
| EEWEVLCWTWRTCER | 26 |
| EEWEVLCWTWQTCER | 27 |
| EEWEVLCWTWETCEK | 28 |
| EEWEVLCWTWETCEL | 29 |
| EEWEVLCWTWETCEW | 30 |
| EEWEVLAWTWETAER | 31 |
| WEVLCWTWETCERGE | 32 |
| EEFEVLCWTWETCER | 33 |
| EELEVLCWTWETCER | 34 |
| FEVLCWTWETCERGE | 35 |
| FEVLCMTWETCERGE | 36 |
| EEYEVLCWTWETCER | 37 |
| EEWEVLCYTWETCER | 38 |
| EEWEVLCWTYETCER | 39 |
| EEWEVLCWTWETCEW | 30 |

SEQUENCE LISTING

<160> NUMBER OF SEQ ID NOS: 355

<210> SEQ ID NO 1
<211> LENGTH: 11
<212> TYPE: PRT
<213> ORGANISM: Artificial sequence
<220> FEATURE:
<223> OTHER INFORMATION: sequence is synthesized

<400> SEQUENCE: 1

Ser Gly Gly Gly Ser Gly Ala Ser Gly Phe Arg
 1               5                  10

<210> SEQ ID NO 2
<211> LENGTH: 15
<212> TYPE: PRT
<213> ORGANISM: Artificial sequence
<220> FEATURE:
<223> OTHER INFORMATION: sequence is synthesized

<400> SEQUENCE: 2

Ser Glu Glu Trp Glu Val Leu Cys Trp Thr Trp Glu Asp Cys Arg
 1               5                  10                  15

<210> SEQ ID NO 3
<211> LENGTH: 15
<212> TYPE: PRT
<213> ORGANISM: Artificial sequence
<220> FEATURE:
<223> OTHER INFORMATION: sequence is synthesized

<400> SEQUENCE: 3

Ala Glu Trp Glu Val Leu Cys Trp Thr Trp Glu Thr Cys Glu Arg
 1               5                  10                  15

<210> SEQ ID NO 4
<211> LENGTH: 15
<212> TYPE: PRT
<213> ORGANISM: Artificial sequence
<220> FEATURE:
<223> OTHER INFORMATION: sequence is synthesized

<400> SEQUENCE: 4

Glu Ala Trp Glu Val Leu Cys Trp Thr Trp Glu Thr Cys Glu Arg
 1               5                  10                  15

<210> SEQ ID NO 5
<211> LENGTH: 15
<212> TYPE: PRT
<213> ORGANISM: Artificial sequence
<220> FEATURE:
<223> OTHER INFORMATION: sequence is synthesized

<400> SEQUENCE: 5

Glu Glu Ala Glu Val Leu Cys Trp Thr Trp Glu Thr Cys Glu Arg
 1               5                  10                  15

<210> SEQ ID NO 6
<211> LENGTH: 15
<212> TYPE: PRT
<213> ORGANISM: Artificial sequence
<220> FEATURE:
<223> OTHER INFORMATION: sequence is synthesized

<400> SEQUENCE: 6

Glu Glu Trp Ala Val Leu Cys Trp Thr Trp Glu Thr Cys Glu Arg
1               5                   10                  15

<210> SEQ ID NO 7
<211> LENGTH: 15
<212> TYPE: PRT
<213> ORGANISM: Artificial sequence
<220> FEATURE:
<223> OTHER INFORMATION: sequence is synthesized

<400> SEQUENCE: 7

Glu Glu Trp Glu Ala Leu Cys Trp Thr Trp Glu Thr Cys Glu Arg
1               5                   10                  15

<210> SEQ ID NO 8
<211> LENGTH: 15
<212> TYPE: PRT
<213> ORGANISM: Artificial sequence
<220> FEATURE:
<223> OTHER INFORMATION: sequence is synthesized

<400> SEQUENCE: 8

Glu Glu Trp Glu Val Ala Cys Trp Thr Trp Glu Thr Cys Glu Arg
1               5                   10                  15

<210> SEQ ID NO 9
<211> LENGTH: 15
<212> TYPE: PRT
<213> ORGANISM: Artificial sequence
<220> FEATURE:
<223> OTHER INFORMATION: sequence is synthesized

<400> SEQUENCE: 9

Glu Glu Trp Glu Val Leu Cys Ala Thr Trp Glu Thr Cys Glu Arg
1               5                   10                  15

<210> SEQ ID NO 10
<211> LENGTH: 15
<212> TYPE: PRT
<213> ORGANISM: Artificial sequence
<220> FEATURE:
<223> OTHER INFORMATION: sequence is synthesized

<400> SEQUENCE: 10

Glu Glu Trp Glu Val Leu Cys Trp Ala Trp Glu Thr Cys Glu Arg
1               5                   10                  15

<210> SEQ ID NO 11
<211> LENGTH: 15
<212> TYPE: PRT
<213> ORGANISM: Artificial sequence
<220> FEATURE:
<223> OTHER INFORMATION: sequence is synthesized

<400> SEQUENCE: 11

Glu Glu Trp Glu Val Leu Cys Trp Thr Ala Glu Thr Cys Glu Arg
1               5                   10                  15

<210> SEQ ID NO 12
<211> LENGTH: 15
<212> TYPE: PRT
<213> ORGANISM: Artificial sequence
<220> FEATURE:
<223> OTHER INFORMATION: sequence is synthesized

<400> SEQUENCE: 12

Glu Glu Trp Glu Val Leu Cys Trp Thr Trp Ala Thr Cys Glu Arg

```
<210> SEQ ID NO 13
<211> LENGTH: 15
<212> TYPE: PRT
<213> ORGANISM: Artificial sequence
<220> FEATURE:
<223> OTHER INFORMATION: sequence is synthesized

<400> SEQUENCE: 13

Glu Glu Trp Glu Val Leu Cys Trp Thr Trp Glu Ala Cys Glu Arg
 1               5                  10                  15

<210> SEQ ID NO 14
<211> LENGTH: 15
<212> TYPE: PRT
<213> ORGANISM: Artificial sequence
<220> FEATURE:
<223> OTHER INFORMATION: sequence is synthesized

<400> SEQUENCE: 14

Glu Glu Trp Glu Val Leu Cys Trp Thr Trp Glu Thr Cys Ala Arg
 1               5                  10                  15

<210> SEQ ID NO 15
<211> LENGTH: 15
<212> TYPE: PRT
<213> ORGANISM: Artificial sequence
<220> FEATURE:
<223> OTHER INFORMATION: sequence is synthesized

<400> SEQUENCE: 15

Glu Glu Trp Glu Val Leu Cys Trp Thr Trp Glu Thr Cys Glu Ala
 1               5                  10                  15

<210> SEQ ID NO 16
<211> LENGTH: 15
<212> TYPE: PRT
<213> ORGANISM: Artificial sequence
<220> FEATURE:
<223> OTHER INFORMATION: sequence is synthesized

<400> SEQUENCE: 16

Glu Glu Trp Glu Val Leu Cys Trp Thr Trp Glu Thr Cys Glu Arg
 1               5                  10                  15

<210> SEQ ID NO 17
<211> LENGTH: 15
<212> TYPE: PRT
<213> ORGANISM: Artificial sequence
<220> FEATURE:
<223> OTHER INFORMATION: sequence is synthesized

<400> SEQUENCE: 17

Glu Glu Trp Glu Ile Leu Cys Trp Thr Trp Glu Thr Cys Glu Arg
 1               5                  10                  15

<210> SEQ ID NO 18
<211> LENGTH: 15
<212> TYPE: PRT
<213> ORGANISM: Artificial sequence
<220> FEATURE:
<223> OTHER INFORMATION: sequence is synthesized

<400> SEQUENCE: 18

Glu Glu Trp Glu Val Ile Cys Trp Thr Trp Glu Thr Cys Glu Arg
 1               5                  10                  15
```

```
<210> SEQ ID NO 19
<211> LENGTH: 15
<212> TYPE: PRT
<213> ORGANISM: Artificial sequence
<220> FEATURE:
<223> OTHER INFORMATION: sequence is synthesized

<400> SEQUENCE: 19

Glu Glu Trp Glu Val Met Cys Trp Thr Trp Glu Thr Cys Glu Arg
 1               5                  10                  15

<210> SEQ ID NO 20
<211> LENGTH: 15
<212> TYPE: PRT
<213> ORGANISM: Artificial sequence
<220> FEATURE:
<223> OTHER INFORMATION: sequence is synthesized

<400> SEQUENCE: 20

Glu Glu Trp Glu Val Val Cys Trp Thr Trp Glu Thr Cys Glu Arg
 1               5                  10                  15

<210> SEQ ID NO 21
<211> LENGTH: 15
<212> TYPE: PRT
<213> ORGANISM: Artificial sequence
<220> FEATURE:
<223> OTHER INFORMATION: sequence is synthesized

<400> SEQUENCE: 21

Glu Glu Trp Glu Val Leu Cys Phe Thr Trp Glu Thr Cys Glu Arg
 1               5                  10                  15

<210> SEQ ID NO 22
<211> LENGTH: 15
<212> TYPE: PRT
<213> ORGANISM: Artificial sequence
<220> FEATURE:
<223> OTHER INFORMATION: sequence is synthesized

<400> SEQUENCE: 22

Glu Glu Trp Glu Val Leu Cys Leu Thr Trp Glu Thr Cys Glu Arg
 1               5                  10                  15

<210> SEQ ID NO 23
<211> LENGTH: 15
<212> TYPE: PRT
<213> ORGANISM: Artificial sequence
<220> FEATURE:
<223> OTHER INFORMATION: sequence is synthesized

<400> SEQUENCE: 23

Glu Glu Trp Glu Val Leu Cys Met Thr Trp Glu Thr Cys Glu Arg
 1               5                  10                  15

<210> SEQ ID NO 24
<211> LENGTH: 15
<212> TYPE: PRT
<213> ORGANISM: Artificial sequence
<220> FEATURE:
<223> OTHER INFORMATION: sequence is synthesized

<400> SEQUENCE: 24

Glu Glu Trp Glu Val Leu Cys Trp Thr Phe Glu Thr Cys Glu Arg
 1               5                  10                  15
```

```
<210> SEQ ID NO 25
<211> LENGTH: 15
<212> TYPE: PRT
<213> ORGANISM: Artificial sequence
<220> FEATURE:
<223> OTHER INFORMATION: sequence is synthesized

<400> SEQUENCE: 25

Glu Glu Trp Glu Val Leu Cys Trp Thr Leu Glu Thr Cys Glu Arg
 1               5                  10                  15

<210> SEQ ID NO 26
<211> LENGTH: 15
<212> TYPE: PRT
<213> ORGANISM: Artificial sequence
<220> FEATURE:
<223> OTHER INFORMATION: sequence is synthesized

<400> SEQUENCE: 26

Glu Glu Trp Glu Val Leu Cys Trp Thr Trp Arg Thr Cys Glu Arg
 1               5                  10                  15

<210> SEQ ID NO 27
<211> LENGTH: 15
<212> TYPE: PRT
<213> ORGANISM: Artificial sequence
<220> FEATURE:
<223> OTHER INFORMATION: sequence is synthesized

<400> SEQUENCE: 27

Glu Glu Trp Glu Val Leu Cys Trp Thr Trp Gln Thr Cys Glu Arg
 1               5                  10                  15

<210> SEQ ID NO 28
<211> LENGTH: 15
<212> TYPE: PRT
<213> ORGANISM: Artificial sequence
<220> FEATURE:
<223> OTHER INFORMATION: sequence is synthesized

<400> SEQUENCE: 28

Glu Glu Trp Glu Val Leu Cys Trp Thr Trp Glu Thr Cys Glu Lys
 1               5                  10                  15

<210> SEQ ID NO 29
<211> LENGTH: 15
<212> TYPE: PRT
<213> ORGANISM: Artificial sequence
<220> FEATURE:
<223> OTHER INFORMATION: sequence is synthesized

<400> SEQUENCE: 29

Glu Glu Trp Glu Val Leu Cys Trp Thr Trp Glu Thr Cys Glu Leu
 1               5                  10                  15

<210> SEQ ID NO 30
<211> LENGTH: 15
<212> TYPE: PRT
<213> ORGANISM: Artificial sequence
<220> FEATURE:
<223> OTHER INFORMATION: sequence is synthesized

<400> SEQUENCE: 30

Glu Glu Trp Glu Val Leu Cys Trp Thr Trp Glu Thr Cys Glu Trp
 1               5                  10                  15
```

```
<210> SEQ ID NO 31
<211> LENGTH: 15
<212> TYPE: PRT
<213> ORGANISM: Artificial sequence
<220> FEATURE:
<223> OTHER INFORMATION: sequence is synthesized

<400> SEQUENCE: 31

Glu Glu Trp Glu Val Leu Ala Trp Thr Trp Glu Thr Ala Glu Arg
 1               5                  10                  15

<210> SEQ ID NO 32
<211> LENGTH: 15
<212> TYPE: PRT
<213> ORGANISM: Artificial sequence
<220> FEATURE:
<223> OTHER INFORMATION: sequence is synthesized

<400> SEQUENCE: 32

Trp Glu Val Leu Cys Trp Thr Trp Glu Thr Cys Glu Arg Gly Glu
 1               5                  10                  15

<210> SEQ ID NO 33
<211> LENGTH: 15
<212> TYPE: PRT
<213> ORGANISM: Artificial sequence
<220> FEATURE:
<223> OTHER INFORMATION: sequence is synthesized

<400> SEQUENCE: 33

Glu Glu Phe Glu Val Leu Cys Trp Thr Trp Glu Thr Cys Glu Arg
 1               5                  10                  15

<210> SEQ ID NO 34
<211> LENGTH: 15
<212> TYPE: PRT
<213> ORGANISM: Artificial sequence
<220> FEATURE:
<223> OTHER INFORMATION: sequence is synthesized

<400> SEQUENCE: 34

Glu Glu Leu Glu Val Leu Cys Trp Thr Trp Glu Thr Cys Glu Arg
 1               5                  10                  15

<210> SEQ ID NO 35
<211> LENGTH: 15
<212> TYPE: PRT
<213> ORGANISM: Artificial sequence
<220> FEATURE:
<223> OTHER INFORMATION: sequence is synthesized

<400> SEQUENCE: 35

Phe Glu Val Leu Cys Trp Thr Trp Glu Thr Cys Glu Arg Gly Glu
 1               5                  10                  15

<210> SEQ ID NO 36
<211> LENGTH: 15
<212> TYPE: PRT
<213> ORGANISM: Artificial sequence
<220> FEATURE:
<223> OTHER INFORMATION: sequence is synthesized

<400> SEQUENCE: 36

Phe Glu Val Leu Cys Met Thr Trp Glu Thr Cys Glu Arg Gly Glu
 1               5                  10                  15

<210> SEQ ID NO 37
```

```
<211> LENGTH: 15
<212> TYPE: PRT
<213> ORGANISM: Artificial sequence
<220> FEATURE:
<223> OTHER INFORMATION: sequence is synthesized

<400> SEQUENCE: 37

Glu Glu Tyr Glu Val Leu Cys Trp Thr Trp Glu Thr Cys Glu Arg
 1               5                  10                  15

<210> SEQ ID NO 38
<211> LENGTH: 15
<212> TYPE: PRT
<213> ORGANISM: Artificial sequence
<220> FEATURE:
<223> OTHER INFORMATION: sequence is synthesized

<400> SEQUENCE: 38

Glu Glu Trp Glu Val Leu Cys Tyr Thr Trp Glu Thr Cys Glu Arg
 1               5                  10                  15

<210> SEQ ID NO 39
<211> LENGTH: 15
<212> TYPE: PRT
<213> ORGANISM: Artificial sequence
<220> FEATURE:
<223> OTHER INFORMATION: sequence is synthesized

<400> SEQUENCE: 39

Glu Glu Trp Glu Val Leu Cys Trp Thr Tyr Glu Thr Cys Glu Arg
 1               5                  10                  15

<210> SEQ ID NO 40
<211> LENGTH: 13
<212> TYPE: PRT
<213> ORGANISM: Artificial sequence
<220> FEATURE:
<223> OTHER INFORMATION: sequence is synthesized

<400> SEQUENCE: 40

Trp Glu Val Leu Cys Trp Thr Trp Glu Thr Cys Glu Arg
 1               5                  10

<210> SEQ ID NO 41
<211> LENGTH: 11
<212> TYPE: PRT
<213> ORGANISM: Artificial sequence
<220> FEATURE:
<223> OTHER INFORMATION: sequence is synthesized

<400> SEQUENCE: 41

Thr Pro Thr Asp Pro Pro Thr Thr Pro Pro Thr
 1               5                  10

<210> SEQ ID NO 42
<211> LENGTH: 93
<212> TYPE: DNA
<213> ORGANISM: Artificial sequence
<220> FEATURE:
<223> OTHER INFORMATION: sequence is synthesized

<400> SEQUENCE: 42
tgctggacgt gggagacctg cgaacgtggt gaaggtcagt aataataaac      50
cccgaccgat ccgccgacca ccccgccgac cgattttgat tat             93

<210> SEQ ID NO 43
```

```
<211> LENGTH: 48
<212> TYPE: DNA
<213> ORGANISM: Artificial sequence
<220> FEATURE:
<223> OTHER INFORMATION: sequence is synthesized

<400> SEQUENCE: 43
acaaatgcct atgcacatca ccatcaccat cactccgaag agtgggag         48

<210> SEQ ID NO 44
<211> LENGTH: 78
<212> TYPE: DNA
<213> ORGANISM: Artificial sequence
<220> FEATURE:
<223> OTHER INFORMATION: sequence is synthesized
<220> FEATURE:
<221> NAME/KEY: Unsure
<222> LOCATION: 16-17, 19-20, 22-23, 25-26, 28-29, 31-32, 34-35
<223> OTHER INFORMATION: Unknown base

<400> SEQUENCE: 44
gagacctgcg aacgtnnsnn snnsnnsnns nnsnnsarma acctgacccg         50
tatcgtgggt ggtaccccga ccgatccg                                 78

<210> SEQ ID NO 45
<211> LENGTH: 75
<212> TYPE: DNA
<213> ORGANISM: Artificial sequence
<220> FEATURE:
<223> OTHER INFORMATION: sequence is synthesized
<220> FEATURE:
<221> NAME/KEY: Unsure
<222> LOCATION: 16-17, 19-20, 22-23, 25-26, 28-29, 31-32, 34-35
<223> OTHER INFORMATION: Unknown base

<400> SEQUENCE: 45
gagacctgcg aacgtnnsnn snnsnnsnns nnsnnsaamc tgacccgtat         50
cgtgggtggt accccgaccg atccg                                    75

<210> SEQ ID NO 46
<211> LENGTH: 72
<212> TYPE: DNA
<213> ORGANISM: Artificial sequence
<220> FEATURE:
<223> OTHER INFORMATION: sequence is synthesized
<220> FEATURE:
<221> NAME/KEY: Unsure
<222> LOCATION: 16-17, 19-20, 22-23, 25-26, 28-29, 31-32, 34-35
<223> OTHER INFORMATION: Unknown base

<400> SEQUENCE: 46
gagacctgcg aacgtnnsnn snnsnnsnns nnsnnscwga cccgtatcgt         50
gggtggtacc ccgaccgatc cg                                       72

<210> SEQ ID NO 47
<211> LENGTH: 78
<212> TYPE: DNA
<213> ORGANISM: Artificial sequence
<220> FEATURE:
<223> OTHER INFORMATION: sequence is synthesized
<220> FEATURE:
<221> NAME/KEY: Unsure
<222> LOCATION: 37-38, 40-41, 43-44, 46-47, 49-50, 52-53, 55-56
<223> OTHER INFORMATION: Unknown base

<400> SEQUENCE: 47
gagacctgcg aacgtggtgg tagcggtggt agcggtnnsn nsnnsnnsnn         50
```
snnsnnsggt ggtaccccga ccgatccg 78

<210> SEQ ID NO 48
<211> LENGTH: 18
<212> TYPE: PRT
<213> ORGANISM: Artificial sequence
<220> FEATURE:
<223> OTHER INFORMATION: sequence is synthesized

<400> SEQUENCE: 48

Gly Gly Gly Ser Gly Gly Ser Asn Leu Thr Arg Ile Val Gly Gly
 1               5                  10                  15

Ser Gly Gly

<210> SEQ ID NO 49
<211> LENGTH: 7
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 1, 7
<223> OTHER INFORMATION: Unknown amino acid

<400> SEQUENCE: 49

Xaa Val Glu Trp Arg Gly Xaa
 1               5

<210> SEQ ID NO 50
<211> LENGTH: 7
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 1-2
<223> OTHER INFORMATION: Unknown amino acid

<400> SEQUENCE: 50

Xaa Xaa Glu Trp Arg Gly Trp
 1               5

<210> SEQ ID NO 51
<211> LENGTH: 7
<212> TYPE: PRT
<213> ORGANISM: Artificial sequence
<220> FEATURE:
<223> OTHER INFORMATION: sequence is synthesized

<400> SEQUENCE: 51

Gly Glu Val Gly Glu Glu Glu
 1               5

<210> SEQ ID NO 52
<211> LENGTH: 12
<212> TYPE: PRT
<213> ORGANISM: Artificial sequence
<220> FEATURE:
<223> OTHER INFORMATION: sequence is synthesized

<400> SEQUENCE: 52

Gly Ser Val Phe Ala Glu Met Ser Asn Leu Thr Arg
 1               5                  10

<210> SEQ ID NO 53
<211> LENGTH: 12
<212> TYPE: PRT
<213> ORGANISM: Artificial sequence
<220> FEATURE:
<223> OTHER INFORMATION: sequence is synthesized

<400> SEQUENCE: 53

Gly Asp Asp Thr Arg Gly Ser Asn Asn Leu Thr Arg
 1               5                  10

<210> SEQ ID NO 54
<211> LENGTH: 12
<212> TYPE: PRT
<213> ORGANISM: Artificial sequence
<220> FEATURE:
<223> OTHER INFORMATION: sequence is synthesized

<400> SEQUENCE: 54

Gly Thr Asp Val Ser Ser Asp Ser Asn Leu Thr Arg
 1               5                  10

<210> SEQ ID NO 55
<211> LENGTH: 12
<212> TYPE: PRT
<213> ORGANISM: Artificial sequence
<220> FEATURE:
<223> OTHER INFORMATION: sequence is synthesized

<400> SEQUENCE: 55

Gly Asp Val Ser Asp Arg Met Ser Asn Leu Thr Arg
 1               5                  10

<210> SEQ ID NO 56
<211> LENGTH: 12
<212> TYPE: PRT
<213> ORGANISM: Artificial sequence
<220> FEATURE:
<223> OTHER INFORMATION: sequence is synthesized

<400> SEQUENCE: 56

Gly Leu Val Pro Ser Ala Ala Ser Asn Leu Thr Arg
 1               5                  10

<210> SEQ ID NO 57
<211> LENGTH: 12
<212> TYPE: PRT
<213> ORGANISM: Artificial sequence
<220> FEATURE:
<223> OTHER INFORMATION: sequence is synthesized

<400> SEQUENCE: 57

Glu Gly Gly Glu Glu Ser Phe Lys Asn Leu Thr Arg
 1               5                  10

<210> SEQ ID NO 58
<211> LENGTH: 12
<212> TYPE: PRT
<213> ORGANISM: Artificial sequence
<220> FEATURE:
<223> OTHER INFORMATION: sequence is synthesized

<400> SEQUENCE: 58

Gly Tyr Tyr Thr Asp Arg Leu Ser Asn Leu Thr Arg
 1               5                  10

<210> SEQ ID NO 59

```
<211> LENGTH: 12
<212> TYPE: PRT
<213> ORGANISM: Artificial sequence
<220> FEATURE:
<223> OTHER INFORMATION: sequence is synthesized

<400> SEQUENCE: 59

Gly Val Asp Pro Val Ser Thr Ser Asn Leu Thr Arg
 1               5                  10

<210> SEQ ID NO 60
<211> LENGTH: 12
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 5-6
<223> OTHER INFORMATION: Unknown amino acid

<400> SEQUENCE: 60

Gly Leu Pro Gly Xaa Xaa Val Arg Asn Leu Thr Val
 1               5                  10

<210> SEQ ID NO 61
<211> LENGTH: 12
<212> TYPE: PRT
<213> ORGANISM: Artificial sequence
<220> FEATURE:
<223> OTHER INFORMATION: sequence is synthesized

<400> SEQUENCE: 61

Val Val Gly Gln Asp Gly Glu Asn Asn Leu Thr Arg
 1               5                  10

<210> SEQ ID NO 62
<211> LENGTH: 12
<212> TYPE: PRT
<213> ORGANISM: Artificial sequence
<220> FEATURE:
<223> OTHER INFORMATION: sequence is synthesized

<400> SEQUENCE: 62

Gly Glu Pro Leu Ser Phe Glu Ser Asn Leu Thr Arg
 1               5                  10

<210> SEQ ID NO 63
<211> LENGTH: 12
<212> TYPE: PRT
<213> ORGANISM: Artificial sequence
<220> FEATURE:
<223> OTHER INFORMATION: sequence is synthesized

<400> SEQUENCE: 63

Gly Trp Gly Val Ala Val Glu Asn Asn Leu Thr Arg
 1               5                  10

<210> SEQ ID NO 64
<211> LENGTH: 12
<212> TYPE: PRT
<213> ORGANISM: Artificial sequence
<220> FEATURE:
<223> OTHER INFORMATION: sequence is synthesized

<400> SEQUENCE: 64

Gly Phe Leu Val Glu Asp Glu Ser Asn Leu Thr Arg
 1               5                  10
```

<210> SEQ ID NO 65
<211> LENGTH: 12
<212> TYPE: PRT
<213> ORGANISM: Artificial sequence
<220> FEATURE:
<223> OTHER INFORMATION: sequence is synthesized

<400> SEQUENCE: 65

Gly Phe Gly Asp Ser Tyr Trp Ser Asn Leu Thr Arg
 1               5                  10

<210> SEQ ID NO 66
<211> LENGTH: 12
<212> TYPE: PRT
<213> ORGANISM: Artificial sequence
<220> FEATURE:
<223> OTHER INFORMATION: sequence is synthesized

<400> SEQUENCE: 66

Gly Asp Met Leu Leu Pro Glu Ser Asn Leu Thr Arg
 1               5                  10

<210> SEQ ID NO 67
<211> LENGTH: 12
<212> TYPE: PRT
<213> ORGANISM: Artificial sequence
<220> FEATURE:
<223> OTHER INFORMATION: sequence is synthesized

<400> SEQUENCE: 67

Gly Ala Val Ser Glu Gly Ser Ser Asn Leu Thr Arg
 1               5                  10

<210> SEQ ID NO 68
<211> LENGTH: 12
<212> TYPE: PRT
<213> ORGANISM: Artificial sequence
<220> FEATURE:
<223> OTHER INFORMATION: sequence is synthesized

<400> SEQUENCE: 68

Ser Ser Ser Leu Ser Asp Gly Ser Asn Leu Thr Arg
 1               5                  10

<210> SEQ ID NO 69
<211> LENGTH: 12
<212> TYPE: PRT
<213> ORGANISM: Artificial sequence
<220> FEATURE:
<223> OTHER INFORMATION: sequence is synthesized

<400> SEQUENCE: 69

Gly Glu Trp Asp Glu Met Asp Ser Asn Leu Thr Arg
 1               5                  10

<210> SEQ ID NO 70
<211> LENGTH: 12
<212> TYPE: PRT
<213> ORGANISM: Artificial sequence
<220> FEATURE:
<223> OTHER INFORMATION: sequence is synthesized

<400> SEQUENCE: 70

Gly Phe Leu Thr Glu Leu Asp Lys Asn Leu Thr Arg
 1               5                  10

```
<210> SEQ ID NO 71
<211> LENGTH: 12
<212> TYPE: PRT
<213> ORGANISM: Artificial sequence
<220> FEATURE:
<223> OTHER INFORMATION: sequence is synthesized

<400> SEQUENCE: 71

Gly Met Leu Gly Gly Glu Met Ser Asn Leu Thr Arg
 1               5                  10

<210> SEQ ID NO 72
<211> LENGTH: 12
<212> TYPE: PRT
<213> ORGANISM: Artificial sequence
<220> FEATURE:
<223> OTHER INFORMATION: sequence is synthesized

<400> SEQUENCE: 72

Gly Gly Gly Asp Glu Val Asn Asn Leu Thr Arg Ile
 1               5                  10

<210> SEQ ID NO 73
<211> LENGTH: 12
<212> TYPE: PRT
<213> ORGANISM: Artificial sequence
<220> FEATURE:
<223> OTHER INFORMATION: sequence is synthesized

<400> SEQUENCE: 73

Trp Tyr Pro Met Tyr Gly Gly Ser Asn Leu Thr Arg
 1               5                  10

<210> SEQ ID NO 74
<211> LENGTH: 12
<212> TYPE: PRT
<213> ORGANISM: Artificial sequence
<220> FEATURE:
<223> OTHER INFORMATION: sequence is synthesized

<400> SEQUENCE: 74

Gly Gly Pro Arg Glu Asn Gly Ser Asn Leu Thr Arg
 1               5                  10

<210> SEQ ID NO 75
<211> LENGTH: 12
<212> TYPE: PRT
<213> ORGANISM: Artificial sequence
<220> FEATURE:
<223> OTHER INFORMATION: sequence is synthesized

<400> SEQUENCE: 75

Gly Gln Phe Met Glu Gly Val Ser Asn Leu Thr Arg
 1               5                  10

<210> SEQ ID NO 76
<211> LENGTH: 12
<212> TYPE: PRT
<213> ORGANISM: Artificial sequence
<220> FEATURE:
<223> OTHER INFORMATION: sequence is synthesized

<400> SEQUENCE: 76

Gly Gly Ala Val Glu Gly Glu Asn Asn Leu Thr Arg
 1               5                  10
```

```
<210> SEQ ID NO 77
<211> LENGTH: 12
<212> TYPE: PRT
<213> ORGANISM: Artificial sequence
<220> FEATURE:
<223> OTHER INFORMATION: sequence is synthesized

<400> SEQUENCE: 77

Gly Gly Val Asp Val Gly Gly Asn Asn Leu Thr Arg
 1               5                   10

<210> SEQ ID NO 78
<211> LENGTH: 12
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 6
<223> OTHER INFORMATION: Unknown amino acid

<400> SEQUENCE: 78

Gly Ala Glu Gly Gly Xaa Glu Asn Asn Leu Thr Arg
 1               5                   10

<210> SEQ ID NO 79
<211> LENGTH: 12
<212> TYPE: PRT
<213> ORGANISM: Artificial sequence
<220> FEATURE:
<223> OTHER INFORMATION: sequence is synthesized

<400> SEQUENCE: 79

Gly Val Gln Gln Glu Ser Val Asn Asn Leu Thr Arg
 1               5                   10

<210> SEQ ID NO 80
<211> LENGTH: 12
<212> TYPE: PRT
<213> ORGANISM: Artificial sequence
<220> FEATURE:
<223> OTHER INFORMATION: sequence is synthesized

<400> SEQUENCE: 80

Gly Met Ala Pro Met Gly Asp Ser Asn Leu Thr Arg
 1               5                   10

<210> SEQ ID NO 81
<211> LENGTH: 12
<212> TYPE: PRT
<213> ORGANISM: Artificial sequence
<220> FEATURE:
<223> OTHER INFORMATION: sequence is synthesized

<400> SEQUENCE: 81

Gly Leu Val Gly Ser Glu Val Ser Asn Leu Thr Arg
 1               5                   10

<210> SEQ ID NO 82
<211> LENGTH: 12
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 12
<223> OTHER INFORMATION: Unknown amino acid
```

```
<400> SEQUENCE: 82

Ser Glu Ala Ile Leu Asn Trp Ser Asn Leu Thr Xaa
  1               5                  10

<210> SEQ ID NO 83
<211> LENGTH: 12
<212> TYPE: PRT
<213> ORGANISM: Artificial sequence
<220> FEATURE:
<223> OTHER INFORMATION: sequence is synthesized

<400> SEQUENCE: 83

Gly Trp Gly Val Gly Ala Gly Ser Asn Leu Thr Arg
  1               5                  10

<210> SEQ ID NO 84
<211> LENGTH: 12
<212> TYPE: PRT
<213> ORGANISM: Artificial sequence
<220> FEATURE:
<223> OTHER INFORMATION: sequence is synthesized

<400> SEQUENCE: 84

Gly Tyr Gly Glu Val Leu Glu Ser Asn Leu Thr Arg
  1               5                  10

<210> SEQ ID NO 85
<211> LENGTH: 12
<212> TYPE: PRT
<213> ORGANISM: Artificial sequence
<220> FEATURE:
<223> OTHER INFORMATION: sequence is synthesized

<400> SEQUENCE: 85

Asp Val Val Trp Ala Glu Ser Ser Asn Leu Thr Arg
  1               5                  10

<210> SEQ ID NO 86
<211> LENGTH: 12
<212> TYPE: PRT
<213> ORGANISM: Artificial sequence
<220> FEATURE:
<223> OTHER INFORMATION: sequence is synthesized

<400> SEQUENCE: 86

Gly Lys Ser Val Asp Met Glu Asn Asn Leu Thr Arg
  1               5                  10

<210> SEQ ID NO 87
<211> LENGTH: 12
<212> TYPE: PRT
<213> ORGANISM: Artificial sequence
<220> FEATURE:
<223> OTHER INFORMATION: sequence is synthesized

<400> SEQUENCE: 87

Gly Glu Gly Glu Gly Ile Ala Asn Asn Leu Thr Arg
  1               5                  10

<210> SEQ ID NO 88
<211> LENGTH: 12
<212> TYPE: PRT
<213> ORGANISM: Artificial sequence
<220> FEATURE:
<223> OTHER INFORMATION: sequence is synthesized
```

```
<400> SEQUENCE: 88

Gly Val Glu Val Pro Gly Ser Ser Asn Leu Thr Arg
  1               5                  10

<210> SEQ ID NO 89
<211> LENGTH: 12
<212> TYPE: PRT
<213> ORGANISM: Artificial sequence
<220> FEATURE:
<223> OTHER INFORMATION: sequence is synthesized

<400> SEQUENCE: 89

Gly Met Asp Gly Ala Ser Glu Asn Asn Leu Thr Arg
  1               5                  10

<210> SEQ ID NO 90
<211> LENGTH: 12
<212> TYPE: PRT
<213> ORGANISM: Artificial sequence
<220> FEATURE:
<223> OTHER INFORMATION: sequence is synthesized

<400> SEQUENCE: 90

Gly Ser Leu Gly Asp Pro Ile Ser Asn Leu Thr Arg
  1               5                  10

<210> SEQ ID NO 91
<211> LENGTH: 12
<212> TYPE: PRT
<213> ORGANISM: Artificial sequence
<220> FEATURE:
<223> OTHER INFORMATION: sequence is synthesized

<400> SEQUENCE: 91

Gly Pro Leu Asp Glu Thr Met Lys Asn Leu Thr Arg
  1               5                  10

<210> SEQ ID NO 92
<211> LENGTH: 12
<212> TYPE: PRT
<213> ORGANISM: Artificial sequence
<220> FEATURE:
<223> OTHER INFORMATION: sequence is synthesized

<400> SEQUENCE: 92

Thr Leu Ser Gly Glu Gly Glu Lys Asn Leu Thr Arg
  1               5                  10

<210> SEQ ID NO 93
<211> LENGTH: 12
<212> TYPE: PRT
<213> ORGANISM: Artificial sequence
<220> FEATURE:
<223> OTHER INFORMATION: sequence is synthesized

<400> SEQUENCE: 93

Gly Glu Asp Met Gly Ser Pro Ser Asn Leu Thr Arg
  1               5                  10

<210> SEQ ID NO 94
<211> LENGTH: 12
<212> TYPE: PRT
<213> ORGANISM: Artificial sequence
<220> FEATURE:
<223> OTHER INFORMATION: sequence is synthesized

<400> SEQUENCE: 94
```

Asp Val Gly Asp Glu Lys Glu Ser Asn Leu Thr Arg
1               5                   10

<210> SEQ ID NO 95
<211> LENGTH: 12
<212> TYPE: PRT
<213> ORGANISM: Artificial sequence
<220> FEATURE:
<223> OTHER INFORMATION: sequence is synthesized

<400> SEQUENCE: 95

Gly Leu Thr Asn Thr Gly Leu Ser Asn Leu Thr Arg
1               5                   10

<210> SEQ ID NO 96
<211> LENGTH: 12
<212> TYPE: PRT
<213> ORGANISM: Artificial sequence
<220> FEATURE:
<223> OTHER INFORMATION: sequence is synthesized

<400> SEQUENCE: 96

Asp Ala Tyr Asn Glu Ala Pro Ser Asn Leu Thr Arg
1               5                   10

<210> SEQ ID NO 97
<211> LENGTH: 12
<212> TYPE: PRT
<213> ORGANISM: Artificial sequence
<220> FEATURE:
<223> OTHER INFORMATION: sequence is synthesized

<400> SEQUENCE: 97

Gly Ala Val Asp Val Trp Asp Ser Asn Leu Thr Arg
1               5                   10

<210> SEQ ID NO 98
<211> LENGTH: 12
<212> TYPE: PRT
<213> ORGANISM: Artificial sequence
<220> FEATURE:
<223> OTHER INFORMATION: sequence is synthesized

<400> SEQUENCE: 98

Gly Leu Ser Val Asp Ser Gly Ser Asn Leu Thr Arg
1               5                   10

<210> SEQ ID NO 99
<211> LENGTH: 12
<212> TYPE: PRT
<213> ORGANISM: Artificial sequence
<220> FEATURE:
<223> OTHER INFORMATION: sequence is synthesized

<400> SEQUENCE: 99

Glu Trp Glu Gly Gln Ser Val Ser Asn Leu Thr Arg
1               5                   10

<210> SEQ ID NO 100
<211> LENGTH: 12
<212> TYPE: PRT
<213> ORGANISM: Artificial sequence
<220> FEATURE:
<223> OTHER INFORMATION: sequence is synthesized

<400> SEQUENCE: 100

Gly Ala Ala Gly Met Glu Gly Ser Asn Leu Thr Arg
1               5                   10

<210> SEQ ID NO 101
<211> LENGTH: 12
<212> TYPE: PRT
<213> ORGANISM: Artificial sequence
<220> FEATURE:
<223> OTHER INFORMATION: sequence is synthesized

<400> SEQUENCE: 101

Gly Val Asp Glu Trp Glu Ser Ser Asn Leu Thr Arg
1               5                   10

<210> SEQ ID NO 102
<211> LENGTH: 12
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 4, 12
<223> OTHER INFORMATION: Unknown amino acid

<400> SEQUENCE: 102

Gly Gly Val Xaa Gln Glu Gly Ser Asn Leu Thr Xaa
1               5                   10

<210> SEQ ID NO 103
<211> LENGTH: 12
<212> TYPE: PRT
<213> ORGANISM: Artificial sequence
<220> FEATURE:
<223> OTHER INFORMATION: sequence is synthesized

<400> SEQUENCE: 103

Gly Glu Trp Glu Gly Leu Glu Ser Asn Leu Thr Arg
1               5                   10

<210> SEQ ID NO 104
<211> LENGTH: 12
<212> TYPE: PRT
<213> ORGANISM: Artificial sequence
<220> FEATURE:
<223> OTHER INFORMATION: sequence is synthesized

<400> SEQUENCE: 104

Gly Trp Glu Gly Pro Glu Glu Ser Asn Leu Thr Arg
1               5                   10

<210> SEQ ID NO 105
<211> LENGTH: 12
<212> TYPE: PRT
<213> ORGANISM: Artificial sequence
<220> FEATURE:
<223> OTHER INFORMATION: sequence is synthesized

<400> SEQUENCE: 105

Gly Ser Met Met Asp Asp Ala Ser Asn Leu Thr Arg
1               5                   10

<210> SEQ ID NO 106
<211> LENGTH: 12
<212> TYPE: PRT
<213> ORGANISM: Artificial sequence
<220> FEATURE:
<223> OTHER INFORMATION: sequence is synthesized

```
<400> SEQUENCE: 106

Gly Glu Gly Leu Glu Val Ser Ser Asn Leu Thr Arg
  1               5                  10

<210> SEQ ID NO 107
<211> LENGTH: 12
<212> TYPE: PRT
<213> ORGANISM: Artificial sequence
<220> FEATURE:
<223> OTHER INFORMATION: sequence is synthesized

<400> SEQUENCE: 107

Gly Ser Asp Asp Ser Arg Gly Ser Asn Leu Thr Arg
  1               5                  10

<210> SEQ ID NO 108
<211> LENGTH: 12
<212> TYPE: PRT
<213> ORGANISM: Artificial sequence
<220> FEATURE:
<223> OTHER INFORMATION: sequence is synthesized

<400> SEQUENCE: 108

Gly Met Glu Pro Val Ala Glu Asn Asn Leu Thr Arg
  1               5                  10

<210> SEQ ID NO 109
<211> LENGTH: 12
<212> TYPE: PRT
<213> ORGANISM: Artificial sequence
<220> FEATURE:
<223> OTHER INFORMATION: sequence is synthesized

<400> SEQUENCE: 109

Tyr Ser Glu Gly Met Gly Gly Ser Asn Leu Thr Arg
  1               5                  10

<210> SEQ ID NO 110
<211> LENGTH: 12
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 3
<223> OTHER INFORMATION: Unknown amino acid

<400> SEQUENCE: 110

Gly Glu Xaa Pro His Cys Met Asn Asn Leu Thr Arg
  1               5                  10

<210> SEQ ID NO 111
<211> LENGTH: 12
<212> TYPE: PRT
<213> ORGANISM: Artificial sequence
<220> FEATURE:
<223> OTHER INFORMATION: sequence is synthesized

<400> SEQUENCE: 111

Gly Asn Val Asp Trp Gln Pro Ser Asn Leu Thr Arg
  1               5                  10

<210> SEQ ID NO 112
<211> LENGTH: 12
<212> TYPE: PRT
```

```
<213> ORGANISM: Artificial sequence
<220> FEATURE:
<223> OTHER INFORMATION: sequence is synthesized

<400> SEQUENCE: 112

Gly Glu Glu Val Thr Glu Glu Asn Asn Leu Thr Arg
 1               5                   10

<210> SEQ ID NO 113
<211> LENGTH: 12
<212> TYPE: PRT
<213> ORGANISM: Artificial sequence
<220> FEATURE:
<223> OTHER INFORMATION: sequence is synthesized

<400> SEQUENCE: 113

Asp Leu Gly Gly Val Glu Pro Arg Asn Leu Thr Arg
 1               5                   10

<210> SEQ ID NO 114
<211> LENGTH: 12
<212> TYPE: PRT
<213> ORGANISM: Artificial sequence
<220> FEATURE:
<223> OTHER INFORMATION: sequence is synthesized

<400> SEQUENCE: 114

Gly Ala Val Asn Leu Gly Asp Ser Asn Leu Thr Arg
 1               5                   10

<210> SEQ ID NO 115
<211> LENGTH: 12
<212> TYPE: PRT
<213> ORGANISM: Artificial sequence
<220> FEATURE:
<223> OTHER INFORMATION: sequence is synthesized

<400> SEQUENCE: 115

Gly Val Thr Gly Asp Thr Asp Ser Asn Leu Thr Arg
 1               5                   10

<210> SEQ ID NO 116
<211> LENGTH: 11
<212> TYPE: PRT
<213> ORGANISM: Artificial sequence
<220> FEATURE:
<223> OTHER INFORMATION: sequence is synthesized

<400> SEQUENCE: 116

Ser Gly Leu Arg Val Ser Asp Leu Ala Gly Gly
 1               5                   10

<210> SEQ ID NO 117
<211> LENGTH: 11
<212> TYPE: PRT
<213> ORGANISM: Artificial sequence
<220> FEATURE:
<223> OTHER INFORMATION: sequence is synthesized

<400> SEQUENCE: 117

Ser Gly Phe Ser Arg Arg Gly Pro Ser Gly Gly
 1               5                   10

<210> SEQ ID NO 118
<211> LENGTH: 11
<212> TYPE: PRT
<213> ORGANISM: Artificial sequence
```

```
<220> FEATURE:
<223> OTHER INFORMATION: sequence is synthesized
<220> FEATURE:
<221> NAME/KEY: Unsure
<222> LOCATION: 10
<223> OTHER INFORMATION: Unknown amino acid

<400> SEQUENCE: 118

Ser Gly Ser Ala Gly Trp Val Ser Val Xaa Arg
 1               5                  10

<210> SEQ ID NO 119
<211> LENGTH: 11
<212> TYPE: PRT
<213> ORGANISM: Artificial sequence
<220> FEATURE:
<223> OTHER INFORMATION: sequence is synthesized

<400> SEQUENCE: 119

Ser Gly Pro His Gly Ser Val Arg Leu Gly Gly
 1               5                  10

<210> SEQ ID NO 120
<211> LENGTH: 11
<212> TYPE: PRT
<213> ORGANISM: Artificial sequence
<220> FEATURE:
<223> OTHER INFORMATION: sequence is synthesized

<400> SEQUENCE: 120

Ser Gly Leu Leu Glu Val Arg Asp Leu Gly Gly
 1               5                  10

<210> SEQ ID NO 121
<211> LENGTH: 11
<212> TYPE: PRT
<213> ORGANISM: Artificial sequence
<220> FEATURE:
<223> OTHER INFORMATION: sequence is synthesized

<400> SEQUENCE: 121

Ser Gly Leu Ser Ser Val Gly Leu Leu Gly Gly
 1               5                  10

<210> SEQ ID NO 122
<211> LENGTH: 11
<212> TYPE: PRT
<213> ORGANISM: Artificial sequence
<220> FEATURE:
<223> OTHER INFORMATION: sequence is synthesized

<400> SEQUENCE: 122

Ser Gly Leu Leu Arg Gly Leu Val Glu Gly Gly
 1               5                  10

<210> SEQ ID NO 123
<211> LENGTH: 11
<212> TYPE: PRT
<213> ORGANISM: Artificial sequence
<220> FEATURE:
<223> OTHER INFORMATION: sequence is synthesized

<400> SEQUENCE: 123

Ser Gly Ala Val Val Trp Arg Gln Leu Gly Gly
 1               5                  10

<210> SEQ ID NO 124
```

```
<211> LENGTH: 11
<212> TYPE: PRT
<213> ORGANISM: Artificial sequence
<220> FEATURE:
<223> OTHER INFORMATION: sequence is synthesized

<400> SEQUENCE: 124

Ser Gly Val Ala Ala Arg Leu Lys Val Gly Gly
 1               5                  10

<210> SEQ ID NO 125
<211> LENGTH: 11
<212> TYPE: PRT
<213> ORGANISM: Artificial sequence
<220> FEATURE:
<223> OTHER INFORMATION: sequence is synthesized

<400> SEQUENCE: 125

Ser Gly Val Tyr Arg Gln Phe Gly Ser Gly Gly
 1               5                  10

<210> SEQ ID NO 126
<211> LENGTH: 11
<212> TYPE: PRT
<213> ORGANISM: Artificial sequence
<220> FEATURE:
<223> OTHER INFORMATION: sequence is synthesized

<400> SEQUENCE: 126

Ser Gly Gly Thr Glu Arg Ser Val Val Gly Gly
 1               5                  10

<210> SEQ ID NO 127
<211> LENGTH: 11
<212> TYPE: PRT
<213> ORGANISM: Artificial sequence
<220> FEATURE:
<223> OTHER INFORMATION: sequence is synthesized

<400> SEQUENCE: 127

Ser Gly Leu Ala Arg Gly Thr Val Gly Gly Gly
 1               5                  10

<210> SEQ ID NO 128
<211> LENGTH: 11
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 2, 11
<223> OTHER INFORMATION: Unknown amino acid

<400> SEQUENCE: 128

Ser Xaa Ser Val Arg Asp Val Trp Asp Gly Xaa
 1               5                  10

<210> SEQ ID NO 129
<211> LENGTH: 11
<212> TYPE: PRT
<213> ORGANISM: Artificial sequence
<220> FEATURE:
<223> OTHER INFORMATION: sequence is synthesized

<400> SEQUENCE: 129

Ser Gly Ser Met Val Trp Arg Trp Ser Gly Gly
 1               5                  10
```

```
<210> SEQ ID NO 130
<211> LENGTH: 11
<212> TYPE: PRT
<213> ORGANISM: Artificial sequence
<220> FEATURE:
<223> OTHER INFORMATION: sequence is synthesized

<400> SEQUENCE: 130

Ser Gly Asp Val Pro Asn Ala Tyr Arg Gly Gly
 1               5                  10

<210> SEQ ID NO 131
<211> LENGTH: 11
<212> TYPE: PRT
<213> ORGANISM: Artificial sequence
<220> FEATURE:
<223> OTHER INFORMATION: sequence is synthesized

<400> SEQUENCE: 131

Ser Gly Arg Leu Ile Ser Arg Gly Glu Gly Gly
 1               5                  10

<210> SEQ ID NO 132
<211> LENGTH: 11
<212> TYPE: PRT
<213> ORGANISM: Artificial sequence
<220> FEATURE:
<223> OTHER INFORMATION: sequence is synthesized

<400> SEQUENCE: 132

Ser Gly Phe Leu Glu Leu Lys Ser Trp Gly Gly
 1               5                  10

<210> SEQ ID NO 133
<211> LENGTH: 11
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 3-7, 9
<223> OTHER INFORMATION: Unknown amino acid

<400> SEQUENCE: 133

Ser Gly Xaa Xaa Xaa Xaa Xaa Phe Xaa Gly Gly
 1               5                  10

<210> SEQ ID NO 134
<211> LENGTH: 11
<212> TYPE: PRT
<213> ORGANISM: Artificial sequence
<220> FEATURE:
<223> OTHER INFORMATION: sequence is synthesized

<400> SEQUENCE: 134

Ser Gly Ser Val Lys Ala Trp Ser Pro Gly Gly
 1               5                  10

<210> SEQ ID NO 135
<211> LENGTH: 11
<212> TYPE: PRT
<213> ORGANISM: Artificial sequence
<220> FEATURE:
<223> OTHER INFORMATION: sequence is synthesized

<400> SEQUENCE: 135
```

```
Ser Gly Asp Gly Leu Val Trp Leu Arg Gly Gly
 1               5                  10

<210> SEQ ID NO 136
<211> LENGTH: 11
<212> TYPE: PRT
<213> ORGANISM: Artificial sequence
<220> FEATURE:
<223> OTHER INFORMATION: sequence is synthesized

<400> SEQUENCE: 136

Ser Gly Trp Gly Leu Arg Ser Ser Val Gly Gly
 1               5                  10

<210> SEQ ID NO 137
<211> LENGTH: 11
<212> TYPE: PRT
<213> ORGANISM: Artificial sequence
<220> FEATURE:
<223> OTHER INFORMATION: sequence is synthesized

<400> SEQUENCE: 137

Ser Gly Asp Ser Ser Arg Asn Trp Ala Gly Gly
 1               5                  10

<210> SEQ ID NO 138
<211> LENGTH: 11
<212> TYPE: PRT
<213> ORGANISM: Artificial sequence
<220> FEATURE:
<223> OTHER INFORMATION: sequence is synthesized

<400> SEQUENCE: 138

Ser Gly Ser Arg Gly Leu Glu Phe Trp Gly Gly
 1               5                  10

<210> SEQ ID NO 139
<211> LENGTH: 11
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 11
<223> OTHER INFORMATION: Unknown amino acid

<400> SEQUENCE: 139

Ser Gly Phe Arg Met Val Glu Val Gly Gly Xaa
 1               5                  10

<210> SEQ ID NO 140
<211> LENGTH: 11
<212> TYPE: PRT
<213> ORGANISM: Artificial sequence
<220> FEATURE:
<223> OTHER INFORMATION: sequence is synthesized

<400> SEQUENCE: 140

Ser Gly Met Trp Asp Arg Val Met Asp Gly Gly
 1               5                  10

<210> SEQ ID NO 141
<211> LENGTH: 11
<212> TYPE: PRT
<213> ORGANISM: Artificial sequence
<220> FEATURE:
```

<223> OTHER INFORMATION: sequence is synthesized

<400> SEQUENCE: 141

Ser Gly Phe Glu Arg Met Pro Met Gly Gly Gly
 1               5                  10

<210> SEQ ID NO 142
<211> LENGTH: 11
<212> TYPE: PRT
<213> ORGANISM: Artificial sequence
<220> FEATURE:
<223> OTHER INFORMATION: sequence is synthesized

<400> SEQUENCE: 142

Ser Gly Gly Asp Ser Thr Arg Gly Tyr Gly Gly
 1               5                  10

<210> SEQ ID NO 143
<211> LENGTH: 11
<212> TYPE: PRT
<213> ORGANISM: Artificial sequence
<220> FEATURE:
<223> OTHER INFORMATION: sequence is synthesized

<400> SEQUENCE: 143

Ser Gly Glu Val Met Trp Lys Ala Leu Gly Gly
 1               5                  10

<210> SEQ ID NO 144
<211> LENGTH: 11
<212> TYPE: PRT
<213> ORGANISM: Artificial sequence
<220> FEATURE:
<223> OTHER INFORMATION: sequence is synthesized

<400> SEQUENCE: 144

Ser Gly Phe Gln Asp Leu Arg Gly Leu Gly Gly
 1               5                  10

<210> SEQ ID NO 145
<211> LENGTH: 11
<212> TYPE: PRT
<213> ORGANISM: Artificial sequence
<220> FEATURE:
<223> OTHER INFORMATION: sequence is synthesized

<400> SEQUENCE: 145

Ser Gly Met Leu Leu Gly Asp Arg Arg Gly Gly
 1               5                  10

<210> SEQ ID NO 146
<211> LENGTH: 11
<212> TYPE: PRT
<213> ORGANISM: Artificial sequence
<220> FEATURE:
<223> OTHER INFORMATION: sequence is synthesized

<400> SEQUENCE: 146

Ser Gly Pro Asp Trp Gly Arg Val Val Gly Arg
 1               5                  10

<210> SEQ ID NO 147
<211> LENGTH: 11
<212> TYPE: PRT
<213> ORGANISM: Artificial sequence
<220> FEATURE:
<223> OTHER INFORMATION: sequence is synthesized

```
<400> SEQUENCE: 147

Ser Gly Gln Glu Leu Met Phe Glu Arg Gly Gly
 1               5                  10

<210> SEQ ID NO 148
<211> LENGTH: 11
<212> TYPE: PRT
<213> ORGANISM: Artificial sequence
<220> FEATURE:
<223> OTHER INFORMATION: sequence is synthesized

<400> SEQUENCE: 148

Ser Gly Leu Arg Val Val Glu Gln Gly Gly Gly
 1               5                  10

<210> SEQ ID NO 149
<211> LENGTH: 11
<212> TYPE: PRT
<213> ORGANISM: Artificial sequence
<220> FEATURE:
<223> OTHER INFORMATION: sequence is synthesized

<400> SEQUENCE: 149

Ser Gly Val Glu Asn Tyr Leu Ser Arg Gly Gly
 1               5                  10

<210> SEQ ID NO 150
<211> LENGTH: 11
<212> TYPE: PRT
<213> ORGANISM: Artificial sequence
<220> FEATURE:
<223> OTHER INFORMATION: sequence is synthesized

<400> SEQUENCE: 150

Ser Gly Ser Val Arg Ala Lys Glu Met Gly Gly
 1               5                  10

<210> SEQ ID NO 151
<211> LENGTH: 11
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 5-8
<223> OTHER INFORMATION: Unknown amino acid

<400> SEQUENCE: 151

Ser Gly Thr Arg Xaa Xaa Xaa Xaa Thr Gly Gly
 1               5                  10

<210> SEQ ID NO 152
<211> LENGTH: 11
<212> TYPE: PRT
<213> ORGANISM: Artificial sequence
<220> FEATURE:
<223> OTHER INFORMATION: sequence is synthesized

<400> SEQUENCE: 152

Ser Gly Ala Arg Glu Trp Arg Val Met Gly Gly
 1               5                  10

<210> SEQ ID NO 153
<211> LENGTH: 11
<212> TYPE: PRT
```

```
<213> ORGANISM: Artificial sequence
<220> FEATURE:
<223> OTHER INFORMATION: sequence is synthesized

<400> SEQUENCE: 153

Ser Gly Leu Ser Leu Arg Gly Leu Gly Gly Gly
 1               5                   10

<210> SEQ ID NO 154
<211> LENGTH: 11
<212> TYPE: PRT
<213> ORGANISM: Artificial sequence
<220> FEATURE:
<223> OTHER INFORMATION: sequence is synthesized

<400> SEQUENCE: 154

Ser Gly Trp Trp Lys Ser Ser Leu Ala Gly Gly
 1               5                   10

<210> SEQ ID NO 155
<211> LENGTH: 11
<212> TYPE: PRT
<213> ORGANISM: Artificial sequence
<220> FEATURE:
<223> OTHER INFORMATION: sequence is synthesized

<400> SEQUENCE: 155

Ser Gly Ala Glu Arg Gly Arg Ser Val Gly Gly
 1               5                   10

<210> SEQ ID NO 156
<211> LENGTH: 11
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 6
<223> OTHER INFORMATION: Unknown amino acid

<400> SEQUENCE: 156

Ser Gly Val Gly Arg Xaa Asn Arg Ser Gly Gly
 1               5                   10

<210> SEQ ID NO 157
<211> LENGTH: 11
<212> TYPE: PRT
<213> ORGANISM: Artificial sequence
<220> FEATURE:
<223> OTHER INFORMATION: sequence is synthesized

<400> SEQUENCE: 157

Ser Gly Lys Gly Val Gly Val Gly Arg Gly Gly
 1               5                   10

<210> SEQ ID NO 158
<211> LENGTH: 11
<212> TYPE: PRT
<213> ORGANISM: Artificial sequence
<220> FEATURE:
<223> OTHER INFORMATION: sequence is synthesized

<400> SEQUENCE: 158

Ser Gly Ser Ser Ser Arg Ser Ser Leu Gly Gly
 1               5                   10
```

```
<210> SEQ ID NO 159
<211> LENGTH: 11
<212> TYPE: PRT
<213> ORGANISM: Artificial sequence
<220> FEATURE:
<223> OTHER INFORMATION: sequence is synthesized

<400> SEQUENCE: 159

Ser Gly Ser Arg Ala Trp Leu Arg Gly Gly Gly
 1               5                  10

<210> SEQ ID NO 160
<211> LENGTH: 11
<212> TYPE: PRT
<213> ORGANISM: Artificial sequence
<220> FEATURE:
<223> OTHER INFORMATION: sequence is synthesized

<400> SEQUENCE: 160

Ser Gly Leu Phe Lys Val Asp Phe Val Gly Gly
 1               5                  10

<210> SEQ ID NO 161
<211> LENGTH: 11
<212> TYPE: PRT
<213> ORGANISM: Artificial sequence
<220> FEATURE:
<223> OTHER INFORMATION: sequence is synthesized

<400> SEQUENCE: 161

Ser Gly Leu Gly Ser Phe Met Val Arg Gly Gly
 1               5                  10

<210> SEQ ID NO 162
<211> LENGTH: 11
<212> TYPE: PRT
<213> ORGANISM: Artificial sequence
<220> FEATURE:
<223> OTHER INFORMATION: sequence is synthesized

<400> SEQUENCE: 162

Ser Gly Ala Ser Ala Gly Leu Leu Arg Gly Gly
 1               5                  10

<210> SEQ ID NO 163
<211> LENGTH: 11
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 11
<223> OTHER INFORMATION: Unknown amino acid

<400> SEQUENCE: 163

Ser Gly Ser Trp Trp Thr Gly Leu Tyr Gly Xaa
 1               5                  10

<210> SEQ ID NO 164
<211> LENGTH: 11
<212> TYPE: PRT
<213> ORGANISM: Artificial sequence
<220> FEATURE:
<223> OTHER INFORMATION: sequence is synthesized

<400> SEQUENCE: 164

Ser Gly Val Glu Arg Ser Val Val Ala Gly Gly
```

-continued

<210> SEQ ID NO 165
<211> LENGTH: 11
<212> TYPE: PRT
<213> ORGANISM: Artificial sequence
<220> FEATURE:
<223> OTHER INFORMATION: sequence is synthesized

<400> SEQUENCE: 165

Ser Gly Leu Gly Phe Gly Arg Met Trp Gly Gly
 1               5                  10

<210> SEQ ID NO 166
<211> LENGTH: 11
<212> TYPE: PRT
<213> ORGANISM: Artificial sequence
<220> FEATURE:
<223> OTHER INFORMATION: sequence is synthesized

<400> SEQUENCE: 166

Ser Gly Lys Ala Ser Leu Leu Arg Tyr Gly Gly
 1               5                  10

<210> SEQ ID NO 167
<211> LENGTH: 11
<212> TYPE: PRT
<213> ORGANISM: Artificial sequence
<220> FEATURE:
<223> OTHER INFORMATION: sequence is synthesized

<400> SEQUENCE: 167

Ser Gly Leu Gly Val Arg Ser Val Leu Gly Gly
 1               5                  10

<210> SEQ ID NO 168
<211> LENGTH: 11
<212> TYPE: PRT
<213> ORGANISM: Artificial sequence
<220> FEATURE:
<223> OTHER INFORMATION: sequence is synthesized

<400> SEQUENCE: 168

Ser Gly Arg Ser Leu Gly Val Ala Tyr Gly Gly
 1               5                  10

<210> SEQ ID NO 169
<211> LENGTH: 11
<212> TYPE: PRT
<213> ORGANISM: Artificial sequence
<220> FEATURE:
<223> OTHER INFORMATION: sequence is synthesized

<400> SEQUENCE: 169

Ser Gly Asp Gly Leu Gln Leu Lys Leu Gly Gly
 1               5                  10

<210> SEQ ID NO 170
<211> LENGTH: 11
<212> TYPE: PRT
<213> ORGANISM: Artificial sequence
<220> FEATURE:
<223> OTHER INFORMATION: sequence is synthesized

<400> SEQUENCE: 170

Ser Gly Glu Asn Leu Leu Arg Val Ser Gly Gly
 1               5                  10

<210> SEQ ID NO 171
<211> LENGTH: 11
<212> TYPE: PRT
<213> ORGANISM: Artificial sequence
<220> FEATURE:
<223> OTHER INFORMATION: sequence is synthesized

<400> SEQUENCE: 171

Ser Gly Gly Arg Met Ser Ser Pro Val Gly Gly
 1               5                  10

<210> SEQ ID NO 172
<211> LENGTH: 11
<212> TYPE: PRT
<213> ORGANISM: Artificial sequence
<220> FEATURE:
<223> OTHER INFORMATION: sequence is synthesized

<400> SEQUENCE: 172

Ser Gly Ser Ile Gly Arg Val Leu Met Gly Gly
 1               5                  10

<210> SEQ ID NO 173
<211> LENGTH: 11
<212> TYPE: PRT
<213> ORGANISM: Artificial sequence
<220> FEATURE:
<223> OTHER INFORMATION: sequence is synthesized

<400> SEQUENCE: 173

Ser Gly Ser Ser Gly Arg Met Arg Pro Gly Gly
 1               5                  10

<210> SEQ ID NO 174
<211> LENGTH: 11
<212> TYPE: PRT
<213> ORGANISM: Artificial sequence
<220> FEATURE:
<223> OTHER INFORMATION: sequence is synthesized

<400> SEQUENCE: 174

Ser Gly Met Arg Ser Leu Pro Ser Glu Gly Gly
 1               5                  10

<210> SEQ ID NO 175
<211> LENGTH: 11
<212> TYPE: PRT
<213> ORGANISM: Artificial sequence
<220> FEATURE:
<223> OTHER INFORMATION: sequence is synthesized

<400> SEQUENCE: 175

Ser Gly Arg Met Ser Trp Leu Lys Leu Gly Gly
 1               5                  10

<210> SEQ ID NO 176
<211> LENGTH: 11
<212> TYPE: PRT
<213> ORGANISM: Artificial sequence
<220> FEATURE:
<223> OTHER INFORMATION: sequence is synthesized

<400> SEQUENCE: 176

Ser Gly Trp Ala Leu Ser Arg Trp Trp Gly Gly
 1               5                  10

```
<210> SEQ ID NO 177
<211> LENGTH: 11
<212> TYPE: PRT
<213> ORGANISM: Artificial sequence
<220> FEATURE:
<223> OTHER INFORMATION: sequence is synthesized

<400> SEQUENCE: 177

Ser Gly Leu Ile Lys Trp Gly Ser Ser Gly Gly
 1               5                  10

<210> SEQ ID NO 178
<211> LENGTH: 11
<212> TYPE: PRT
<213> ORGANISM: Artificial sequence
<220> FEATURE:
<223> OTHER INFORMATION: sequence is synthesized

<400> SEQUENCE: 178

Ser Gly Ser Ser Glu Gln Arg Leu Leu Gly Gly
 1               5                  10

<210> SEQ ID NO 179
<211> LENGTH: 11
<212> TYPE: PRT
<213> ORGANISM: Artificial sequence
<220> FEATURE:
<223> OTHER INFORMATION: sequence is synthesized

<400> SEQUENCE: 179

Ser Gly Arg Ser Leu Leu Arg Ser Ser Gly Gly
 1               5                  10

<210> SEQ ID NO 180
<211> LENGTH: 11
<212> TYPE: PRT
<213> ORGANISM: Artificial sequence
<220> FEATURE:
<223> OTHER INFORMATION: sequence is synthesized

<400> SEQUENCE: 180

Ser Gly Gly Val Glu Ser Val Arg Leu Gly Gly
 1               5                  10

<210> SEQ ID NO 181
<211> LENGTH: 11
<212> TYPE: PRT
<213> ORGANISM: Artificial sequence
<220> FEATURE:
<223> OTHER INFORMATION: sequence is synthesized

<400> SEQUENCE: 181

Ser Gly Ala Phe Gly Trp Val Gly Ala Gly Gly
 1               5                  10

<210> SEQ ID NO 182
<211> LENGTH: 11
<212> TYPE: PRT
<213> ORGANISM: Artificial sequence
<220> FEATURE:
<223> OTHER INFORMATION: sequence is synthesized

<400> SEQUENCE: 182

Ser Gly Pro Gln Glu Leu Arg Leu Gly Gly Gly
 1               5                  10
```

```
<210> SEQ ID NO 183
<211> LENGTH: 11
<212> TYPE: PRT
<213> ORGANISM: Artificial sequence
<220> FEATURE:
<223> OTHER INFORMATION: sequence is synthesized

<400> SEQUENCE: 183

Ser Gly Leu Val Gly Glu Leu Arg Gly Gly Gly
 1               5                  10

<210> SEQ ID NO 184
<211> LENGTH: 11
<212> TYPE: PRT
<213> ORGANISM: Artificial sequence
<220> FEATURE:
<223> OTHER INFORMATION: sequence is synthesized

<400> SEQUENCE: 184

Ser Gly Met Arg Ser Leu Glu Arg Phe Gly Gly
 1               5                  10

<210> SEQ ID NO 185
<211> LENGTH: 11
<212> TYPE: PRT
<213> ORGANISM: Artificial sequence
<220> FEATURE:
<223> OTHER INFORMATION: sequence is synthesized

<400> SEQUENCE: 185

Ser Gly Arg Asn Val Thr Leu Gly Leu Gly Gly
 1               5                  10

<210> SEQ ID NO 186
<211> LENGTH: 11
<212> TYPE: PRT
<213> ORGANISM: Artificial sequence
<220> FEATURE:
<223> OTHER INFORMATION: sequence is synthesized

<400> SEQUENCE: 186

Ser Gly Ser Asn Met Trp Arg Trp Trp Gly Gly
 1               5                  10

<210> SEQ ID NO 187
<211> LENGTH: 11
<212> TYPE: PRT
<213> ORGANISM: Artificial sequence
<220> FEATURE:
<223> OTHER INFORMATION: sequence is synthesized

<400> SEQUENCE: 187

Ser Gly Gly Lys Ser Leu Trp Asp Tyr Gly Gly
 1               5                  10

<210> SEQ ID NO 188
<211> LENGTH: 11
<212> TYPE: PRT
<213> ORGANISM: Artificial sequence
<220> FEATURE:
<223> OTHER INFORMATION: sequence is synthesized

<400> SEQUENCE: 188

Ser Gly Leu Val Phe Lys Ser Leu Ser Gly Gly
 1               5                  10

<210> SEQ ID NO 189
```

```
<211> LENGTH: 11
<212> TYPE: PRT
<213> ORGANISM: Artificial sequence
<220> FEATURE:
<223> OTHER INFORMATION: sequence is synthesized

<400> SEQUENCE: 189

Ser Gly Gly Glu Gly Ser Tyr Ser Arg Gly Ala
 1               5                  10

<210> SEQ ID NO 190
<211> LENGTH: 11
<212> TYPE: PRT
<213> ORGANISM: Artificial sequence
<220> FEATURE:
<223> OTHER INFORMATION: sequence is synthesized

<400> SEQUENCE: 190

Ser Gly Ser Leu Gly Leu Pro Ser Ala Gly Gly
 1               5                  10

<210> SEQ ID NO 191
<211> LENGTH: 11
<212> TYPE: PRT
<213> ORGANISM: Artificial sequence
<220> FEATURE:
<223> OTHER INFORMATION: sequence is synthesized

<400> SEQUENCE: 191

Ser Gly Arg Leu Leu Met Gly Leu Glu Gly Gly
 1               5                  10

<210> SEQ ID NO 192
<211> LENGTH: 11
<212> TYPE: PRT
<213> ORGANISM: Artificial sequence
<220> FEATURE:
<223> OTHER INFORMATION: sequence is synthesized

<400> SEQUENCE: 192

Ser Gly His Leu Glu Val Arg Gly Pro Gly Gly
 1               5                  10

<210> SEQ ID NO 193
<211> LENGTH: 11
<212> TYPE: PRT
<213> ORGANISM: Artificial sequence
<220> FEATURE:
<223> OTHER INFORMATION: sequence is synthesized

<400> SEQUENCE: 193

Ser Gly Met Arg Phe Leu Ala Glu Val Gly Gly
 1               5                  10

<210> SEQ ID NO 194
<211> LENGTH: 11
<212> TYPE: PRT
<213> ORGANISM: Artificial sequence
<220> FEATURE:
<223> OTHER INFORMATION: sequence is synthesized

<400> SEQUENCE: 194

Ser Gly Met Ser Arg Asp Ala Trp Ala Gly Gly
 1               5                  10

<210> SEQ ID NO 195
<211> LENGTH: 11
```

```
<212> TYPE: PRT
<213> ORGANISM: Artificial sequence
<220> FEATURE:
<223> OTHER INFORMATION: sequence is synthesized

<400> SEQUENCE: 195

Ser Gly Trp Gly Met Arg Gly Trp Val Gly Gly
  1               5                  10

<210> SEQ ID NO 196
<211> LENGTH: 11
<212> TYPE: PRT
<213> ORGANISM: Artificial sequence
<220> FEATURE:
<223> OTHER INFORMATION: sequence is synthesized

<400> SEQUENCE: 196

Ser Gly Val Gln Thr Leu Arg Ser Phe Gly Gly
  1               5                  10

<210> SEQ ID NO 197
<211> LENGTH: 11
<212> TYPE: PRT
<213> ORGANISM: Artificial sequence
<220> FEATURE:
<223> OTHER INFORMATION: sequence is synthesized

<400> SEQUENCE: 197

Ser Gly Trp Glu Thr Arg Gly Val Ser Gly Gly
  1               5                  10

<210> SEQ ID NO 198
<211> LENGTH: 11
<212> TYPE: PRT
<213> ORGANISM: Artificial sequence
<220> FEATURE:
<223> OTHER INFORMATION: sequence is synthesized

<400> SEQUENCE: 198

Ser Gly Asp His Arg Leu Leu Met Leu Gly Gly
  1               5                  10

<210> SEQ ID NO 199
<211> LENGTH: 11
<212> TYPE: PRT
<213> ORGANISM: Artificial sequence
<220> FEATURE:
<223> OTHER INFORMATION: sequence is synthesized

<400> SEQUENCE: 199

Ser Gly Gly Arg Ala Leu Arg Gly Gly Gly Gly
  1               5                  10

<210> SEQ ID NO 200
<211> LENGTH: 11
<212> TYPE: PRT
<213> ORGANISM: Artificial sequence
<220> FEATURE:
<223> OTHER INFORMATION: sequence is synthesized

<400> SEQUENCE: 200

Ser Gly Ile Met Arg Glu Trp Gly Ile Gly Gly
  1               5                  10

<210> SEQ ID NO 201
<211> LENGTH: 11
<212> TYPE: PRT
```

```
<213> ORGANISM: Artificial sequence
<220> FEATURE:
<223> OTHER INFORMATION: sequence is synthesized

<400> SEQUENCE: 201

Ser Gly Leu Val Val Leu Phe Ser Arg Gly Gly
  1               5                  10

<210> SEQ ID NO 202
<211> LENGTH: 11
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 3, 3
<223> OTHER INFORMATION: Unknown amino acid

<400> SEQUENCE: 202

Ser Gly Xaa Asp Trp Val Asp Arg Gly Gly Gly
  1               5                  10

<210> SEQ ID NO 203
<211> LENGTH: 11
<212> TYPE: PRT
<213> ORGANISM: Artificial sequence
<220> FEATURE:
<223> OTHER INFORMATION: sequence is synthesized

<400> SEQUENCE: 203

Ser Gly Tyr Asp Val Arg Val Gly Thr Gly Gly
  1               5                  10

<210> SEQ ID NO 204
<211> LENGTH: 11
<212> TYPE: PRT
<213> ORGANISM: Artificial sequence
<220> FEATURE:
<223> OTHER INFORMATION: sequence is synthesized

<400> SEQUENCE: 204

Ser Gly Gln Val Arg Pro Leu Ala Arg Gly Gly
  1               5                  10

<210> SEQ ID NO 205
<211> LENGTH: 11
<212> TYPE: PRT
<213> ORGANISM: Artificial sequence
<220> FEATURE:
<223> OTHER INFORMATION: sequence is synthesized

<400> SEQUENCE: 205

Ser Gly Arg Val Ala Ser Ser Arg Thr Gly Gly
  1               5                  10

<210> SEQ ID NO 206
<211> LENGTH: 11
<212> TYPE: PRT
<213> ORGANISM: Artificial sequence
<220> FEATURE:
<223> OTHER INFORMATION: sequence is synthesized

<400> SEQUENCE: 206

Ser Gly Leu Leu Arg Tyr Asn Ser Ser Gly Gly
  1               5                  10
```

<210> SEQ ID NO 207
<211> LENGTH: 11
<212> TYPE: PRT
<213> ORGANISM: Artificial sequence
<220> FEATURE:
<223> OTHER INFORMATION: sequence is synthesized

<400> SEQUENCE: 207

Ser Gly Val Val Thr Ser Arg Val Leu Gly Gly
 1               5                  10

<210> SEQ ID NO 208
<211> LENGTH: 14
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 8-9, 14
<223> OTHER INFORMATION: Unknown amino acid

<400> SEQUENCE: 208

Gly Glu Gly Val Glu Glu Glu Xaa Xaa Glu Trp Arg Gly Xaa
 1               5                  10

<210> SEQ ID NO 209
<211> LENGTH: 12
<212> TYPE: PRT
<213> ORGANISM: Artificial sequence
<220> FEATURE:
<223> OTHER INFORMATION: sequence is synthesized

<400> SEQUENCE: 209

Gly Glu Gly Val Glu Glu Glu Leu Trp Glu Trp Arg
 1               5                  10

<210> SEQ ID NO 210
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 8-9, 14-15
<223> OTHER INFORMATION: Unknown amino acid

<400> SEQUENCE: 210

Gly Glu Val Gly Glu Glu Glu Xaa Xaa Glu Trp Arg Gly Xaa Xaa
 1               5                  10                  15

Gly Gly

<210> SEQ ID NO 211
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 8-9, 14-15
<223> OTHER INFORMATION: Unknown amino acid

<400> SEQUENCE: 211

Gly Glu Glu Asp Asp Gly Glu Xaa Xaa Glu Trp Arg Gly Xaa Xaa
 1               5                  10                  15

Gly Gly

```
<210> SEQ ID NO 212
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 8-9, 14-15
<223> OTHER INFORMATION: Unknown amino acid

<400> SEQUENCE: 212

Gly Glu Gly Val Glu Glu Glu Xaa Xaa Glu Trp Arg Gly Xaa Xaa
 1               5                  10                  15

Gly Gly

<210> SEQ ID NO 213
<211> LENGTH: 17
<212> TYPE: PRT
<213> ORGANISM: Artificial sequence
<220> FEATURE:
<223> OTHER INFORMATION: sequence is synthesized

<400> SEQUENCE: 213

Gly Glu Gly Gly Glu Gly Val Phe Ser Glu Trp Arg Gly Val Trp
 1               5                  10                  15

Gly Gly

<210> SEQ ID NO 214
<211> LENGTH: 17
<212> TYPE: PRT
<213> ORGANISM: Artificial sequence
<220> FEATURE:
<223> OTHER INFORMATION: sequence is synthesized

<400> SEQUENCE: 214

Gly Asp Glu Val Glu Gly Glu Trp Ser Glu Trp Arg Gly Leu Arg
 1               5                  10                  15

Gly Gly

<210> SEQ ID NO 215
<211> LENGTH: 17
<212> TYPE: PRT
<213> ORGANISM: Artificial sequence
<220> FEATURE:
<223> OTHER INFORMATION: sequence is synthesized

<400> SEQUENCE: 215

Gly Glu Val Gly Asp Glu Glu His Trp Glu Trp Arg Gly Leu Gln
 1               5                  10                  15

Gly Gly

<210> SEQ ID NO 216
<211> LENGTH: 17
<212> TYPE: PRT
<213> ORGANISM: Artificial sequence
<220> FEATURE:
<223> OTHER INFORMATION: sequence is synthesized

<400> SEQUENCE: 216

Gly Glu Gly Val Glu Gly Glu Glu Glu Glu Trp Arg Gly Arg Val
 1               5                  10                  15

Gly Gly
```

```
<210> SEQ ID NO 217
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 13
<223> OTHER INFORMATION: Unknown amino acid

<400> SEQUENCE: 217

Gly Glu Val Gly Glu Gly Glu Ile Leu Glu Trp Arg Xaa Ser Asp
 1               5                  10                  15

Pro Asp

<210> SEQ ID NO 218
<211> LENGTH: 17
<212> TYPE: PRT
<213> ORGANISM: Artificial sequence
<220> FEATURE:
<223> OTHER INFORMATION: sequence is synthesized

<400> SEQUENCE: 218

Gly Glu Gly Gly Glu Gly Glu Ala Phe Glu Trp Arg Gly Tyr Arg
 1               5                  10                  15

Gly Gly

<210> SEQ ID NO 219
<211> LENGTH: 17
<212> TYPE: PRT
<213> ORGANISM: Artificial sequence
<220> FEATURE:
<223> OTHER INFORMATION: sequence is synthesized

<400> SEQUENCE: 219

Gly Glu Val Val Glu Glu Glu Leu Ser Glu Trp Arg Gly Phe Phe
 1               5                  10                  15

Gly Gly

<210> SEQ ID NO 220
<211> LENGTH: 17
<212> TYPE: PRT
<213> ORGANISM: Artificial sequence
<220> FEATURE:
<223> OTHER INFORMATION: sequence is synthesized

<400> SEQUENCE: 220

Gly Glu Val Gly Asp Glu Glu Ile Gln Glu Trp Arg Gly Leu Ser
 1               5                  10                  15

Gly Gly

<210> SEQ ID NO 221
<211> LENGTH: 17
<212> TYPE: PRT
<213> ORGANISM: Artificial sequence
<220> FEATURE:
<223> OTHER INFORMATION: sequence is synthesized

<400> SEQUENCE: 221

Gly Glu Gly Gly Asp Gly Glu Gln Val Glu Trp Arg Gly Gly Trp
 1               5                  10                  15

Gly Gly
```

<210> SEQ ID NO 222
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 4-5, 14-15
<223> OTHER INFORMATION: Unknown amino acid

<400> SEQUENCE: 222

Gly Glu Gly Xaa Xaa Gly Val Phe Leu Glu Trp Arg Gly Xaa Xaa
1               5                   10                  15

Gly Gly

<210> SEQ ID NO 223
<211> LENGTH: 17
<212> TYPE: PRT
<213> ORGANISM: Artificial sequence
<220> FEATURE:
<223> OTHER INFORMATION: sequence is synthesized

<400> SEQUENCE: 223

Gly Glu Gly Val Glu Gly Glu Trp Leu Glu Trp Arg Gly Met Ser
1               5                   10                  15

Gly Gly

<210> SEQ ID NO 224
<211> LENGTH: 17
<212> TYPE: PRT
<213> ORGANISM: Artificial sequence
<220> FEATURE:
<223> OTHER INFORMATION: sequence is synthesized

<400> SEQUENCE: 224

Gly Glu Gly Asp Glu Gly Leu Leu Glu Trp Arg Gly Gly Phe
1               5                   10                  15

Gly Gly

<210> SEQ ID NO 225
<211> LENGTH: 17
<212> TYPE: PRT
<213> ORGANISM: Artificial sequence
<220> FEATURE:
<223> OTHER INFORMATION: sequence is synthesized

<400> SEQUENCE: 225

Gly Glu Gly Gly Asp Gly Glu Tyr Trp Glu Trp Arg Gly Gly Arg
1               5                   10                  15

Gly Gly

<210> SEQ ID NO 226
<211> LENGTH: 17
<212> TYPE: PRT
<213> ORGANISM: Artificial sequence
<220> FEATURE:
<223> OTHER INFORMATION: sequence is synthesized

<400> SEQUENCE: 226

Gly Glu Val Val Glu Glu Glu Ala Trp Glu Trp Arg Gly Leu Leu
1               5                   10                  15

Gly Gly

```
<210> SEQ ID NO 227
<211> LENGTH: 17
<212> TYPE: PRT
<213> ORGANISM: Artificial sequence
<220> FEATURE:
<223> OTHER INFORMATION: sequence is synthesized

<400> SEQUENCE: 227

Gly Glu Val Val Asp Glu Glu Val Asn Glu Trp Arg Gly Phe Ala
 1               5                  10                  15

Gly Gly

<210> SEQ ID NO 228
<211> LENGTH: 17
<212> TYPE: PRT
<213> ORGANISM: Artificial sequence
<220> FEATURE:
<223> OTHER INFORMATION: sequence is synthesized

<400> SEQUENCE: 228

Gly Glu Gly Val Glu Gly Glu Leu Tyr Glu Trp Arg Gly Ile Leu
 1               5                  10                  15

Gly Gly

<210> SEQ ID NO 229
<211> LENGTH: 17
<212> TYPE: PRT
<213> ORGANISM: Artificial sequence
<220> FEATURE:
<223> OTHER INFORMATION: sequence is synthesized

<400> SEQUENCE: 229

Gly Glu Gly Asp Asp Glu Leu Phe Glu Trp Arg Gly Phe Leu
 1               5                  10                  15

Gly Val

<210> SEQ ID NO 230
<211> LENGTH: 17
<212> TYPE: PRT
<213> ORGANISM: Artificial sequence
<220> FEATURE:
<223> OTHER INFORMATION: sequence is synthesized

<400> SEQUENCE: 230

Gly Glu Val Val Glu Gly Glu Thr Phe Glu Trp Arg Gly Leu Thr
 1               5                  10                  15

Gly Gly

<210> SEQ ID NO 231
<211> LENGTH: 17
<212> TYPE: PRT
<213> ORGANISM: Artificial sequence
<220> FEATURE:
<223> OTHER INFORMATION: sequence is synthesized

<400> SEQUENCE: 231

Gly Glu Glu Val Glu Glu Glu Leu Trp Glu Trp Arg Gly Ala Thr
 1               5                  10                  15

Gly Gly

<210> SEQ ID NO 232
<211> LENGTH: 17
```

```
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 9
<223> OTHER INFORMATION: Unknown amino acid

<400> SEQUENCE: 232

Gly Glu Glu Val Asp Gly Glu Leu Xaa Glu Trp Arg Gly Gly Leu
 1               5                  10                  15

Gly Gly

<210> SEQ ID NO 233
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 5-6, 9
<223> OTHER INFORMATION: Unknown amino acid

<400> SEQUENCE: 233

Gly Glu Glu Val Xaa Xaa Glu Leu Xaa Glu Trp Arg Gly Gly Arg
 1               5                  10                  15

Gly Gly

<210> SEQ ID NO 234
<211> LENGTH: 17
<212> TYPE: PRT
<213> ORGANISM: Artificial sequence
<220> FEATURE:
<223> OTHER INFORMATION: sequence is synthesized

<400> SEQUENCE: 234

Gly Glu Glu Gly Asp Glu Asp Val Pro Glu Trp Arg Gly Phe Gly
 1               5                  10                  15

Gly Pro

<210> SEQ ID NO 235
<211> LENGTH: 17
<212> TYPE: PRT
<213> ORGANISM: Artificial sequence
<220> FEATURE:
<223> OTHER INFORMATION: sequence is synthesized

<400> SEQUENCE: 235

Gly Glu Gly Val Asp Gly Glu Ala Ile Glu Trp Arg Gly Leu Leu
 1               5                  10                  15

Gly Gly

<210> SEQ ID NO 236
<211> LENGTH: 17
<212> TYPE: PRT
<213> ORGANISM: Artificial sequence
<220> FEATURE:
<223> OTHER INFORMATION: sequence is synthesized

<400> SEQUENCE: 236

Gly Glu Glu Gly Glu Gly Glu Val Thr Glu Trp Arg Gly Met Leu
 1               5                  10                  15

Gly Gly
```

```
<210> SEQ ID NO 237
<211> LENGTH: 17
<212> TYPE: PRT
<213> ORGANISM: Artificial sequence
<220> FEATURE:
<223> OTHER INFORMATION: sequence is synthesized

<400> SEQUENCE: 237

Gly Glu Glu Gly Glu Gly Glu Glu Val Glu Trp Arg Gly Leu Ser
 1               5                  10                  15

Gly Gly

<210> SEQ ID NO 238
<211> LENGTH: 17
<212> TYPE: PRT
<213> ORGANISM: Artificial sequence
<220> FEATURE:
<223> OTHER INFORMATION: sequence is synthesized

<400> SEQUENCE: 238

Gly Glu Val Val Asp Gly Glu Gly Met Glu Trp Arg Gly Leu Ala
 1               5                  10                  15

Gly Gly

<210> SEQ ID NO 239
<211> LENGTH: 17
<212> TYPE: PRT
<213> ORGANISM: Artificial sequence
<220> FEATURE:
<223> OTHER INFORMATION: sequence is synthesized

<400> SEQUENCE: 239

Gly Glu Glu Asp Asp Glu Glu Ala Leu Glu Trp Arg Gly Leu Met
 1               5                  10                  15

Val Gly

<210> SEQ ID NO 240
<211> LENGTH: 17
<212> TYPE: PRT
<213> ORGANISM: Artificial sequence
<220> FEATURE:
<223> OTHER INFORMATION: sequence is synthesized

<400> SEQUENCE: 240

Gly Glu Glu Val Asp Gly Glu Ile Ala Glu Trp Arg Gly Leu Arg
 1               5                  10                  15

Gly Gly

<210> SEQ ID NO 241
<211> LENGTH: 17
<212> TYPE: PRT
<213> ORGANISM: Artificial sequence
<220> FEATURE:
<223> OTHER INFORMATION: sequence is synthesized

<400> SEQUENCE: 241

Gly Glu Val Val Glu Gly Glu Thr Val Glu Trp Arg Gly Ile Leu
 1               5                  10                  15

Gly Gly

<210> SEQ ID NO 242
<211> LENGTH: 17
```

```
<212> TYPE: PRT
<213> ORGANISM: Artificial sequence
<220> FEATURE:
<223> OTHER INFORMATION: sequence is synthesized

<400> SEQUENCE: 242

Gly Glu Val Gly Glu Gly Glu Met Ala Glu Trp Arg Gly Phe Arg
 1               5                  10                  15

Gly Gly

<210> SEQ ID NO 243
<211> LENGTH: 17
<212> TYPE: PRT
<213> ORGANISM: Artificial sequence
<220> FEATURE:
<223> OTHER INFORMATION: sequence is synthesized

<400> SEQUENCE: 243

Gly Glu Gly Gly Asp Glu Glu Leu Val Glu Trp Arg Gly Leu Ser
 1               5                  10                  15

Gly Gly

<210> SEQ ID NO 244
<211> LENGTH: 17
<212> TYPE: PRT
<213> ORGANISM: Artificial sequence
<220> FEATURE:
<223> OTHER INFORMATION: sequence is synthesized

<400> SEQUENCE: 244

Gly Glu Val Gly Glu Gly Glu Leu Ser Glu Trp Arg Ser Ile Trp
 1               5                  10                  15

Gly Gly

<210> SEQ ID NO 245
<211> LENGTH: 17
<212> TYPE: PRT
<213> ORGANISM: Artificial sequence
<220> FEATURE:
<223> OTHER INFORMATION: sequence is synthesized

<400> SEQUENCE: 245

Gly Glu Gly Gly Asp Glu Glu Phe Val Glu Trp Arg Gly Leu Gly
 1               5                  10                  15

Gly Gly

<210> SEQ ID NO 246
<211> LENGTH: 17
<212> TYPE: PRT
<213> ORGANISM: Artificial sequence
<220> FEATURE:
<223> OTHER INFORMATION: sequence is synthesized

<400> SEQUENCE: 246

Gly Glu Glu Gly Glu Gly Glu Val Arg Glu Trp Arg Gly Arg Ser
 1               5                  10                  15

Gly Gly

<210> SEQ ID NO 247
<211> LENGTH: 17
<212> TYPE: PRT
<213> ORGANISM: Artificial sequence
<220> FEATURE:
<223> OTHER INFORMATION: sequence is synthesized
```

```
<400> SEQUENCE: 247

Gly Glu Val Gly Asp Gly Glu Phe Met Glu Trp Arg Gly Phe Leu
 1               5                  10                  15

Gly Gly

<210> SEQ ID NO 248
<211> LENGTH: 17
<212> TYPE: PRT
<213> ORGANISM: Artificial sequence
<220> FEATURE:
<223> OTHER INFORMATION: sequence is synthesized

<400> SEQUENCE: 248

Gly Glu Val Val Glu Gly Glu Thr Phe Glu Trp Arg Gly Leu Thr
 1               5                  10                  15

Gly Gly

<210> SEQ ID NO 249
<211> LENGTH: 17
<212> TYPE: PRT
<213> ORGANISM: Artificial sequence
<220> FEATURE:
<223> OTHER INFORMATION: sequence is synthesized

<400> SEQUENCE: 249

Gly Glu Val Gly Glu Gly Glu Ile Ala Glu Trp Arg Gly Phe Ser
 1               5                  10                  15

Gly Gly

<210> SEQ ID NO 250
<211> LENGTH: 17
<212> TYPE: PRT
<213> ORGANISM: Artificial sequence
<220> FEATURE:
<223> OTHER INFORMATION: sequence is synthesized

<400> SEQUENCE: 250

Gly Glu Glu Gly Glu Gly Glu Val Met Glu Trp Arg Gly Ala Phe
 1               5                  10                  15

Gly Gly

<210> SEQ ID NO 251
<211> LENGTH: 17
<212> TYPE: PRT
<213> ORGANISM: Artificial sequence
<220> FEATURE:
<223> OTHER INFORMATION: sequence is synthesized

<400> SEQUENCE: 251

Gly Glu Gly Asp Asp Gly Glu Ile Thr Glu Trp Arg Gly Phe Met
 1               5                  10                  15

Gly Gly

<210> SEQ ID NO 252
<211> LENGTH: 17
<212> TYPE: PRT
<213> ORGANISM: Artificial sequence
<220> FEATURE:
<223> OTHER INFORMATION: sequence is synthesized

<400> SEQUENCE: 252

Gly Glu Gly Val Glu Glu Glu Leu Ser Glu Trp Arg Gly Leu Gly
```

```
            1               5                  10                  15

Gly Gly

<210> SEQ ID NO 253
<211> LENGTH: 17
<212> TYPE: PRT
<213> ORGANISM: Artificial sequence
<220> FEATURE:
<223> OTHER INFORMATION: sequence is synthesized

<400> SEQUENCE: 253

Gly Glu Glu Val Asp Gly Glu Ser Leu Glu Trp Arg Gly Ser Arg
  1               5                  10                  15

Gly Gly

<210> SEQ ID NO 254
<211> LENGTH: 17
<212> TYPE: PRT
<213> ORGANISM: Artificial sequence
<220> FEATURE:
<223> OTHER INFORMATION: sequence is synthesized

<400> SEQUENCE: 254

Gly Glu Gly Gly Ala Glu Glu Val Ile Glu Trp Arg Gly Gly Phe
  1               5                  10                  15

Gly Gly

<210> SEQ ID NO 255
<211> LENGTH: 17
<212> TYPE: PRT
<213> ORGANISM: Artificial sequence
<220> FEATURE:
<223> OTHER INFORMATION: sequence is synthesized

<400> SEQUENCE: 255

Gly Glu Gly Val Glu Glu Glu Phe Pro Glu Trp Arg Gly Tyr Trp
  1               5                  10                  15

Gly Gly

<210> SEQ ID NO 256
<211> LENGTH: 17
<212> TYPE: PRT
<213> ORGANISM: Artificial sequence
<220> FEATURE:
<223> OTHER INFORMATION: sequence is synthesized

<400> SEQUENCE: 256

Gly Glu Gly Gly Glu Gly Glu Thr Phe Glu Trp Arg Gly Leu Ser
  1               5                  10                  15

Gly Gly

<210> SEQ ID NO 257
<211> LENGTH: 17
<212> TYPE: PRT
<213> ORGANISM: Artificial sequence
<220> FEATURE:
<223> OTHER INFORMATION: sequence is synthesized

<400> SEQUENCE: 257

Gly Glu Gly Val Asp Gly Glu Ser Phe Glu Trp Arg Gly Gly Val
  1               5                  10                  15

Gly Gly
```

```
<210> SEQ ID NO 258
<211> LENGTH: 17
<212> TYPE: PRT
<213> ORGANISM: Artificial sequence
<220> FEATURE:
<223> OTHER INFORMATION: sequence is synthesized

<400> SEQUENCE: 258

Gly Glu Val Val Glu Gly Glu Glu Phe Glu Trp Arg Gly Val Arg
 1               5                  10                  15

Thr Pro

<210> SEQ ID NO 259
<211> LENGTH: 17
<212> TYPE: PRT
<213> ORGANISM: Artificial sequence
<220> FEATURE:
<223> OTHER INFORMATION: sequence is synthesized

<400> SEQUENCE: 259

Gly Glu Val Val Asp Glu Glu Ser Leu Glu Trp Arg Gly Leu Arg
 1               5                  10                  15

Gly Gly

<210> SEQ ID NO 260
<211> LENGTH: 17
<212> TYPE: PRT
<213> ORGANISM: Artificial sequence
<220> FEATURE:
<223> OTHER INFORMATION: sequence is synthesized

<400> SEQUENCE: 260

Gly Glu Glu Gly Asp Glu Glu Leu Val Glu Trp Arg Gly His Val
 1               5                  10                  15

Gly Gly

<210> SEQ ID NO 261
<211> LENGTH: 17
<212> TYPE: PRT
<213> ORGANISM: Artificial sequence
<220> FEATURE:
<223> OTHER INFORMATION: sequence is synthesized

<400> SEQUENCE: 261

Gly Glu Glu Gly Glu Glu Gly Phe Glu Trp Arg Gly Leu Leu
 1               5                  10                  15

Gly Gly

<210> SEQ ID NO 262
<211> LENGTH: 17
<212> TYPE: PRT
<213> ORGANISM: Artificial sequence
<220> FEATURE:
<223> OTHER INFORMATION: sequence is synthesized

<400> SEQUENCE: 262

Gly Glu Gly Gly Asp Gly Glu Ile Ala Glu Trp Arg Gly Ser Leu
 1               5                  10                  15

Gly Gly

<210> SEQ ID NO 263
<211> LENGTH: 17
<212> TYPE: PRT
```

```
<213> ORGANISM: Artificial sequence
<220> FEATURE:
<223> OTHER INFORMATION: sequence is synthesized

<400> SEQUENCE: 263

Gly Glu Gly Val Glu Glu Glu Leu Trp Glu Trp Arg Gly Phe Ala
  1               5                  10                  15

Gly Gly

<210> SEQ ID NO 264
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 17
<223> OTHER INFORMATION: Unknown amino acid

<400> SEQUENCE: 264

Gly Glu Gly Val Glu Glu Glu Val Ser Glu Trp Arg Tyr Pro Gly
  1               5                  10                  15

Gly Xaa

<210> SEQ ID NO 265
<211> LENGTH: 17
<212> TYPE: PRT
<213> ORGANISM: Artificial sequence
<220> FEATURE:
<223> OTHER INFORMATION: sequence is synthesized

<400> SEQUENCE: 265

Gly Glu Val Asp Glu Gly Glu Leu Leu Glu Trp Arg Gly Gly Leu
  1               5                  10                  15

Gly Gly

<210> SEQ ID NO 266
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 17
<223> OTHER INFORMATION: Unknown amino acid

<400> SEQUENCE: 266

Gly Glu Gly Val Glu Glu Glu Leu Phe Glu Trp Arg Gly Leu Gly
  1               5                  10                  15

Gly Xaa

<210> SEQ ID NO 267
<211> LENGTH: 17
<212> TYPE: PRT
<213> ORGANISM: Artificial sequence
<220> FEATURE:
<223> OTHER INFORMATION: sequence is synthesized

<400> SEQUENCE: 267

Gly Glu Val Gly Glu Gly Glu Ser Ser Glu Trp Arg Gly Ser Phe
  1               5                  10                  15

Gly Gly
```

```
<210> SEQ ID NO 268
<211> LENGTH: 17
<212> TYPE: PRT
<213> ORGANISM: Artificial sequence
<220> FEATURE:
<223> OTHER INFORMATION: sequence is synthesized

<400> SEQUENCE: 268

Gly Glu Gly Val Glu Glu Glu Leu Ser Glu Trp Arg Gly Tyr Val
 1               5                  10                  15

Gly Gly

<210> SEQ ID NO 269
<211> LENGTH: 17
<212> TYPE: PRT
<213> ORGANISM: Artificial sequence
<220> FEATURE:
<223> OTHER INFORMATION: sequence is synthesized

<400> SEQUENCE: 269

Gly Glu Glu Gly Asp Glu Glu Ser Leu Glu Trp Arg Gly Phe Glu
 1               5                  10                  15

Gly Gly

<210> SEQ ID NO 270
<211> LENGTH: 17
<212> TYPE: PRT
<213> ORGANISM: Artificial sequence
<220> FEATURE:
<223> OTHER INFORMATION: sequence is synthesized

<400> SEQUENCE: 270

Gly Glu Gly Gly Glu Gly Glu Leu Phe Glu Trp Arg Gly Leu Ser
 1               5                  10                  15

Gly Gly

<210> SEQ ID NO 271
<211> LENGTH: 17
<212> TYPE: PRT
<213> ORGANISM: Artificial sequence
<220> FEATURE:
<223> OTHER INFORMATION: sequence is synthesized

<400> SEQUENCE: 271

Gly Glu Gly Val Glu Glu Glu Leu Gln Glu Trp Arg Gly Val Trp
 1               5                  10                  15

Gly Gly

<210> SEQ ID NO 272
<211> LENGTH: 17
<212> TYPE: PRT
<213> ORGANISM: Artificial sequence
<220> FEATURE:
<223> OTHER INFORMATION: sequence is synthesized

<400> SEQUENCE: 272

Gly Glu Val Asp Asp Gly Glu Gly Phe Glu Trp Arg Gly Ala Arg
 1               5                  10                  15

Gly Gly

<210> SEQ ID NO 273
<211> LENGTH: 17
<212> TYPE: PRT
```

<213> ORGANISM: Artificial sequence
<220> FEATURE:
<223> OTHER INFORMATION: sequence is synthesized

<400> SEQUENCE: 273

Gly Glu Gly Val Glu Gly Glu Pro Val Glu Trp Arg Gly Leu Leu
1               5                   10                  15

Gly Gly

<210> SEQ ID NO 274
<211> LENGTH: 17
<212> TYPE: PRT
<213> ORGANISM: Artificial sequence
<220> FEATURE:
<223> OTHER INFORMATION: sequence is synthesized

<400> SEQUENCE: 274

Gly Glu Glu Gly Gln Glu Glu Arg Ser Glu Trp Arg Gly Gly Gly
1               5                   10                  15

Gly Thr

<210> SEQ ID NO 275
<211> LENGTH: 17
<212> TYPE: PRT
<213> ORGANISM: Artificial sequence
<220> FEATURE:
<223> OTHER INFORMATION: sequence is synthesized

<400> SEQUENCE: 275

Gly Glu Gly Asp Glu Gly Glu Trp Trp Glu Trp Arg Gly Leu Asn
1               5                   10                  15

Gly Arg

<210> SEQ ID NO 276
<211> LENGTH: 17
<212> TYPE: PRT
<213> ORGANISM: Artificial sequence
<220> FEATURE:
<223> OTHER INFORMATION: sequence is synthesized

<400> SEQUENCE: 276

Gly Glu Val Val Glu Gly Glu Val Leu Glu Trp Arg Gly Phe Ile
1               5                   10                  15

Gly Gly

<210> SEQ ID NO 277
<211> LENGTH: 17
<212> TYPE: PRT
<213> ORGANISM: Artificial sequence
<220> FEATURE:
<223> OTHER INFORMATION: sequence is synthesized

<400> SEQUENCE: 277

Gly Glu Gly Gly Asp Glu Glu Leu Pro Glu Trp Arg Gly Leu Gly
1               5                   10                  15

Gly Gly

<210> SEQ ID NO 278
<211> LENGTH: 17
<212> TYPE: PRT
<213> ORGANISM: Artificial sequence
<220> FEATURE:
<223> OTHER INFORMATION: sequence is synthesized

```
<400> SEQUENCE: 278

Gly Glu Gly Val Glu Glu Glu Met Leu Glu Trp Arg Gly Tyr Ala
  1               5                  10                  15

Gly Gly

<210> SEQ ID NO 279
<211> LENGTH: 17
<212> TYPE: PRT
<213> ORGANISM: Artificial sequence
<220> FEATURE:
<223> OTHER INFORMATION: sequence is synthesized

<400> SEQUENCE: 279

Gly Glu Gly Val Glu Gly Glu Ser Val Glu Trp Arg Gly Phe Val
  1               5                  10                  15

Gly Gly

<210> SEQ ID NO 280
<211> LENGTH: 17
<212> TYPE: PRT
<213> ORGANISM: Artificial sequence
<220> FEATURE:
<223> OTHER INFORMATION: sequence is synthesized

<400> SEQUENCE: 280

Gly Glu Glu Val Glu Glu Gly Leu Ile Glu Trp Arg Gly Phe Gly
  1               5                  10                  15

Gly Gly

<210> SEQ ID NO 281
<211> LENGTH: 17
<212> TYPE: PRT
<213> ORGANISM: Artificial sequence
<220> FEATURE:
<223> OTHER INFORMATION: sequence is synthesized

<400> SEQUENCE: 281

Gly Glu Val Asp Glu Glu Glu Leu Leu Glu Trp Arg Gly Arg Ser
  1               5                  10                  15

Gly Gly

<210> SEQ ID NO 282
<211> LENGTH: 17
<212> TYPE: PRT
<213> ORGANISM: Artificial sequence
<220> FEATURE:
<223> OTHER INFORMATION: sequence is synthesized

<400> SEQUENCE: 282

Gly Glu Gly Gly Glu Gly Glu Ala Leu Glu Trp Arg Gly Val Tyr
  1               5                  10                  15

Gly Gly

<210> SEQ ID NO 283
<211> LENGTH: 17
<212> TYPE: PRT
<213> ORGANISM: Artificial sequence
<220> FEATURE:
<223> OTHER INFORMATION: sequence is synthesized

<400> SEQUENCE: 283

Gly Glu Val Val Glu Glu Glu Leu Trp Glu Trp Arg Gly Ser Arg
  1               5                  10                  15
```

Gly Gly

<210> SEQ ID NO 284
<211> LENGTH: 17
<212> TYPE: PRT
<213> ORGANISM: Artificial sequence
<220> FEATURE:
<223> OTHER INFORMATION: sequence is synthesized

<400> SEQUENCE: 284

Gly Glu Gly Val Asp Gly Glu Ala Ile Glu Trp Arg Gly Gly Leu
 1               5                  10                  15

Gly Gly

<210> SEQ ID NO 285
<211> LENGTH: 17
<212> TYPE: PRT
<213> ORGANISM: Artificial sequence
<220> FEATURE:
<223> OTHER INFORMATION: sequence is synthesized

<400> SEQUENCE: 285

Gly Glu Val Val Glu Glu Val Met Glu Trp Arg Gly Gly Ser
 1               5                  10                  15

Gly Gly

<210> SEQ ID NO 286
<211> LENGTH: 17
<212> TYPE: PRT
<213> ORGANISM: Artificial sequence
<220> FEATURE:
<223> OTHER INFORMATION: sequence is synthesized

<400> SEQUENCE: 286

Gly Glu Glu Val Glu Gly Glu Ser Ala Glu Trp Arg Gly Leu Arg
 1               5                  10                  15

Gly Gly

<210> SEQ ID NO 287
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 16-17
<223> OTHER INFORMATION: Unknown amino acid

<400> SEQUENCE: 287

Gly Glu Gly Val Asp Gly Glu Arg Phe Glu Trp Arg Gly Leu Gly
 1               5                  10                  15

Xaa Xaa

<210> SEQ ID NO 288
<211> LENGTH: 17
<212> TYPE: PRT
<213> ORGANISM: Artificial sequence
<220> FEATURE:
<223> OTHER INFORMATION: sequence is synthesized

<400> SEQUENCE: 288

Gly Glu Glu Gly Asp Gly Glu Ile Leu Glu Trp Arg Gly Phe Ala
 1               5                  10                  15

Gly Gly

<210> SEQ ID NO 289
<211> LENGTH: 17
<212> TYPE: PRT
<213> ORGANISM: Artificial sequence
<220> FEATURE:
<223> OTHER INFORMATION: sequence is synthesized

<400> SEQUENCE: 289

Gly Asp Gly Gly Asp Glu Glu Val Ser Glu Trp Arg Gly Phe Lys
 1               5                  10                  15

Gly Gly

<210> SEQ ID NO 290
<211> LENGTH: 17
<212> TYPE: PRT
<213> ORGANISM: Artificial sequence
<220> FEATURE:
<223> OTHER INFORMATION: sequence is synthesized

<400> SEQUENCE: 290

Gly Glu Gly Val Glu Glu Glu Leu Pro Glu Trp Arg Gly Phe Thr
 1               5                  10                  15

Gly Gly

<210> SEQ ID NO 291
<211> LENGTH: 17
<212> TYPE: PRT
<213> ORGANISM: Artificial sequence
<220> FEATURE:
<223> OTHER INFORMATION: sequence is synthesized

<400> SEQUENCE: 291

Gly Glu Glu Gly Glu Glu Glu Leu Leu Glu Trp Arg Gly Phe Leu
 1               5                  10                  15

Gly Gly

<210> SEQ ID NO 292
<211> LENGTH: 17
<212> TYPE: PRT
<213> ORGANISM: Artificial sequence
<220> FEATURE:
<223> OTHER INFORMATION: sequence is synthesized

<400> SEQUENCE: 292

Gly Glu Val Gly Asp Gly Glu Leu Thr Ala Trp Arg Gly Leu Asn
 1               5                  10                  15

Gly Gly

<210> SEQ ID NO 293
<211> LENGTH: 17
<212> TYPE: PRT
<213> ORGANISM: Artificial sequence
<220> FEATURE:
<223> OTHER INFORMATION: sequence is synthesized

<400> SEQUENCE: 293

Gly Glu Val Gly Asp Gly Glu Leu Trp Glu Trp Arg Gly Leu Ala
 1               5                  10                  15

Gly Gly

```
<210> SEQ ID NO 294
<211> LENGTH: 17
<212> TYPE: PRT
<213> ORGANISM: Artificial sequence
<220> FEATURE:
<223> OTHER INFORMATION: sequence is synthesized

<400> SEQUENCE: 294

Gly Glu Glu Gly Asp Gly Glu Leu Met Glu Trp Arg Gly Phe Ala
 1               5                  10                  15

Gly Gly

<210> SEQ ID NO 295
<211> LENGTH: 17
<212> TYPE: PRT
<213> ORGANISM: Artificial sequence
<220> FEATURE:
<223> OTHER INFORMATION: sequence is synthesized

<400> SEQUENCE: 295

Gly Glu Gly Gly Glu Glu Glu Leu Ile Glu Trp Arg Gly Gly Phe
 1               5                  10                  15

Gly Gly

<210> SEQ ID NO 296
<211> LENGTH: 17
<212> TYPE: PRT
<213> ORGANISM: Artificial sequence
<220> FEATURE:
<223> OTHER INFORMATION: sequence is synthesized

<400> SEQUENCE: 296

Gly Glu Val Val Asp Gly Glu Asp Val Glu Trp Arg Gly Leu Asn
 1               5                  10                  15

Gly Gly

<210> SEQ ID NO 297
<211> LENGTH: 17
<212> TYPE: PRT
<213> ORGANISM: Artificial sequence
<220> FEATURE:
<223> OTHER INFORMATION: sequence is synthesized

<400> SEQUENCE: 297

Gly Glu Val Val Glu Gly Glu Leu Phe Glu Trp Arg Gly Leu Leu
 1               5                  10                  15

Gly Gly

<210> SEQ ID NO 298
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 17
<223> OTHER INFORMATION: Unknown amino acid

<400> SEQUENCE: 298

Gly Glu Gly Asp Asp Glu Glu Leu Phe Glu Trp Arg Gly Phe Leu
 1               5                  10                  15

Gly Xaa
```

```
<210> SEQ ID NO 299
<211> LENGTH: 17
<212> TYPE: PRT
<213> ORGANISM: Artificial sequence
<220> FEATURE:
<223> OTHER INFORMATION: sequence is synthesized

<400> SEQUENCE: 299

Gly Glu Val Gly Glu Glu Glu Leu Ser Glu Trp Arg Gly Phe Arg
 1               5                  10                  15

Gly Gly

<210> SEQ ID NO 300
<211> LENGTH: 17
<212> TYPE: PRT
<213> ORGANISM: Artificial sequence
<220> FEATURE:
<223> OTHER INFORMATION: sequence is synthesized

<400> SEQUENCE: 300

Gly Glu Gly Gly Glu Gly Glu Leu Pro Glu Trp Arg Gly Phe Leu
 1               5                  10                  15

Gly Gly

<210> SEQ ID NO 301
<211> LENGTH: 17
<212> TYPE: PRT
<213> ORGANISM: Artificial sequence
<220> FEATURE:
<223> OTHER INFORMATION: sequence is synthesized

<400> SEQUENCE: 301

Gly Glu Gly Gly Asp Glu Glu Leu Pro Glu Trp Arg Gly Leu Met
 1               5                  10                  15

Gly Gly

<210> SEQ ID NO 302
<211> LENGTH: 17
<212> TYPE: PRT
<213> ORGANISM: Artificial sequence
<220> FEATURE:
<223> OTHER INFORMATION: sequence is synthesized

<400> SEQUENCE: 302

Gly Glu Gly Gly Asp Gly Glu Met Val Glu Trp Arg Gly Pro Gly
 1               5                  10                  15

Gly Gly

<210> SEQ ID NO 303
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 2
<223> OTHER INFORMATION: Unknown amino acid

<400> SEQUENCE: 303

Gly Xaa Val Gly Glu Gly Glu Ser Leu Glu Trp Arg Gly Phe Arg
 1               5                  10                  15

Gly Gly
```

```
<210> SEQ ID NO 304
<211> LENGTH: 17
<212> TYPE: PRT
<213> ORGANISM: Artificial sequence
<220> FEATURE:
<223> OTHER INFORMATION: sequence is synthesized

<400> SEQUENCE: 304

Gly Glu Val Gly Glu Gly Glu Leu Phe Glu Trp Arg Gly Leu Gly
 1               5                   10                  15

Gly Gly

<210> SEQ ID NO 305
<211> LENGTH: 17
<212> TYPE: PRT
<213> ORGANISM: Artificial sequence
<220> FEATURE:
<223> OTHER INFORMATION: sequence is synthesized

<400> SEQUENCE: 305

Gly Glu Val Val Glu Gly Glu Pro Thr Glu Trp Arg Gly Val Arg
 1               5                   10                  15

Gly Gly

<210> SEQ ID NO 306
<211> LENGTH: 17
<212> TYPE: PRT
<213> ORGANISM: Artificial sequence
<220> FEATURE:
<223> OTHER INFORMATION: sequence is synthesized

<400> SEQUENCE: 306

Gly Glu Gly Val Glu Glu Glu Val Thr Glu Trp Arg Gly Ala Gly
 1               5                   10                  15

Gly Gly

<210> SEQ ID NO 307
<211> LENGTH: 17
<212> TYPE: PRT
<213> ORGANISM: Artificial sequence
<220> FEATURE:
<223> OTHER INFORMATION: sequence is synthesized

<400> SEQUENCE: 307

Gly Glu Val Val Glu Glu Glu Ser Pro Glu Trp Arg Gly Val Trp
 1               5                   10                  15

Ser Gly

<210> SEQ ID NO 308
<211> LENGTH: 17
<212> TYPE: PRT
<213> ORGANISM: Artificial sequence
<220> FEATURE:
<223> OTHER INFORMATION: sequence is synthesized

<400> SEQUENCE: 308

Gly Glu Val Val Asp Gly Glu Leu Ser Glu Trp Arg Gly Phe Ala
 1               5                   10                  15

Gly Gly

<210> SEQ ID NO 309
<211> LENGTH: 17
<212> TYPE: PRT
<213> ORGANISM: Artificial sequence
```

```
<220> FEATURE:
<223> OTHER INFORMATION: sequence is synthesized

<400> SEQUENCE: 309

Gly Glu Glu Val Glu Glu Glu Leu Trp Glu Trp Arg Gly Phe Gly
1               5                   10                  15

Gly Gly

<210> SEQ ID NO 310
<211> LENGTH: 17
<212> TYPE: PRT
<213> ORGANISM: Artificial sequence
<220> FEATURE:
<223> OTHER INFORMATION: sequence is synthesized

<400> SEQUENCE: 310

Gly Glu Glu Asp Glu Gly Glu Ser Trp Glu Trp Arg Gly Asn Arg
1               5                   10                  15

Gly Gly

<210> SEQ ID NO 311
<211> LENGTH: 17
<212> TYPE: PRT
<213> ORGANISM: Artificial sequence
<220> FEATURE:
<223> OTHER INFORMATION: sequence is synthesized

<400> SEQUENCE: 311

Gly Glu Val Gly Asp Glu Glu Leu Ser Glu Trp Arg Gly Gly Arg
1               5                   10                  15

Gly Gly

<210> SEQ ID NO 312
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 15
<223> OTHER INFORMATION: Unknown amino acid

<400> SEQUENCE: 312

Gly Glu Val Val Glu Glu Glu Ala Trp Glu Trp Arg Gly Leu Xaa
1               5                   10                  15

Gly Gly

<210> SEQ ID NO 313
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 15
<223> OTHER INFORMATION: Unknown amino acid

<400> SEQUENCE: 313

Gly Glu Gly Val Glu Gly Glu Leu Leu Glu Trp Arg Gly Leu Xaa
1               5                   10                  15

Gly Gly
```

```
<210> SEQ ID NO 314
<211> LENGTH: 17
<212> TYPE: PRT
<213> ORGANISM: Artificial sequence
<220> FEATURE:
<223> OTHER INFORMATION: sequence is synthesized

<400> SEQUENCE: 314

Gly Glu Glu Val Asp Glu Glu Tyr Phe Glu Trp Arg Gly Leu Leu
 1               5                  10                  15

Gly Gly

<210> SEQ ID NO 315
<211> LENGTH: 17
<212> TYPE: PRT
<213> ORGANISM: Artificial sequence
<220> FEATURE:
<223> OTHER INFORMATION: sequence is synthesized

<400> SEQUENCE: 315

Gly Glu Val Gly Glu Gly Glu Ser Asn Glu Trp Arg Gly Leu Phe
 1               5                  10                  15

Gly Gly

<210> SEQ ID NO 316
<211> LENGTH: 17
<212> TYPE: PRT
<213> ORGANISM: Artificial sequence
<220> FEATURE:
<223> OTHER INFORMATION: sequence is synthesized

<400> SEQUENCE: 316

Gly Glu Gly Val Glu Glu Glu Leu Val Glu Trp Arg Gly Leu Gly
 1               5                  10                  15

Gly Gly

<210> SEQ ID NO 317
<211> LENGTH: 17
<212> TYPE: PRT
<213> ORGANISM: Artificial sequence
<220> FEATURE:
<223> OTHER INFORMATION: sequence is synthesized

<400> SEQUENCE: 317

Gly Glu Gly Gly Glu Gly Glu Thr Phe Glu Trp Arg Gly Pro Leu
 1               5                  10                  15

Gly Gly

<210> SEQ ID NO 318
<211> LENGTH: 17
<212> TYPE: PRT
<213> ORGANISM: Artificial sequence
<220> FEATURE:
<223> OTHER INFORMATION: sequence is synthesized

<400> SEQUENCE: 318

Gly Glu Glu Gly Asp Gly Glu Val Phe Glu Trp Arg Gly Leu Met
 1               5                  10                  15

Gly Gly

<210> SEQ ID NO 319
<211> LENGTH: 17
<212> TYPE: PRT
<213> ORGANISM: Artificial sequence
```

```
<220> FEATURE:
<223> OTHER INFORMATION: sequence is synthesized

<400> SEQUENCE: 319

Gly Glu Gly Gly Glu Glu Glu Trp Phe Glu Trp Arg Gly Ile Trp
 1               5                  10                  15

Gly Gly

<210> SEQ ID NO 320
<211> LENGTH: 17
<212> TYPE: PRT
<213> ORGANISM: Artificial sequence
<220> FEATURE:
<223> OTHER INFORMATION: sequence is synthesized

<400> SEQUENCE: 320

Gly Glu Glu Gly Glu Glu Glu Leu Trp Glu Trp Arg Gly Gly Leu
 1               5                  10                  15

Gly Gly

<210> SEQ ID NO 321
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 3-4, 3-4, 6, 6, 9, 9
<223> OTHER INFORMATION: Unknown amino acid

<400> SEQUENCE: 321

Gly Glu Xaa Xaa Asp Xaa Glu Leu Xaa Glu Trp Arg Gly Leu Ser
 1               5                  10                  15

Gly Gly

<210> SEQ ID NO 322
<211> LENGTH: 17
<212> TYPE: PRT
<213> ORGANISM: Artificial sequence
<220> FEATURE:
<223> OTHER INFORMATION: sequence is synthesized

<400> SEQUENCE: 322

Gly Glu Gly Val Asp Glu Glu Leu Ile Glu Trp Arg Gly Leu Arg
 1               5                  10                  15

Gly Gly

<210> SEQ ID NO 323
<211> LENGTH: 17
<212> TYPE: PRT
<213> ORGANISM: Artificial sequence
<220> FEATURE:
<223> OTHER INFORMATION: sequence is synthesized

<400> SEQUENCE: 323

Gly Glu Gly Val Asp Gly Glu Ser Ala Glu Trp Arg Gly Leu Ser
 1               5                  10                  15

Gly Gly

<210> SEQ ID NO 324
<211> LENGTH: 17
<212> TYPE: PRT
<213> ORGANISM: Artificial sequence
```

```
<220> FEATURE:
<223> OTHER INFORMATION: sequence is synthesized

<400> SEQUENCE: 324

Gly Glu Gly Gly Glu Gly Glu Phe Trp Glu Trp Arg Gly Leu Pro
 1               5                  10                  15

Gly Gly

<210> SEQ ID NO 325
<211> LENGTH: 17
<212> TYPE: PRT
<213> ORGANISM: Artificial sequence
<220> FEATURE:
<223> OTHER INFORMATION: sequence is synthesized

<400> SEQUENCE: 325

Gly Glu Glu Gly Glu Gly Glu Ala Leu Glu Trp Arg Gly Phe Arg
 1               5                  10                  15

Gly Gly

<210> SEQ ID NO 326
<211> LENGTH: 17
<212> TYPE: PRT
<213> ORGANISM: Artificial sequence
<220> FEATURE:
<223> OTHER INFORMATION: sequence is synthesized

<400> SEQUENCE: 326

Gly Glu Val Val Asp Gly Glu Val Pro Glu Trp Arg Gly Phe Ser
 1               5                  10                  15

Gly Gly

<210> SEQ ID NO 327
<211> LENGTH: 17
<212> TYPE: PRT
<213> ORGANISM: Artificial sequence
<220> FEATURE:
<223> OTHER INFORMATION: sequence is synthesized

<400> SEQUENCE: 327

Gly Glu Val Gly Glu Glu Arg Ala Glu Trp Arg Gly Leu Arg
 1               5                  10                  15

Gly Gly

<210> SEQ ID NO 328
<211> LENGTH: 17
<212> TYPE: PRT
<213> ORGANISM: Artificial sequence
<220> FEATURE:
<223> OTHER INFORMATION: sequence is synthesized

<400> SEQUENCE: 328

Gly Glu Gly Val Glu Gly Glu Leu Ser Glu Trp Arg Gly Val Arg
 1               5                  10                  15

Gly Gly

<210> SEQ ID NO 329
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
```

-continued

```
<222> LOCATION: 5, 5, 8-9, 8-9, 14-15, 14-15
<223> OTHER INFORMATION: Unknown amino acid

<400> SEQUENCE: 329

Gly Glu Gly Val Xaa Gly Glu Xaa Xaa Glu Trp Arg Gly Xaa Xaa
 1               5                  10                  15

Gly Gly

<210> SEQ ID NO 330
<211> LENGTH: 17
<212> TYPE: PRT
<213> ORGANISM: Artificial sequence
<220> FEATURE:
<223> OTHER INFORMATION: sequence is synthesized

<400> SEQUENCE: 330

Gly Glu Val Val Asp Gly Glu Arg Phe Glu Trp Arg Gly Leu Leu
 1               5                  10                  15

Gly Gly

<210> SEQ ID NO 331
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 3, 3
<223> OTHER INFORMATION: Unknown amino acid

<400> SEQUENCE: 331

Gly Glu Xaa Gly Asp Gly Glu Val Phe Glu Trp Arg Gly Leu Met
 1               5                  10                  15

Gly Gly

<210> SEQ ID NO 332
<211> LENGTH: 17
<212> TYPE: PRT
<213> ORGANISM: Artificial sequence
<220> FEATURE:
<223> OTHER INFORMATION: sequence is synthesized

<400> SEQUENCE: 332

Gly Glu Gly Asp Glu Glu Glu Phe Pro Glu Trp Arg Gly Leu Leu
 1               5                  10                  15

Gly Gly

<210> SEQ ID NO 333
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 15-17
<223> OTHER INFORMATION: Unknown amino acid

<400> SEQUENCE: 333

Gly Glu Val Gly Glu Gly Glu Ile Leu Glu Trp Arg Gly Leu Xaa
 1               5                  10                  15

Xaa Xaa
```

```
<210> SEQ ID NO 334
<211> LENGTH: 17
<212> TYPE: PRT
<213> ORGANISM: Artificial sequence
<220> FEATURE:
<223> OTHER INFORMATION: sequence is synthesized

<400> SEQUENCE: 334

Gly Glu Val Gly Asp Gly Glu Ser Leu Glu Trp Arg Gly Gly Leu
 1               5                  10                  15

Gly Gly

<210> SEQ ID NO 335
<211> LENGTH: 17
<212> TYPE: PRT
<213> ORGANISM: Artificial sequence
<220> FEATURE:
<223> OTHER INFORMATION: sequence is synthesized

<400> SEQUENCE: 335

Gly Glu Gly Val Asp Gly Glu Thr Arg Glu Trp Arg Gly Gly Phe
 1               5                  10                  15

Gly Gly

<210> SEQ ID NO 336
<211> LENGTH: 17
<212> TYPE: PRT
<213> ORGANISM: Artificial sequence
<220> FEATURE:
<223> OTHER INFORMATION: sequence is synthesized

<400> SEQUENCE: 336

Gly Glu Val Val Glu Gly Glu Trp Leu Glu Trp Arg Gly Leu Leu
 1               5                  10                  15

Gly Gly

<210> SEQ ID NO 337
<211> LENGTH: 17
<212> TYPE: PRT
<213> ORGANISM: Artificial sequence
<220> FEATURE:
<223> OTHER INFORMATION: sequence is synthesized

<400> SEQUENCE: 337

Gly Glu Val Val Asp Gly Glu Leu Ala Glu Trp Arg Gly Leu Ala
 1               5                  10                  15

Gly Gly

<210> SEQ ID NO 338
<211> LENGTH: 17
<212> TYPE: PRT
<213> ORGANISM: Artificial sequence
<220> FEATURE:
<223> OTHER INFORMATION: sequence is synthesized

<400> SEQUENCE: 338

Gly Glu Glu Val Glu Gly Glu Ile Ala Glu Trp Arg Gly Leu Pro
 1               5                  10                  15

Gly Gly

<210> SEQ ID NO 339
<211> LENGTH: 17
<212> TYPE: PRT
<213> ORGANISM: Artificial sequence
```

<220> FEATURE:
<223> OTHER INFORMATION: sequence is synthesized

<400> SEQUENCE: 339

Gly Glu Gly Val Glu Gly Glu Tyr Thr Glu Trp Arg Gly Lys Ser
1               5                   10                  15

Gly Gly

<210> SEQ ID NO 340
<211> LENGTH: 17
<212> TYPE: PRT
<213> ORGANISM: Artificial sequence
<220> FEATURE:
<223> OTHER INFORMATION: sequence is synthesized

<400> SEQUENCE: 340

Gly Glu Val Val Glu Gly Glu Gly Pro Glu Trp Arg Gly Leu Trp
1               5                   10                  15

Gly Gly

<210> SEQ ID NO 341
<211> LENGTH: 17
<212> TYPE: PRT
<213> ORGANISM: Artificial sequence
<220> FEATURE:
<223> OTHER INFORMATION: sequence is synthesized

<400> SEQUENCE: 341

Gly Glu Gly Val Asp Gly Glu Val Trp Glu Trp Arg Gly Val Gly
1               5                   10                  15

Gly Gly

<210> SEQ ID NO 342
<211> LENGTH: 17
<212> TYPE: PRT
<213> ORGANISM: Artificial sequence
<220> FEATURE:
<223> OTHER INFORMATION: sequence is synthesized

<400> SEQUENCE: 342

Gly Glu Val Gly Asp Gly Glu Phe Met Glu Trp Arg Gly Leu Arg
1               5                   10                  15

Gly Gly

<210> SEQ ID NO 343
<211> LENGTH: 17
<212> TYPE: PRT
<213> ORGANISM: Artificial sequence
<220> FEATURE:
<223> OTHER INFORMATION: sequence is synthesized

<400> SEQUENCE: 343

Gly Glu Glu Val Glu Glu Glu Leu Trp Glu Trp Arg Gly Ala Thr
1               5                   10                  15

Gly Gly

<210> SEQ ID NO 344
<211> LENGTH: 15
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 8-9, 14-15
<223> OTHER INFORMATION: Unknown amino acid

<400> SEQUENCE: 344

Gly Glu Val Gly Glu Glu Glu Xaa Xaa Glu Trp Arg Gly Xaa Xaa
1               5                   10                  15

<210> SEQ ID NO 345
<211> LENGTH: 4
<212> TYPE: PRT
<213> ORGANISM: Artificial sequence
<220> FEATURE:
<223> OTHER INFORMATION: sequence is synthesized

<400> SEQUENCE: 345

Glu Asp Asp Gly
1

<210> SEQ ID NO 346
<211> LENGTH: 10
<212> TYPE: PRT
<213> ORGANISM: Artificial sequence
<220> FEATURE:
<223> OTHER INFORMATION: sequence is synthesized

<400> SEQUENCE: 346

Gly Gly Ser Gly Gly Asp Asp Asp Asp Lys
1               5                   10

<210> SEQ ID NO 347
<211> LENGTH: 12
<212> TYPE: PRT
<213> ORGANISM: Artificial sequence
<220> FEATURE:
<223> OTHER INFORMATION: sequence is synthesized

<400> SEQUENCE: 347

Gly Gly Ser Gly Gly Ser Gly Gly Ser Gly Gly Arg
1               5                   10

<210> SEQ ID NO 348
<211> LENGTH: 12
<212> TYPE: PRT
<213> ORGANISM: Artificial sequence
<220> FEATURE:
<223> OTHER INFORMATION: sequence is synthesized

<400> SEQUENCE: 348

Gly Gly Ser Gly Gly Ser Gly Gly Ser Gly Gly Ser
1               5                   10

<210> SEQ ID NO 349
<211> LENGTH: 12
<212> TYPE: PRT
<213> ORGANISM: Artificial sequence
<220> FEATURE:
<223> OTHER INFORMATION: sequence is synthesized

<400> SEQUENCE: 349

Gly Glu Gly Val Glu Glu Glu Leu Trp Glu Trp Ala
1               5                   10

<210> SEQ ID NO 350
<211> LENGTH: 11
<212> TYPE: PRT
<213> ORGANISM: Artificial sequence
<220> FEATURE:

<223> OTHER INFORMATION: sequence is synthesized

<400> SEQUENCE: 350

Gly Glu Gly Val Glu Glu Glu Leu Trp Glu Trp
 1               5                  10

<210> SEQ ID NO 351
<211> LENGTH: 12
<212> TYPE: PRT
<213> ORGANISM: Artificial sequence
<220> FEATURE:
<223> OTHER INFORMATION: sequence is synthesized

<400> SEQUENCE: 351

Gly Glu Glu Val Glu Glu Glu Leu Trp Glu Trp Arg
 1               5                  10

<210> SEQ ID NO 352
<211> LENGTH: 12
<212> TYPE: PRT
<213> ORGANISM: Artificial sequence
<220> FEATURE:
<223> OTHER INFORMATION: sequence is synthesized

<400> SEQUENCE: 352

Gly Glu Val Val Glu Glu Glu Leu Trp Glu Trp Arg
 1               5                  10

<210> SEQ ID NO 353
<211> LENGTH: 12
<212> TYPE: PRT
<213> ORGANISM: Artificial sequence
<220> FEATURE:
<223> OTHER INFORMATION: sequence is synthesized

<400> SEQUENCE: 353

Gly Glu Val Gly Asp Gly Glu Leu Trp Glu Trp Arg
 1               5                  10

<210> SEQ ID NO 354
<211> LENGTH: 12
<212> TYPE: PRT
<213> ORGANISM: Artificial sequence
<220> FEATURE:
<223> OTHER INFORMATION: sequence is synthesized

<400> SEQUENCE: 354

Gly Glu Glu Gly Glu Glu Glu Leu Trp Glu Trp Arg
 1               5                  10

<210> SEQ ID NO 355
<211> LENGTH: 15
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 8-9, 14-15
<223> OTHER INFORMATION: Unknown amino acid

<400> SEQUENCE: 355

Gly Glu Gly Val Glu Glu Glu Xaa Xaa Glu Trp Arg Gly Xaa Xaa
 1               5                  10                  15

FVIIA ANTAGONISTS

CROSS REFERENCE TO RELATED APPLICATION

This application claims the benefit of 35 U.S.C. § 119(e) to U.S. application Ser. No. 60/355,420 filed Feb. 6, 2002, which application is hereby incorporated by reference.

BACKGROUND OF THE INVENTION

1. Field of The Invention

This invention relates to novel compounds which prevent or block a Factor VIIa (FVIIa) mediated or associated process or event such as the catalytic conversion of Factor X (FX) to Factor Xa (FXa), Factor VII (FVII) to FVIIa or Factor IX (FIX) to Factor IXa (FIXa). In particular aspects, the compounds of the invention bind FVIIa or its zymogen FVII. The invention also relates to pharmaceutical compositions comprising the novel compounds as well as their use in research, diagnostic, therapeutic, and prophylactic methods.

2. Description of Related Disclosures

The tissue factor-Factor VIIa (TF-FVIIa) complex constitutes the primary initiator of the extrinsic pathway of blood coagulation (Carson, S. D., and Brozna, J. P., *Blood Coag. Fibrinol.* 4:281–292 (1993); Davie, E. W., et al., *Biochemistry* 30:10363–10370 (1991); Rapaport, S. I., and Rao, L. V. M., *Arterioscler. Thromb.* 12:1111–1121 (1992); Davie, E. W., *Thromb. Haemost.* 74: 1–6 (1995); Rapaport, S. I. and Rao, L. V. M., *Thromb. Haemost.* 74: 7–17 (1995); Mann, K. G., *Thromb. Haemost.* 82: 165–174 (1999); Edgington, T. S. et al., *Thromb. Haemost.* 78: 401–408 (1997)). The complex initiates the extrinsic pathway by activation of FX to FXa, FIX to FIXa, and additional FVII to FVIIa. The action of TF-FVIIa leads ultimately to the conversion of prothrombin to thrombin, which carries out many biological functions (Badimon, L., et al., *Trends Cardiovasc. Med.* 1:261–267 (1991)). Among the functions of thrombin is the conversion of fibrinogen to fibrin, which polymerizes to form a clot. The TF-FVIIa complex also participates as a secondary factor in extending the physiological effects of the contact activation system.

The involvement of these plasma protease systems has been suggested to play a significant role in a variety of clinical manifestations including arterial and venous thrombosis, septic shock, adult respiratory distress syndrome (ARDS), disseminated intravascular coagulation (DIC) and various other disease states (Haskel, E. J., et al., *Circulation* 84:821–827 (1991)); Holst, J., et al., *Haemostasis* 23(suppl. 1): 112–117 (1993); Creasey, A. A., et al., *J. Clin. Invest.* 91:2850–2860 (1993); see also, Colman, R. W., *N. Engl. J. Med.* 320:1207–1209 (1989); Bone, R. C., *Arch. Intern. Med.* 152:1381–1389 (1992) Presta, L. G. et al., *Thromb. Haemost.* 85: 379–389 (2001)).

Antibodies reactive with the protease domain of FVII have been shown to inhibit TF-FVIIa proteolytic function (Dickinson et al., *J. Mol. Biol.* 277:959–971 (1998)). Peptides corresponding to the EGF2 domain of FVII are potent inhibitors of TF-FVIIa mediated activation of FX (Husbyn et al., *J. Peptide Res.* 50:475–482 (1997); Presta supra). Several peptides corresponding to various regions of FVII (for example, amino acid sequence residues 372–337 and 103–112 of hFVII) have been proposed as therapeutic anticoagulants based upon their ability to inhibit TF-FVIIa mediated coagulation (International Publication No. WO 90/03390; International Publication No. W095/00541). Active site modified FVII variants capable of binding tissue factor (TF) have been proposed as pharmaceutical compositions for the prevention of TF/FVIIa mediated coagulation (International Publication No. WO 91/11514). U.S. Pat. Nos. 5,759,954, 5,863,893, 5,880,256 and 5,834,244 describe variant Kunitz-type serine protease inhibitors that inhibit TF-FVIIa activity and have been shown to prolong tissue factor initiated prothrombin time (PT). This is consistant with the ability of these TF-FVIIa active site inhibitors to prevent FX activation through inhibition of the TF-FVIIa complex.

The architecture of the active site of the serine proteases involved in the coagulation cascade is very similar. Although nonselective with respect to small chromogenic substrates, the proteases exhibit a strong specificity for their natural macromolecular substrates. Exosites on these enzymes play an important role in substrate recognition and specific cleavage. Blocking such interactions could result in the specific inhibition of a single protease in the coagulation pathway.

Two classes of peptide exosite inhibitors of human FVIIa have been identified (International Publication Number WO 01/10892; International Publication Number WO 01/01749; Dennis, M. S., et al. (2000) Nature, 404: 465–470; Dennis, M. S., et al. (2001) Biochemistry, 40: 9513–9521; Roberge, M., et al. (2001) Biochemistry, 40: 9522–9531). The two peptides classes are typified by peptides designated E-76 (TF76; SEQ ID NO: 8, International Publication Number WO 01/01749) and A-183 (TF183; SEQ ID NO: 23, International Publication Number WO 01/10892), which bind to two distinct exosites on the protease domain of FVIIa and inhibit the activation of FX to FXa by TF-FVIIa with IC50 values in the nanomolar range. Similar potency was observed for the inhibition of the amidolytic activity of TF-FVIIa using the peptides. Although these peptides are potent inhibitors of TF-FVIIa activity, they do not completely inhibit the enzymatic activity of FVIIa. At saturating concentrations of peptide, E-76 and A-183 show a maximal inhibition of FX activation of 90% and 78%, respectively, whereas maximal extent of inhibition of the amidolytic activity was 50% and 32%, respectively.

SUMMARY OF THE INVENTION

The present invention provides compounds and compositions which inhibit a FVII/FVIIa mediated or associated process such as the catalytic conversion of FVII to FVIIa, FIX to FIXa, or FX to FXa and thereby block initial events of the extrinsic pathway of blood coagulation. In addition, the compositions of the present invention /are capable of neutralizing the thrombotic effects of endogenous TF by binding to FVII or FVIIa and preventing the TF-FVIIa mediated activation of FX. In preferred embodiments the compositions provide for the complete inhibition of FVIIa and the TF-FVIIa complex providing, in preferred embodiments, for low dose pharmaceutical formulations. The compositions of the present invention are therefore useful in therapeutic and prophylactic methods for inhibiting TF-FVIIa mediated or associated processes.

The invention provides, in certain embodiments, for substrates for FVIIa. The substrates for FVIIa in combination with peptide exosite inhibitors of FVIIa described in International Publication Number WO 01/10892 comprise selective and complete inhibitors of FVIIa. The invention provides compounds which, by virtue of binding FVII or FVIIa, inhibit a FVII or FVIIa mediated coagulation event. Such compounds preferably bind FVII or FVIIa with a Kd less than about 100 µM, preferably less than about 100 nM, and preferably do not substantially inhibit the activity of other proteases of the coagulation cascade. In preferred embodiments, the compositions are peptides. Specific examples of such compounds include linear or cyclic peptides and combinations thereof, preferably between about 10 and 100 amino acid residues in length, optionally modified at the N-terminus or C-terminus or both, as well as their salts and derivatives, functional analogues thereof and extended peptide chains carrying amino acids or polypeptides at the termini of the sequences for use in the inhibition of FVIIa mediated activation of FX.

The invention further provides a method of inhibiting the activation of FX to FXa comprising contacting FVII with TF under conditions which allow formation of a TF-FVIIa complex in the presence of a peptide compound of the invention and further contacting the TF-FVIIa complex with FX. According to this aspect of the invention, the contacting steps may occur in vivo or in vitro.

The invention includes compositions, including pharmaceutical compositions, comprising compounds such as peptides for the treatment of a FVII/FVIIa mediated disorder as well as kits and articles of manufacture. Kits and articles of manufacture preferably include:

(a) a container;
(b) a label on or associated with said container; and
(c) a composition comprising a compound of the present invention contained within said container; wherein the composition is effective for treating a FVII/FVIIa mediated disorder. Preferably, the label on said container indicates that the composition can be used for treating a FVII/FVIIa mediated disorder and the compound in said composition comprises a compound which binds FVII/FVIIa and prevents FVII/FVIIa mediated activation of FX. The kits optionally include accessory components such as a second container comprising a pharmaceutically-acceptable buffer and instructions for using the composition to treat a disorder.

Also disclosed are methods useful in the treatment of coagulopathic disorders, especially those characterized by the involvement of FVII/FVIIa or the TF-FVIIa complex. Therefore, the invention provides a method of treating a FVII/FVIIa or TF-FVIIa mediated disease or disorder in a host in need thereof comprising administering to the host a therapeutically effective amount of a compound of the invention. The methods are useful in preventing, blocking or inhibiting a FVII/FVIIa or TF-FVIIa associated event. In preferred embodiments, the methods of the present invention are employed to reduce or prevent the severity of or the degree of tissue injury associated with blood coagulation.

The present invention further provides various dosage forms of the compounds of the present invention, including but not limited to, those suitable for parenteral, oral, rectal and pulmonary administration of a compound. In preferred aspects of the present invention a therapeutic dosage form is provided suitable for inhalation and the invention provides for the therapeutic treatment of diseases or disorders involving a FVII/FVIIa mediated or associated process or event, such as the activation of FX, via pulmonary administration of a compound of the invention. More particularly, the invention is directed to pulmonary administration of the compounds of the invention, especially the peptide compounds, by inhalation. Thus, the present invention provides an aerosol formulation comprising an amount of a compound of the invention, more particularly a peptide compound of the invention, effective to block or prevent a FVII/FVIIa mediated or associated process or event and a dispersant. In one embodiment, the compound of the invention, particularly the peptide compound of the invention, can be provided in a liquid aerosol formulation. Alternatively, the compound can be provided as a dry powder aerosol formulation. Therefore, according to the present invention, formulations are provided which provide an effective non-invasive alternative to other parenteral routes of administration of the compounds of the present invention for the treatment of FVII/FVIIa or TF-FVIIa mediated or associated events.

BRIEF DESCRIPTION OF THE DRAWINGS

FIG. 10. Amino acid sequences of selected peptides suitable for use in conjuction with the C terminal extension of the present invention.

DETAILED DESCRIPTION OF THE PREFERRED EMBODIMENTS

Definitions

Figure 1:
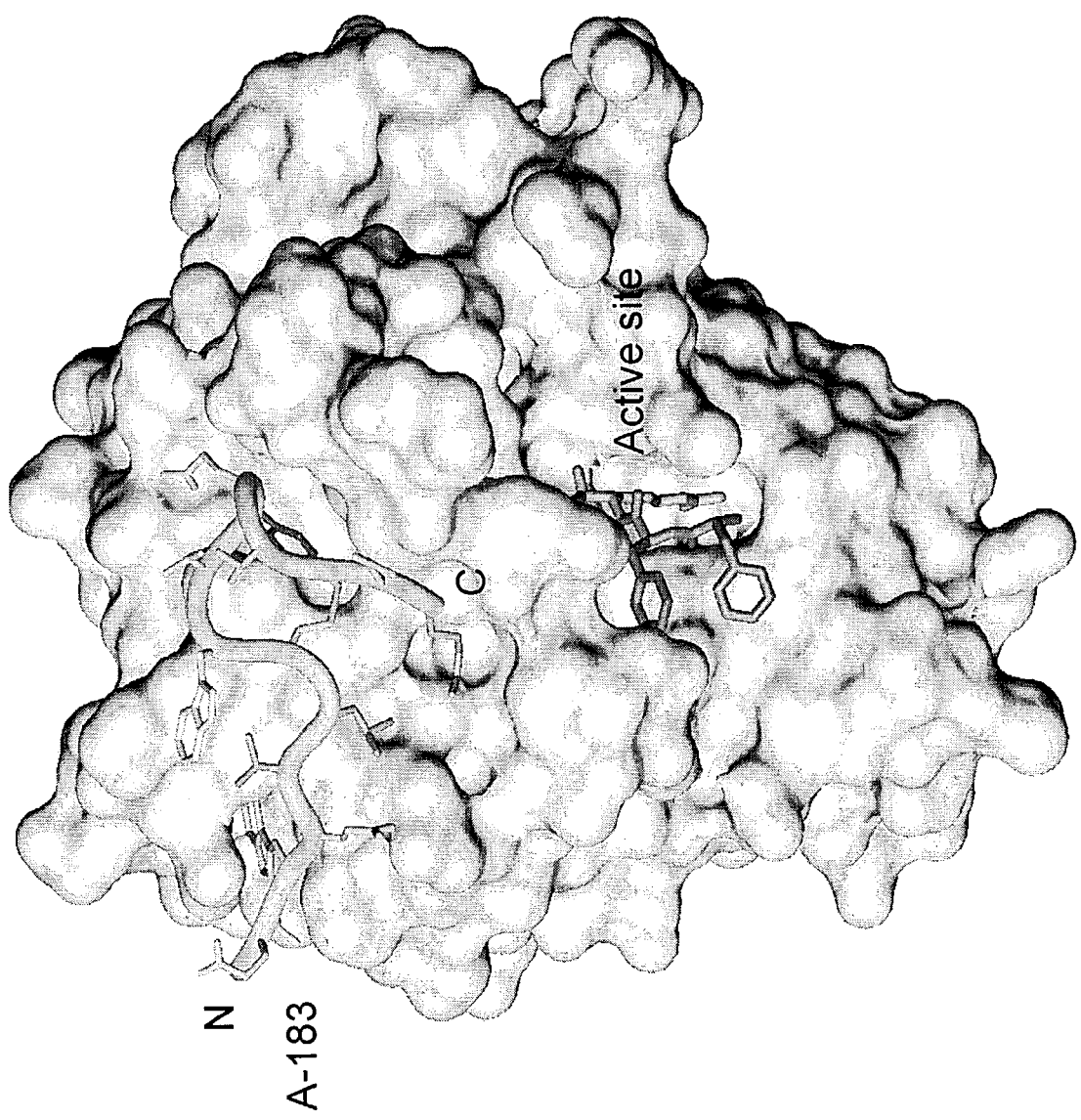
FIG. 1. Model of the protease domain of FVIIa. The protease domain of FVIIa is depicted as a model complexed with peptide A-183 at the A-exosite and D-Phe-L-Phe-L-Arg-chloromethylketone covalently bound to the active site (Roberge, M., et al., (2001) Biochemistry, 40: 9522–9531). The amino and carboxy terminal residues of A-183 are indicated.

Terms used in the claims and specification are defined as set forth below unless otherwise specified.

Abbreviations used throughout the description include: FIXa for Factor IXa and FIX for zymogen Factor IX; FXa for Factor Xa and FX for zymogen Factor X; FVII for zymogen factor VII; FVIIa for Factor VIIa; TF for tissue factor; TF-FVIIa for the tissue factor-Factor VIIa complex; FVII/FVIIa for FVII and/or FVIIa; sTF or TF$_{1-219}$ for soluble tissue factor composed of the extracellular domain amino acid residues 1–219; TF$_{1-243}$ for membrane tissue factor composed of the extracellular domain and transmembrane amino acid residues 1–243 (Paborsky et al., *J. Biol. Chem.* 266:21911–21916 (1991)); PT for prothrombin time; APTT for activated partial thromboplastin time.

The term "peptidell" is used herein to refer to constrained (that is, having some element of structure as, for example, the presence of amino acids which initiate a β turn or β pleated sheet, or for example, cyclized by the presence of disulfide bonded Cys residues) or unconstrained (e.g., linear) amino acid sequences of less than about 50 amino acid residues, and preferably less than about 40 amino acids residues, including multimers, such as dimers thereof or there between.

The term "amino acid" within the scope of the present invention is used in its broadest sense and is meant to include the naturally occurring L α-amino acids or residues. The commonly used one- and three-letter abbreviations for naturally occurring amino acids are used herein (Lehninger, A. L., *Biochemistry*, 2d ed., pp. 71–92, (Worth Publishers, New York, N.Y., 1975). The term includes D-amino acids as well as chemically modified amino acids such as amino acid analogs, naturally occurring amino acids that are not usually incorporated into proteins such as norleucine, and chemically synthesized compounds having properties known in the art to be characteristic of an amino acid. For example, analogs or mimetics of phenylalanine or proline, which allow the same conformational restriction of the peptide compounds as natural Phe or Pro are included within the definition of amino acid. Such analogs and mimetics are referred to herein as "functional equivalents" of an amino acid. Other examples of amino acids are listed by Roberts and Vellaccio, *The Peptides: Analysis, Synthesis, Biology*, Gross and Meiehofer, Eds., Vol. 5, p. 341 (Academic Press, Inc., New York, N.Y., 1983), which is incorporated herein by reference.

The term "conservative" amino acid substitution as used within this invention is meant to refer to amino acid substitutions which substitute functionally equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. The largest sets of conservative amino acid substitutions include:
(1) hydrophobic: His, Trp, Tyr, Phe, Met, Leu, Ile, Val, Ala;
(2) neutral hydrophilic: Cys, Ser, Thr;
(3) polar: Ser, Thr, Asn, Gln;
(4) acidic/negatively charged: Asp, Glu;
(5) charged: Asp, Glu, Arg, Lys, His;
(6) positively charged: Arg, Lys, His;
(7) basic: His, Lys, Arg;
(8) residues that influence chain orientation: Gly, Pro; and
(9) aromatic: Trp, Tyr, Phe, His.

In addition, structurally similar amino acids can substitute conservatively for some of the specific amino acids. Groups of structurally similar amino acids include: (Ile, Leu, and Val); (Phe and Tyr); (Lys and Arg); (Gln and Asn); (Asp and Glu); and (Gly and Ala). In this regard, it is understood that amino acids are substituted on the basis of side chain bulk, charge and/or hydrophobicity.

Amino acid residues can be further classified as cyclic or noncyclic, aromatic or non aromatic with respect to their side chain groups these designations being commonplace to the skilled artisan.

| Original Residue | Exemplary Conservative Substitution | Preferred Conservative Substitution |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro | Pro |
| His | Asn, Gln, Lys, Arg | Arg |
| Ile | Leu, Val, Met, Ala Phe | Leu |
| Leu | Ile, Val Met, Ala, Phe | Ile |
| Lys | Arg, Gln, Asn | Arg |
| Met | Leu, Phe, Ile | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe | Leu |
| Ala | | |

Peptides synthesized by the standard solid-phase synthesis techniques described here, for example, are not limited to amino acids encoded by genes for substitutions involving the amino acids. Commonly encountered amino acids which are not encoded by the genetic code include, for example, those described in International Publication No. WO 90/01940 and described in Table 1 below, as well as, for example, 2-amino adipic acid (Aad) for Glu and Asp; 2-aminopimelic acid (Apm) for Glu and Asp; 2-aminobutyric (Abu) acid for Met, Leu, and other aliphatic amino acids; 2-aminoheptanoic acid (Ahe) for Met, Leu and other aliphatic amino acids; 2-aminoisobutyric acid (Aib) for Gly; cyclohexylalanine (Cha) for Val, and Leu and Ile; homoarginine (Har) for Arg and Lys; 2,3-diaminopropionic acid (Dpr) for Lys, Arg and His; N-ethylglycine (EtGly) for Gly, Pro, and Ala; N-ethylglycine (EtGly) for Gly, Pro, and Ala; N-ethylasparigine (EtAsn) for Asn, and Gln; Hydroxyllysine (Hyl) for Lys; allohydroxyllysine (AHyl) for Lys; 3-(and 4)hydoxyproline (3Hyp, 4Hyp) for Pro, Ser, and Thr; allo-isoleucine (AIle) for Ile, Leu, and Val; ρ-amidinophenylalanine for Ala; N-methylglycine (MeGly, sarcosine) for Gly, Pro, and Ala; N-methylisoleucine (MeIle) for Ile; Norvaline (Nva) for Met and other aliphatic amino acids; Norleucine (Nle) for Met and other aliphatic amino acids; Ornithine (Orn or Or) for Lys, Arg and His; Citrulline (Cit) and methionine sulfoxide (MSO) for Thr, Asn and Gln; -methylphenylalanine (MePhe), trimethylphenylalanine, halo (F, Cl, Br, and I)phenylalanine, trifluoroylphenylalanine, for Phe.

TABLE 1

Abbreviations used in the specification

| Compound | Abbreviation | |
|---|---|---|
| Acetyl | Ac | |
| Alanine | Ala | A |
| 3-(2-Thiazolyl)-L-alanine | Tza | |
| Arginine | Arg | R |
| Asparagine | Asn | N |
| Aspartic acid | Asp | D |
| t-Butyloxycarbonyl | Boc | |
| Benzotriazol-1-yloxy-tris-(dimethylamino)-phosphonium-hexafluorophosphate | Bop | |
| β-Alanine | βAla | |
| β-Valine | βVal | |
| β-(2-Pyridyl)-alanine | Pal (2) | |
| β-(3-Pyridyl)-alanine | Pal (3) | |
| β-(4-Pyridyl)-alanine | Pal (4) | |
| β-(3-N-Methylpyridinium)-alanine | PalMe (3) | |
| t-Butyl | tBu, But | |
| t-Butyloxycarbonyl | Boc | |
| Caffeic acid | Caff | |
| Cysteine | Cys | C |
| Cyclohexylalanine | Cha | |
| Cyclohexylglycine | Chg | |
| 3,5-Dinitrotyrosine | Tyr (3,5-No$_2$) | |
| 3,5-Diiodotyrosine | Tyr (3,5-I) | |
| 3,5-Dibromotyrosine | Tyr (3,5-Br) | |
| 9-Fluorenylmethyloxy-carbonyl | Fmoc | |
| Glutamine | Gln | Q |
| Glutamic acid | Glu | E |
| γ-Carboxyglutamic acid | Gla | |
| Glycine | Gly | G |
| Histidine | His | H |
| Homoarginine | hArg | |
| 3-Hydroxyproline | Hyp | |
| Isoleucine | Ile | I |
| Leucine | Leu | L |
| tert-Leucine | Tle | |
| Lysine | Lys | K |
| Mercapto-β,β-cyclopentamethylene-propionic acid | Mpp | |
| Mercaptoacetic acid | Mpa | |
| Mercaptopropionic acid | Mpr | |
| Methionine | Met | M |
| β-Naphthylalanine | Na | |
| Nicotinic acid | Nic | |
| Nipecotic acid | Npa | |
| N-methyl nicotinic acid | NicMe | |
| Norarginine | nArg | |
| Norleucine | Nle nL | |
| Norvaline | Nva | |
| Ornithine | Orn or Or | |
| Ornithine-derived dimethylamidinium | Orn (N$^\delta$—C$_3$H$_7$N) | |

TABLE 1-continued

Abbreviations used in the specification

| Compound | Abbreviation | |
|---|---|---|
| Phenylalanine | Phe | F |
| p-Guanidinophenylalanine | Phe (Gua) | |
| p-Aminophenylalanine | Phe (NH$_2$) | |
| p-Chlorophenylalanine | Phe (Cl) | |
| p-Flurophenylalanine | Phe (F) | |
| p-Nitrophenylalanine | Phe (NO$_2$) | |
| p-Hydroxyphenylglycine | Pgl (OH) | |
| p-Toluenesulfonyl | Tos | |
| m-Amidinophenylalanine | mAph | |
| p-Amidinophenylalanine | pAph | |
| Phenylglycine | Pgl | |
| Phenylmalonic acid | Pma | |
| Proline | Pro | P |
| 4-Quinolinecarboxy | 4-Qca | |
| Sarcosine | Sar | |
| Serine | Ser | S |
| Succinyl | Suc | |
| Threonine | Thr | T |
| Tryptophan | Trp | W |
| Tyrosine | Tyr | Y |
| 3-iodotyrosine | Tyr (3-I) | |
| O-Methyl tyrosine | Tyr (Me) | |
| Valine | Val | V |

* Amino acids of D configuration are denoted by D-prefix using three-letter code (eg., D-Ala, D-Cys, D-Asp, D-Trp).

A useful method for identification of certain residues or regions of the compound for amino acid substitution other than those described herein is called alanine scanning mutagenesis as described by Cunningham and Wells, *Science* 244:1081–1085 (1989). Here a residue or group of target residues are identified (e.g., charged residues such as Arg, Asp, His, Lys, and Glu) and replaced by a neutral or negatively charged amino acid to affect the interaction of the amino acids with the surrounding aqueous environment in or outside the cell. Those regions demonstrating functional sensitivity to the substitution are then refined by introducing further or other variations at or for the sites of substitution. Thus while the site for introducing an amino acid sequence variation is predetermined the nature of the mutation per se need not be predetermined. For example, to optimize the performance of a mutation at a given site, Ala scanning or random mutagenesis may be conducted at the target codon or region and the expressed compound screened for the optimal combination of desired activity.

Phage display of protein or peptide libraries offers another methodology for the selection of compounds with improved affinity, altered specificity, or improved stability (Smith, G. P., *Curr. Opin. Biotechnol.* 2:668–673 (1991); Lowman, *Ann. Rev. Biophys. Biomol. Struct.* 26:401–404 (1997)). High affinity proteins, displayed in a monovalent fashion as fusions with the M13 gene III coat protein (Clackson, T., et al., *Trends Biotechnol.* 12:173–183 (1994)), can be identified by cloning and sequencing the corresponding DNA packaged in the phagemid particles after a number of rounds of binding selection.

Preferred amino acid sequences within the context of the present invention are non-naturally occurring amino acid sequences. By non-naturally occurring is meant that the amino acid sequence is not found in nature. These include peptides, peptide analogs and mimetics containing naturally as well as non-naturally occurring amino acids. Especially preferred are sequences as described above consisting of naturally occurring amino acids.

A TF-FVIIa mediated or associated process or event, or equivalently, an activity associated with plasma FVII/FVIIa, according to the present invention is any event which requires the presence of FVIIa. The general mechanism of blood clot formation is reviewed by Ganong, in *Review of Medical Physiology*, 13th ed., pp.411–414 (Lange, Los Altos, Calif., 1987). Coagulation requires the confluence of two processes, the production of thrombin which induces platelet aggregation and the formation of fibrin which renders the platelet plug stable. The process comprises several stages each requiring the presence of discrete proenzymes and procofactors. The process ends in fibrin crosslinking and thrombus formation. Fibrinogen is converted to fibrin by the action of thrombin. Thrombin, in turn, is formed by the proteolytic cleavage of prothrombin. This proteolysis is effected by FXa which binds to the surface of activated platelets and in the presence of FVa and calcium, cleaves prothrombin. TF-FVIIa is required for the proteolytic activation of FX by the extrinsic pathway of coagulation. Therefore, a process mediated by or associated with TF-FVIIa, or an activity associated with FVII/FVIIa includes any step in the coagulation cascade from the formation of the TF-FVIIa complex to the formation of a fibrin platelet clot and which initially requires the presence FVII/FVIIa. For example, the TF-FVIIa complex initiates the extrinsic pathway by activation of FX to FXa, FIX to FIXa, and additional FVII to FVIIa.

TF-FVIIa mediated or associated process, or FVII/FVIIa mediated or associated activity, can be conveniently measured employing standard assays, such as those described in Roy, S., *J. Biol. Chem.* 266:4665–4668 (1991), O'Brien, D., et al., *J. Clin. Invest.* 82:206–212 (1988), Lee et al., *Biochemistry* 36:5607–5611 (1997), Kelly et al., *J. Biol. Chem.* 272:17467–17472 (1997), for the conversion of chromogenic substrates or Factor X to Factor Xa in the presence of Factor VII and other necessary reagents.

A TF-FVIIa related disease or disorder is meant to include chronic thromboembolic diseases or disorders associated with fibrin formation including vascular disorders such as deep venous thrombosis, arterial thrombosis, stroke, tumor metastasis, thrombolysis, arteriosclerosis and restenosis following angioplasty, acute and chronic indications such as inflammation, septic shock, septicemia, hypotension, adult respiratory distress syndrome (ARDS), disseminated intravascular coagulapathy (DIC) and other diseases. The TF-FVIIa related disorder is not limited to in vivo coagulopathic disorders such as those named above but includes inappropriate or undesirable coagulation related to circulation of blood through stents or artificial valves or related to extracorporeal circulation including blood removed in-line from a patient in such processes as dialysis procedures, blood filtration, or blood bypass during surgery.

As used herein, the term "pulmonary administration" refers to administration of a formulation of the invention through the lungs by inhalation. As used herein, the term "inhalation" refers to intake of air to the alveoli. In specific examples, intake can occur by self-administration of a formulation of the invention while inhaling, or by administration via a respirator, e.g., to a patient on a respirator. The term "inhalation" used with respect to a formulation of the invention is synonymous with "pulmonary administration."

As used herein, the term "parenteral" refers to introduction of a compound of the invention into the body by other than the intestines, and in particular, intravenous (i.v.), intraarterial (i.a.), intraperitoneal (i.p.), intramuscular (i.m.), intraventricular, and subcutaneous (s.c.) routes.

As used herein, the term "aerosol" refers to suspension in the air. In particular, aerosol refers to the particlization of a formulation of the invention and its suspension in the air. According to the present invention, an aerosol formulation is a formulation comprising a compound of the present invention that is suitable for aerosolization, i.e., particlization and suspension in the air, for inhalation or pulmonary administration.

The term "treatment" as used within the context of the present invention is meant to include therapeutic treatment as well as prophylactic, or suppressive measures for the disease or disorder. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment", of the disease. Further, administration of the agent after onset and after clinical symptoms have developed where administration affects clinical parameters of the disease or disorder, such as the degree of tissue injury or the amount or extent of leukocyte trafficking and perhaps amelioration of the disease, comprises "treatment" of the disease.

Those "in need of treatment" include mammals, such as humans, already having the disease or disorder, including those in which the disease or disorder is to be prevented.

MODES FOR CARRYING OUT THE INVENTION

Selection of Compounds

The present invention provides for, among other things, the specific and complete inhibition of FVIIa. In particular embodiments, the invention provides a molecule which specifically binds the FVIIa active site based upon the interaction of FVIIa with a peptide ligand of FVIIa described in International Publication Number WO 01/10892. In preferred embodiment the invention provides peptide inhibitors of FVIIa which comprise a peptide ligand of International Publication No. WO 01/10892 and a C-terminal peptide extension described herein. The peptide inhibitors of the present invention preferably provide complete inhibition of FVIIa enzymatic and amidolytic activity.

In order to determine both the length and the sequence of the peptide extension of the present invention, a novel substrate phage display strategy may be employed. Substrate phage display has been successfully employed to determine preferred cleavage sequences for proteases (Matthews, D. A. and Wells, J. A. (1993) Science 260: 1113–1117; Smith, M. M. et al. (1995) J. Biol. Chem. 270:6440–6449; Harris J. L. et al. (1998) J. Biol. Chem. 273: 27364–27373; Ke S. H. et al. (1997) J. Biol. Chem. 272: 20456–20462; Kridel, S. J. et al. (2001) Anal. Biochem. 294: 176–184). According to certain aspects of the present invention, a substrate phage library is displayed between an anchor that binds to a specific target protease such as FVIIa and one of the phage coat proteins. The activation of the immobilized protease results in the release of phage displaying preferred protease substrate sequences. Phage in the supernatant are subjected to propagation and preferred substrate sequences are determined by sequencing of selected phage. The immobilization of the phage library by the protease and the selective propagation of released phage due to proteolytic cleavage, creates the basis for selection in this assay. According to the present invention preferred the preferred protease is FVIIa and preferred anchors for the selection of peptide extensions are the peptide ligands described in International Publication Number WO 01/10892.

Figure 4:
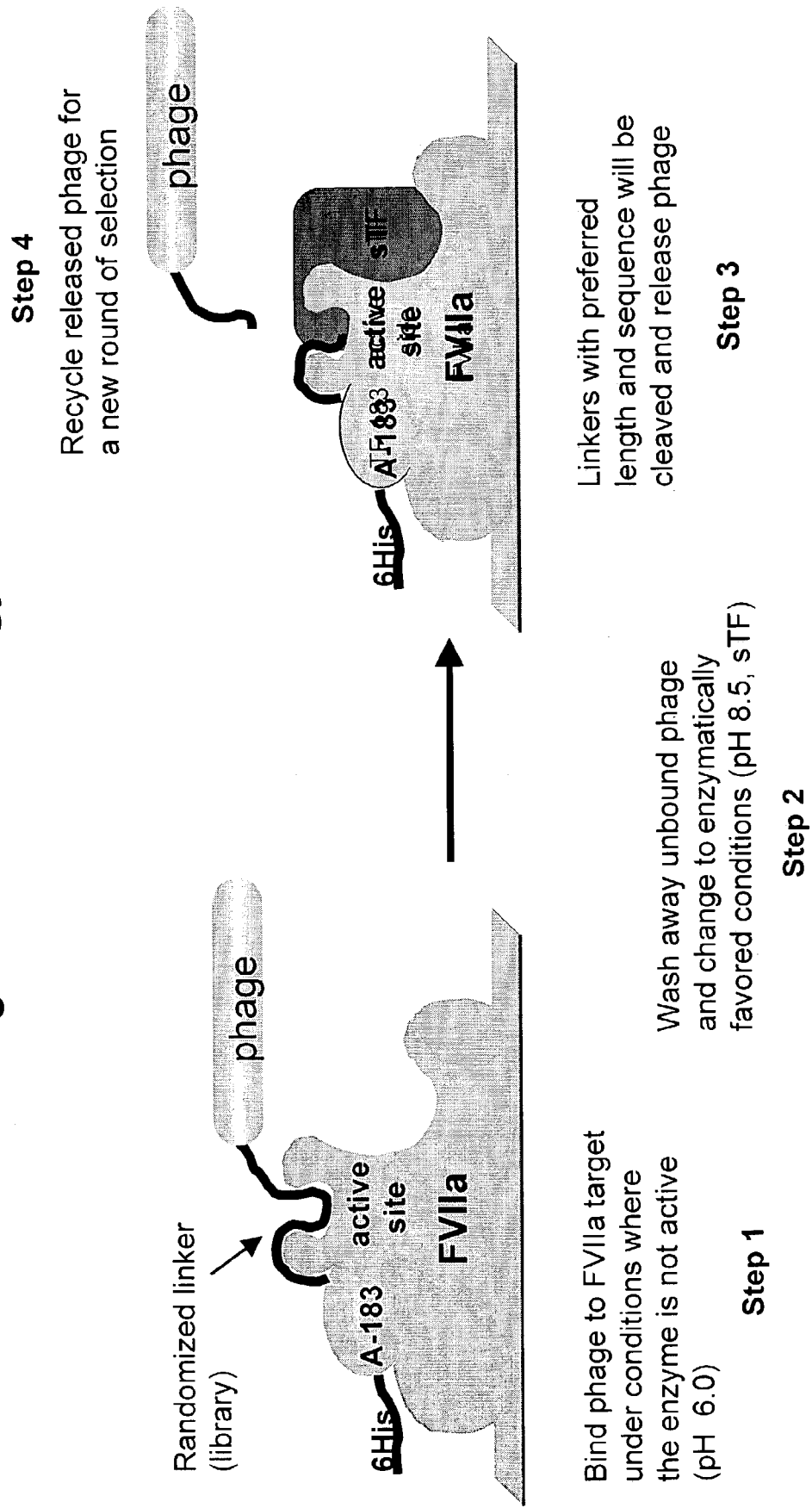
FIG. 4. Phage selection strategy. The substrate phage libraries in binding buffer (pH 6.0) were incubated with immobilized FVIIa for 1 h. Unbound phage were removed by repetitive washing with binding buffer. Bound phage were immediately incubated for 5 min with cleavage buffer (pH 8.5 and sTF). The supernatants were incubated with immobilized tetra-His-monoclonal Antibody to pull out any uncleaved phage. These supernatants were then subjected to propagation and further rounds of selection.

In the context of the present invention, a peptide ligand, such as the inhibitor A-183 of International Publication Number WO 01/10892 serves as an anchor to bind FVIIa which serves as both binding target and the cleavage enzyme. A peptide ligand such as A-183 is used as the anchor to bring the substrate library in close proximity to the active site of FVIIa under conditions where the enzyme is not active. Upon activation of FVIIa by addition of its obligate cofactor TF and modification of the pH, only phage with suitable sequences for enzymatic cleavage by TF-FVIIa are released and propagated (FIG. 4).

Employing this strategy, peptide extensions may be obtained which show complete (>~99%) inhibition of FX activation an improvement in potency (IC50=12 pM) over the peptide ligand itself and a more dramatic effect as an anticoagulant in PT clotting assays.

Peptides Ligards

According to the invention a peptide extension described herein forms a C-terminal extension of a peptide ligand of International Publication No. WO 01/10892. Preferred peptides of International Publication No. WO 01/10892 are fifteen (15) amino acid peptides having the following formula:

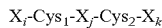

wherein $X_i$ is absent or is a peptide of 6 amino acids; $X_j$ is 5 amino acids and $X_k$ is a peptide of 2 amino acids.

Preferred peptides include peptides such as those described above comprising the following sequence:

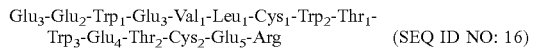  (SEQ ID NO: 16)

wherein $Glu_1$ and $Glu_2$ are optionally absent or any amino acid, $Trp_1$ is Trp or an amino acid selected from the group consisting of, Phe, Tyr, Leu, Ile, Met, Val and Ala; $Glu_3$ is Glu or any other amino acid; $Val_1$ is Val or an amino acid selected from the group consisting of Trp, Phe, Tyr, Leu, Ile, Met and Ala; $Leu_1$ is Leu or an amino acid selected from the group consisting of Leu, Trp, Phe, Tyr, Ile Met, Val and Ala; $Trp_2$ is amino acid selected from the group consisting of Trp, Phe, Tyr, Leu, Ile, Met, Val and Ala; $Thr_1$ is any amino acid; $Trp_3$ is an amino acid selected from the group consisting of Trp, Phe, Tyr, Leu, Ile, Met, Val and Ala; $Glu_4$ is any amino acid; $Thr_2$ is any amino acid; $Glu_5$ is any amino acid and Arg is an amino acid selected from the group consisting of Arg, Lys, Leu, Trp, His, Met and Ile. Peptides of this variety may contain N-terminal amino acid extensions.

Preferred amino acids according to this aspect of the invention comprise the sequence $Trp_1$-$Glu_1$-Val-Leu-$Cys_1$-$Trp_2$-$Thr_1$-$Trp_3$-$Glu_2$-$Thr_2$-$Cys_2$-$Glu_3$-Arg (SEQ ID NO:40) or having between 1 and 8 amino acids of SEQ ID NO:40 substituted; or between 1 and 6 amino acids of SEQ ID NO:40 substituted, or between 1 and 4 amino acids substituted, or between 1 or 2 amino acids of SEQ ID NO:40 substituted. According to this aspect of the invention; $Trp_1$ is an amino acid selected from the group consisting of Trp, Phe and Leu; $Glu_1$ is any amino acid; Val is an amino acid selected from the group consisting of Val and Ile; Leu is an amino acid selected from the group consisting of Leu, Ile, Met, Val and Ala;$Trp_2$ is amino acid selected from the group consisting of Trp, Phe, Tyr, Leu and Met; $Thr_1$ is any amino acid; $Trp_3$ is an amino acid selected from the group consisting of Trp, Phe and Tyr; $Glu_2$ is any amino acid; $Thr_2$ is any amino acid; $Glu_3$ is any amino acid and Arg is an amino acid selected from the group consisting of Arg, Lys, Leu and Trp.

The foregoing peptides preferably have an $IC_{50}$ for FVII/FVIIa of less than 1 μM, more preferably less than 100 nM and more preferably less than 10 nM. In addition the peptides preferably binds FVII/FVIIa and inhibits activity associated with FVIIa selected from the group consisting of activation of FVII, activation of FIX and activation of FX. Preferably the peptide competes with a peptide of the present invention for binding FVII/FVIIa and blocks activation of FX. Preferably the peptide has an $IC_{50}$ for inhibiting FX activation of less than 10 μM, more preferably of less than 100 nM and more preferably less than 5 nM.

In this context reference can be made to the exemplary peptides listed in FIG. 10 (SEQ ID NOS:2–39).

Methods of Use

The invention further provides a method of inhibiting FVIIa activity comprising the step of contacting FVII/FVIIa with a peptide of the invention, such as those described above, in the presence of tissue factor and under conditions which allow binding of the compound to FVIIa to occur.

The invention also provides a method for selecting a compound which blocks FVII/FVIIa activation of FX comprising the step of:

(1) contacting FVII/FVIIa with a peptide compound of the invention in the presence and absence of a candidate compound under conditions which allow specific binding of the peptide compound of the invention to FVII/FVIIa to occur;

(2) detecting the amount of specific binding of the peptide compound of the invention to FVII/FVIIa that occurs in the presence and absence of the candidate compound; and (3) selecting a candidate compound based upon a decrease in the amount of binding of the peptide compound of the invention in the presence of the candidate compound.

The invention further provides a method of inhibiting the activation of FX comprising contacting FVII/FVIIa with a compound that prevents the interaction of FVII/FVIIa with a peptide of the invention. The contacting step may occur in vivo or in vitro.

Chemical Synthesis

One method of producing the compounds of the invention involves chemical synthesis. This can be accomplished by using methodologies well known in the art (see Kelley, R. F., and Winkler, M. E., in *Genetic Engineering Principles and Methods*, Setlow, J. K, ed., vol. 12, pp. 1–19 (Plenum Press, New York, N.Y., 1990); Stewart, J. M., and Young, J. D., *Solid Phase Peptide Synthesis* (Pierce Chemical Co., Rockford, Ill., 1984); see also U.S. Pat. Nos. 4,105,603; 3,972,859; 3,842,067; and 3,862,925).

Figure 2:
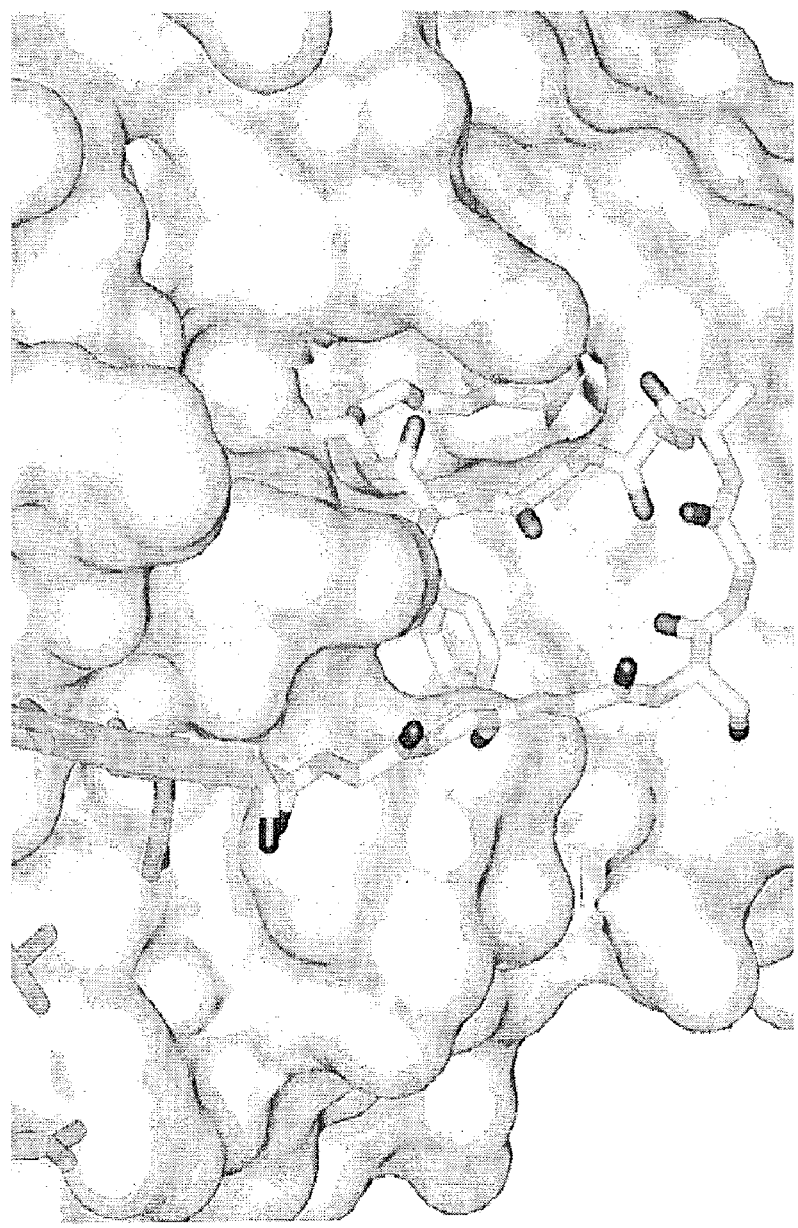
FIG. 2. Model of FVIIa protease domain with A-183 extension peptide. The protease domain of FVIIa is depicted as a model complexed with peptide A-183 having a C-terminal extension. The model shows peptide A-183 linked to the sequence SGGGSGASGFR (SEQ ID NO: 1), where the C-terminal arginine is in the P1 pocket at the active site. The phenylalanine was chosen in analogy to the irreversible active site inhibitor (D-Phe-L-Phe-Arg-CMK) used in the crystal structure of the TF-FVIIa complex (Banner, D. W., et al., (1996) Nature, 380: 41–46).

Peptides of the invention can be conveniently prepared using solid phase peptide synthesis (Merrifield, *J. Am. Chem. Soc.* 85:2149 (1964); Houghten, *Proc. Natl. Acad. Sci. USA* 82:5132 (1985)). Solid phase synthesis begins at the carboxyl terminus of the putative peptide by coupling a protected amino acid to an inert solid support. The inert solid support can be any macromolecule capable of serving as an anchor for the C-terminus of the initial amino acid. Typically, the macromolecular support is a cross-linked polymeric resin (e.g., a polyamide or polystyrene resin), as shown in FIGS. 1-1 and 1-2, on pages 2 and 4 of Stewart and Young, supra. In one embodiment, the C-terminal amino acid is coupled to a polystyrene resin to form a benzyl ester. A macromolecular support is selected such that the peptide anchor link is stable under the conditions used to deprotect the α-amino group of the blocked amino acids in peptide synthesis. If a base-labile α-protecting group is used, then it is desirable to use an acid-labile link between the peptide and the solid support. For example, an acid-labile ether resin is effective for base-labile Fmoc-amino acid peptide synthesis, as described on page 16 of Stewart and Young, supra. Alternatively, a peptide anchor link and α-protecting group that are differentially labile to acidolysis can be used. For example, an aminomethyl resin such as the phenylacetamidomethyl (Pam) resin works well in conjunction with Boc-amino acid peptide synthesis, as described on pages 11–12 of Stewart and Young, supra.

After the initial amino acid is coupled to an inert solid support, the α-amino protecting group of the initial amino acid is removed with, for example, trifluoroacetic acid (TFA) in methylene chloride and neutralizing in, for example, triethylamine (TEA). Following deprotection of the initial amino acid's α-amino group, the next α-amino and sidechain protected amino acid in the synthesis is added. The remaining α-amino and, if necessary, side chain protected amino acids are then coupled sequentially in the desired order by condensation to obtain an intermediate compound connected to the solid support. Alternatively, some amino acids may be coupled to one another to form a fragment of the desired peptide followed by addition of the peptide fragment to the growing solid phase peptide chain.

The condensation reaction between two amino acids, or an amino acid and a peptide, or a peptide and a peptide can be carried out according to the usual condensation methods such as the axide method, mixed acid anhydride method, DCC (N,N'-dicyclohexylcarbodiimide) or DIC (N,N'-diisopropylcarbodiimide) methods, active ester method, p-nitrophenyl ester method, BOP (benzotriazole-1-yl-oxy-tris [dimethylamino] phosphonium hexafluorophosphate) method, N-hydroxysuccinic acid imido ester method, etc, and Woodward reagent K method.

It is common in the chemical syntheses of peptides to protect any reactive side-chain groups of the amino acids with suitable protecting groups. Ultimately, these protecting groups are removed after the desired polypeptide chain has been sequentially assembled. Also common is the protection of the α-amino group on an amino acid or peptide fragment while the C-terminal carboxyl group of the amino acid or peptide fragment reacts with the free N-terminal amino group of the growing solid phase polypeptide chain, followed by the selective removal of the α-amino group to permit the addition of the next amino acid or peptide fragment to the solid phase polypeptide chain. Accordingly, it is common in polypeptide synthesis that an intermediate compound is produced which contains each of the amino acid residues located in the desired sequence in the peptide chain wherein individual residues still carry side-chain protecting groups. These protecting groups can be removed substantially at the same time to produce the desired polypeptide product following removal from the solid phase.

αα- and ε-amino side chains can be protected with benzyloxycarbonyl (abbreviated Z), isonicotinyloxycarbonyl (iNOC), o-chlorobenzyloxycarbonyl [Z(2Cl)], p-nitrobenzyloxycarbonyl [Z(NO$_2$)], p-methoxybenzyloxycarbonyl [Z(OMe)], t-butoxycarbonyl (Boc), t-amyloxycarbonyl (Aoc), isobornyloxycarbonyl, adamantyloxycarbonyl, 2-(4-biphenyl)-2-propyloxycarbonyl (Bpoc), 9-fluorenylmethoxycarbonyl (Fmoc), methylsulfonyethoxycarbonyl (Msc), trifluoroacetyl, phthalyl, formyl, 2-nitrophenylsulphenyl (NPS), diphenylphosphinothioyl (Ppt), and dimethylphosphinothioyl (Mpt) groups, and the like.

Protective groups for the carboxyl functional group are exemplified by benzyl ester (OBzl), cyclohexyl ester (Chx), 4-nitrobenzyl ester (ONb), t-butyl ester (Obut), 4-pyridylmethyl ester (OPic), and the like. It is often desirable that specific amino acids such as arginine, cysteine, and serine possessing a functional group other than amino and carboxyl groups are protected by a suitable protective group. For example, the guanidino group of arginine may be protected with nitro, p-toluenesulfonyl, benzyloxycarbonyl, adamantyloxycarbonyl, p-methoxybenzesulfonyl, 4-methoxy-2,6-dimethylbenzenesulfonyl (Nds), 1,3,5-trimethylphenysulfonyl (Mts), and the like. The thiol group of cysteine can be protected with p-methoxybenzyl, trityl, and the like.

Many of the blocked amino acids described above can be obtained from commercial sources such as Novabiochem (San Diego, Calif.), Bachem C A (Torrence, Calif.) or Peninsula Labs (Belmont, Calif.).

Stewart and Young, supra, provides detailed information regarding procedures for preparing peptides. Protection of α-amino groups is described on pages 14–18, and side chain blockage is described on pages 18–28. A table of protecting groups for amine, hydroxyl and sulfhydryl functions is provided on pages 149–151.

After the desired amino acid sequence has been completed, the peptide can be cleaved away from the solid support, recovered and purified. The peptide is removed from the solid support by a reagent capable of disrupting the peptide-solid phase link, and optionally deprotects blocked side chain functional groups on the peptide. In one embodiment, the peptide is cleaved away from the solid phase by acidolysis with liquid hydrofluoric acid (HF), which also removes any remaining side chain protective groups. Preferably, in order to avoid alkylation of residues in the peptide (for example, alkylation of methionine, cysteine, and tyrosine residues), the acidolysis reaction mixture contains thio-cresol and cresol scavengers. Following HF cleavage, the resin is washed with ether, and the free peptide is extracted from the solid phase with sequential washes of acetic acid solutions. The combined washes are lyophilized, and the peptide is purified.

Disulfide Linked Peptides

Some embodiments of the invention include cyclic peptides formed by a disulfide bond between cysteine residues. Such peptides can be made by chemical synthesis as described above and then cyclized by any convenient method used in the formation of disulfide linkages. For example, peptides can be recovered from solid-phase synthesis with sulfhydryls in reduced form, dissolved in a dilute solution wherein the intramolecular cysteine concentration exceeds the intermolecular cysteine concentration in order to optimize intramolecular disulfide bond formation, such as a peptide concentration of 25 mM to 1 μM, and more preferably 500 μM to 1 μM, and more preferably 25 μM to 1 μM, and then oxidized by exposing the free sulfhydryl groups to a mild oxidizing agent that is sufficient to generate intramolecular disulfide bonds, e.g., molecular oxygen with or without catalysts such as metal cations, potassium ferricyanide, sodium tetrathionate, etc. The peptides can be cyclized as described in Pelton et al., J. Med. Chem. 29:2370–2375 (1986).

Cyclization can be achieved by the formation, for example, of a disulfide bond or a lactam bond between Cys residues. Residues capable of forming a disulfide bond include for example Cys, Pen, Mpr, and Mpp and its 2-amino group-containing equivalents. Residues capable of forming a lactam bridge include, for example, Asp, Glu, Lys, Orn, -diaminobutyric acid, diaminoacetic acid, aminobenzoic acid and mercaptobenzoic acid. The compounds herein can be cyclized, for example, via a lactam bond which can utilize the side chain group of a non-adjacent residue to form a covalent attachment to the N-terminus amino group of Cys or other amino acid. Alternative bridge structures also can be used to cyclize the compounds of the invention, including, for example, peptides and peptidomimetics, which can cyclize via S—S, $CH_2$—S, $CH_2$—O—$CH_2$, lactam ester or other linkages.

Recombinant Synthesis

In a further embodiment, the present invention encompasses a composition of matter comprising isolated nucleic acid, preferably DNA, encoding a peptide described herein. DNAs encoding the peptides of the invention can be prepared by a variety of methods known in the art. These methods include, but are not limited to, chemical synthesis by any of the methods described in Engels et al.,*Agnew. Chem. Int. Ed. Engl.* 28:716–734 (1989), the entire disclosure of which is incorporated herein by reference, such as the triester, phosphite, phosphoramidite and H-phosphonate methods. In one embodiment, codons preferred by the expression host cell are used in the design of the encoding DNA. Alternatively, DNA encoding the peptide can be altered to encode one or more variants by using recombinant DNA techniques, such as site-specific mutagenesis (Kunkel et al., *Methods Enzymol.* 204:125–139 (1991); Carter, P., et al., *Nucl. Acids. Res.* 13:4331 (1986); Zoller, M. J., et al., *Nucl. Acids Res.* 10:6487 (1982)), cassette mutagenesis (Wells, J. A., et al., *Gene* 34:315 (1985)), restriction selection mutagenesis (Wells, J. A., et al., *Philos. Trans, R. Soc. London,* SerA 317, 415), and the like.

The invention further comprises an expression control sequence operably linked to the DNA molecule encoding a peptide of the invention, and an expression vector, such as a plasmid, comprising the DNA molecule, wherein the control sequence is recognized by a host cell transformed with the vector. In general, plasmid vectors contain replication and control sequences which are derived from species compatible with the host cell. The vector ordinarily carries a replication site, as well as sequences which encode proteins that are capable of providing phenotypic selection in transformed cells.

Suitable host cells for expressing the DNA include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC No. 31,446); *E. coli* X1776 (ATCC No. 31,537); *E. coli* strain W3110 (ATCC No. 27,325) and K5 772 (ATCC No. 53,635).

In addition to prokaryotes, eukaryotic organisms, such as yeasts, or cells derived from multicellular organisms can be used as host cells. For expression in yeast host cells, such as common baker's yeast or *Saccharomyces cerevisiae*, suitable vectors include episomally replicating vectors based on the 2-micron plasmid, integration vectors, and yeast artificial chromosome (YAC) vectors. Suitable host cells for expression also are derived from multicellular organisms. Examples of invertebrate cells include insect cells such as Drosophila S2 and Spodoptera Sf9, as well as plant cells. For expression in insect host cells, such as Sf9 cells, suitable vectors include baculoviral vectors. For expression in plant host cells, particularly dicotyledonous plant hosts, such as tobacco, suitable expression vectors include vectors derived from the Ti plasmid of *Agrobacterium tumefaciens*.

Examples of useful mammalian host cells include monkey kidney CV1 line transformed by SV40 (COS-7, ATCC CRL 1651); human embryonic kidney line (293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub and Chasin, *Proc. Natl. Acad. Sci. USA* 77:4216 (1980)); mouse sertoli cells (TM4, Mather, *Biol. Reprod.* 23:243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44–68 (1982)); MRC 5 cells; FS4 cells; and a human hepatoma cell line (Hep G2).

For expression in prokaryotic hosts, suitable vectors include pBR322 (ATCC No. 37,017), phGH107 (ATCC No. 40,011), pBO475, pS0132, pRIT5, any vector in the pRIT20 or pRIT30 series (Nilsson and Abrahmsen, *Meth. Enzymol.* 185:144–161 (1990)), pRIT2T, pKK233-2, pDR540 and pPL-lambda. Prokaryotic host cells containing the expression vectors of the present invention include *E. coli* K12 strain 294 (ATCC NO. 31,446), *E. coli* strain JM101 (Messing et al., *Nucl. Acid Res.* 9:309 (1981)), *E. coli* strain B, *E. coli* strain $_x$1776 (ATCC No. 31,537), *E. coli* c600 (Appleyard, Genetics 39:440 (1954)), *E. coli* W3110 (F-, gamma-, prototrophic, ATCC No. 27,325), *E. coli* strain 27C7 (W3110, tonA, phoA E15, (argF-lac)169, ptr3, degP41, ompT, kan$^r$) (U.S. Pat. No. 5,288,931, ATCC No. 55,244), *Bacillus subtilis, Salmonella typhimurium, Serratia marcesans,* and *Pseudomonas* species.

For expression in mammalian host cells, useful vectors include vectors derived from SV40, vectors derived from cytomegalovirus such as the pRK vectors, including pRK5 and pRK7 (Suva et al., *Science* 237:893–896 (1987); EP 307,247 (Mar. 15, 1989), EP 278,776 (Aug. 17, 1988)) vectors derived from vaccinia viruses or other pox viruses, and retroviral vectors such as vectors derived from Moloney's murine leukemia virus (MoMLV).

Optionally, the DNA encoding the peptide of interest is operably linked to a secretory leader sequence resulting in secretion of the expression product by the host cell into the culture medium. Examples of secretory leader sequences include stII, ecotin, lamB, herpes GD, lpp, alkaline phosphatase, invertase, MIP.5 and alpha factor. Also suitable for use herein is the 36 amino acid leader sequence of protein A (Abrahmsen et al., *EMBO J.* 4:3901 (1985)).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending upon the host cell used, transformation is done using standard techniques appropriate to such cells. The calcium treatment employing calcium chloride, as described in section 1.82 of Sambrook et al., *Molecular Cloning*, 2nd ed. (Cold Spring Harbor Laboratory, New York, 1989), is generally used for prokaryotes or other cells that contain substantial cell-wall barriers. Infection with *Agrobacterium tumefaciens* is used for transformation of certain plant cells, as described by Shaw et al., *Gene* 23:315 (1983) and WO 89/05859, published 29 Jun. 1989. For mammalian cells without such cell walls, the calcium phosphate precipitation method described in sections 16.30–16.37 of Sambrook et al., supra, is preferred. General aspects of mammalian cell host system transformations have been described by Axel in U.S. Pat. No. 4,399,216, issued 16 Aug. 1983. Transformations into yeast are typically carried out according to the method of Van Solingen et al., *J. Bact.* 130:946 (1977) and Hsiao et al., *Proc. Natl. Acad. Sci. USA* 76:3829 (1979). However, other methods for introducing DNA into cells such as by nuclear injection, electroporation, or by protoplast fusion may also be used.

Other preferred vectors can be constructed using standard techniques by combining the relevant traits of the vectors described above. Relevant traits include the promoter, the ribosome binding site, the gene of interest or gene fusion (the Z domain of protein A and gene of interest and a linker), the antibiotic resistance markers, and the appropriate origins of replication.

A variation on the above procedures contemplates the use of gene fusions, wherein the gene encoding the desired peptide is associated, in the vector, with a gene encoding another protein or a fragment of another protein. This results in the desired peptide being produced by the host cell as a fusion with another protein or peptide. The "other" protein or peptide is often a protein or peptide which can be secreted by the cell, making it possible to isolate and purify the desired peptide from the culture medium and eliminating the necessity of destroying the host cells which arises when the desired peptide remains inside the cell. Alternatively, the fusion protein can be expressed intracellularly. It is useful to use fusion proteins that are highly expressed.

The use of gene fusions, though not essential, can facilitate the expression of heterologous peptides in insect cells as well as the subsequent purification of those gene products. Protein A fusions are often used because the binding of protein A, or more specifically the Z domain of protein A, to IgG provides an "affinity handle" for the purification of the fused protein. For example, a DNA sequence encoding the desired peptide ligand can be fused by site-directed mutagenesis to the genen for a consensus domain of protein A known as the Z domain (Nilsson et al., *Protein Engineering* 1:107–113 (1987)). After expression and secretion the fusion protein can be enzymatically cleaved to yield free peptide which can be purified from the enzymatic mix (see, e.g., Varadarajan et al., *Proc. Natl. Acad. Sci USA* 82:5681–5684 (1985); Castellanos-Serra et al., FEBS Letters 378:171–176 (1996); Nilsson et al., *J. Biotechnol.* 48:241–250 (1996)).

Fusion proteins can be cleaved using chemicals, such as cyanogen bromide, which cleaves at a methionine, or hydroxylamine, which cleaves between an Asn and Gly residue. Using standard recombinant DNA methodology, the nucleotide base pairs encoding these amino acids may be inserted just prior to the 5' end of the gene encoding the desired peptide.

Alternatively, one can employ proteolytic cleavage of fusion protein. Carter, in *Protein Purification: From Molecular Mechanisms to Large-Scale Processes*, Ladisch et al., eds., Ch. 13, pp. 181–193 (American Chemical Society Symposium Series No. 427, 1990).

Proteases such as enterokinase, Factor Xa, thrombin, and subtilisin or its mutants, and a number of others have been successfully used to cleave fusion proteins. Preferred according to the present invention for the production of peptide ligands of less than about 30 amino acids is the protease trypsin which is highly specific for Arg and Lys residues. Trypsin cleavage is discussed generally in Nilsson et al., *J. Biotech.* 48:241 (1996) and Smith et al., *Methods Mol. Biol.* 32:289 (1994). Typically, a peptide linker that is amenable to cleavage by the protease used is inserted between the "other" protein (e.g., the Z domain of protein A) and the desired peptide. Using recombinant DNA methodology, the nucleotide base pairs encoding the linker are inserted between the genes or gene fragments coding for the other proteins. Proteolytic cleavage of the partially purified fusion protein containing the correct linker can then be carried out on either the native fusion protein, or the reduced or denatured fusion protein.

The peptide may or may not be properly folded when expressed as a fusion protein. Also, the specific peptide linker containing the cleavage site may or may not be accessible to the protease. These factors determine whether the fusion protein must be denatured and refolded, and if so, whether these procedures are employed before or after cleavage.

When denaturing and refolding are needed, typically the peptide is treated with a chaotrope, such a guanidine HCl, and is then treated with a redox buffer, containing, for example, reduced and oxidized dithiothreitol or glutathione at the appropriate ratios, pH, and temperature, such that the peptide is refolded to its native structure.

The host cells referred to in this disclosure encompass cells in in vitro culture as well as cells that are within a host animal.

In cyclized embodiments of the invention, the recombinantly produced peptide can be cyclized by formation of an intramolecular disulfide bond as described above.

The peptide compounds of the invention can be modified at the N-terminus or the C-terminus using an amino-protecting group or carboxyl-protecting group, respectively. Numerous such modifications will be apparent to those skilled in the art. For example, the N-terminus of a peptide or peptide analog can be chemically modified such that the N-terminal amino group is substituted for example by an acetyl, cyclopentylcarboxy, isoquinolylcarboxy, furoyl, tosyl, pyrazinecarboxy, or other such group, which can be sustituted by a substituent as described herein. The N-terminal amino group also can be substituted, for example, with a reverse amide bond. It should be recognized that the term amino group is used broadly herein to refer to any free amino group, including a primary, secondary, or tertiary amino group, present in a peptide. By contrast the term N-terminus refers to the α-amino group of the first amino acid present in a peptide written in the conventional manner.

The N-terminus of a peptide of the invention can be protected by linking thereto an amino protecting group. The term "amino protecting group" is used broadly herein to refer to a chemical group that can react with a free amino group, including, for example, the α-amino group present at the N-terminus of an peptide of the invention. By virtue of reacting therewith, an amino protecting group protects the otherwise reactive amino group against undesirable reactions, as can occur, for example, during a synthetic procedure or due to exopeptidase activity on a final compound.

Modification of an amino group also can provide additional advantages, including, for example, increasing the solubility or the activity of the compound. Compounds having these modifications are meant to be included within the compounds of the present invention since their construction is within the ability of the skilled artisan given the present disclosure. Various amino protecting groups are known in the art and include, for example, acyl groups such as an acetyl, picolyl, tert-butylacetyl, tert-butyloxycarbonyl, benzyloxycarbonyl, benzoyl groups, including for example a benzyloxime such as a 2-aryl-2-o-benzyloxime as well as an amino acyl residue which itself can be modified by an amino-protecting group. Other amino-protecting groups are described, for example, in *The Peptides*, Gross and Meienhofer, eds., Vol. 3 (Academic Press, Inc., New York, N.Y., 1981) and Greene and Wuts, in *Protective groups in Organic Synthesis*, 2d ed., pp. 309–405 (John Wiley & sons, New York, N.Y., 1991), each of which is incorporated herein by reference. The product of any such modification of the N-terminus amino group of a peptide or peptide analog of the invention is referred to herein as an "N-terminal derivative".

Similarly, a carboxyl group such as the carboxyl group present at the C-terminus of a peptide can be chemically modified using a carboxyl-protecting group. The terms "carboxyl group" and "C-terminus" are used in a manner consistent with the terms amino groups and N-terminus as defined above. A carboxyl group such as that present at the C-terminus of a peptide can be modified by reduction of the C-terminal carboxyl group to an alcohol or aldehyde or by formation of an oral ester or by substitution of the carboxyl group with a substituent such as a thiazolyl, cyclohexyl, or other group. Oral esters are well known in the art and include, for example, alkoxymethyl groups such as methoxymethyl, ethoxymethyl, propoxymethyl, isopropoxymethyl, and the like.

Research and Diagnostic Compositions

In a preferred embodiment, the peptides of the invention are non-covalently adsorbed or covalently bound to a macromolecule, such as a solid support. It will be appreciated that the invention encompasses both macromolecules complexed with the peptides. In general, the solid support is an inert matrix, such as a polymeric gel, comprising a three-dimensional structure, lattice or network of a material. Almost any macromolecule, synthetic or natural, can form a gel in a suitable liquid when suitably cross-linked with a bifunctional reagent. Preferably, the macromolecule selected is convenient for use in affinity chromatography. Most chromatographic matrices used for affinity chromatography are xerogels. Such gels shrink on drying to a compact solid comprising only the gel matrix. When the dried xerogel is resuspended in the liquid, the gel matrix imbibes liquid, swells and returns to the gel state. Xerogels suitable for use herein include polymeric gels, such as cellulose, cross-linked dextrans (e.g., Sepharose), agarose, cross-linked agarose, polyacrylamide gels, and polyacrylamide-agarose gels.

Alternatively, aerogels can be used for affinity chromatography. These gels do not shrink on drying but merely allow penetration of the surrounding air. When the dry gel is exposed to liquid, the latter displaces the air in the gel. Aerogels suitable for use herein include porous glass and ceramic gels.

Also encompassed herein are the peptides of the invention coupled to derivatized gels wherein the derivative moieties facilitate the coupling of the peptide ligands to the gel matrix and avoid steric hindrance of the peptide-FVII/FVIIa interaction in affinity chromatography. Alternatively, spacer arms can be interposed between the gel matrix and the peptide ligand for similar benefits.

Pharmaceutical Compositions

Pharmaceutical compositions which comprise the compounds of the invention, including the hybrid molecules of the invention, may be formulated and delivered or administered in a manner best suited to the particular FVII/FVIIa mediated disease or disorder being treated, including formulations suitable for parental, topical, oral, local, aerosol or transdermal administration or delivery of the compounds. In indications where the reduction of TF-FVIIa dependent coagulation is related to circulation of blood through stents or artificial valves or related to extracorporeal circulation, including blood removed in-line from a patient in such processes as dialysis procedures, blood filtration, or blood bypass during surgery, suitable formulations include those appropriate for coating devices such as stents, valves and filtration devices.

Somewhat more particularly, suitable compositions of the present invention comprise any of the compounds described herein along with a pharmaceutically acceptable carrier, the nature of the carrier differing with the mode of administration delivery or use, for example, in oral administration, usually using a solid carrier and in i.v. administration, a liquid salt solution carrier. For local administration, such as may be appropriate where TF-FVIIa dependent coagulation is related to circulation of blood through artificial devices such as stents or valves, the peptides may be linked, for example, covalently, to the artificial device preventing local thrombus formation. Alternatively, the peptide may be provided in a formulation that would allow for the peptide to slowly elute from the device providing both local and systemic protection against events associated with TF-FVIIa dependent coagulation. As but one example, stents adsorbed with peptides can be employed following angioplasty or other surgical procedure.

The compositions of the present invention include pharmaceutically acceptable components that are compatible with the subject and the compound of the invention. These generally include suspensions, solutions and elixirs, and most especially biological buffers, such as phosphate buffered saline, saline, Dulbecco's Media, and the like. Aerosols may also be used, or carriers such as starches, sugars, microcrystalline cellulose, diluents, granulating agents, lubricants, binders, disintegrating agents, and the like (in the case of oral solid preparations, such as powders, capsules, and tablets).

As used herein, the term "pharmaceutically acceptable" generally means approved by a regulatory agency of the Federal or a state government or listed in the U.S. Pharmacopeia or other generally recognized pharmacopeia for use in animals, and more particularly in humans.

The formulation of choice can be made using a variety of the aforementioned buffers, or even excipients including, for example, pharmaceutical grades of mannitol, lactose, starch, magnesium stearate, sodium saccharin cellulose, magnesium carbonate, and the like. "PEGylation" of the compositions may be achieved using techniques known to the art (see for example International Patent Publication No. W092/16555, U.S. Pat. No. 5,122,614 to Enzon, and International Patent Publication No. W092/00748).

A preferred route of administration of the present invention is in the aerosol or inhaled form. The compounds of the present invention, combined with a dispersing agent, or dispersant, can be administered in an aerosol formulation as a dry powder or in a solution or suspension with a diluent.

As used herein, the term "dispersant" refers to a agent that assists aerosolization of the compound or absorption of the protein in lung tissue, or both. Preferably the dispersant is pharmaceutically acceptable. As used herein, the term "pharmaceutically acceptable" means approved by a regulatory agency of the Federal or a state government or listed in the U.S. Pharmacopeia or other generally recognized pharmacopeia for use in animals, and more particularly in humans. Suitable dispersing agents are well known in the art, and include, but are not limited to, surfactants and the like. For example, surfactants that are generally used in the art to reduce surface-induced aggregation of the compound, especially the peptide compound, caused by atomization of the solution forming the liquid aerosol may be used. Nonlimiting examples of such surfactants include polyoxyethylene fatty acid esters and alcohols, and polyoxyethylene sorbitan fatty acid esters. Amounts of surfactants used will vary, being generally within the range of 0.001 and 4% by weight of the formulation. In a specific aspect, the surfactant is polyoxyethylene sorbitan monooleate or sorbitan trioleate. Suitable surfactants are well known in the art, and can be selected on the basis of desired properties, depending upon the specific formulation, concentration of the compound, diluent (in a liquid formulation) or form of powder (in a dry powder formulation), etc.

Moreover, depending upon the choice of the compound, the desired therapeutic effect, the quality of the lung tissue (e.g., diseased or healthy lungs), and numerous other factors, the liquid or dry formulations can comprise additional components, as discussed further below.

The liquid aerosol formulations generally contain the compound and a dispersing agent in a physiologically acceptable diluent. The dry powder aerosol formulations of the present invention consist of a finely divided solid form of the compound and a dispersing agent. With either the liquid or dry powder aerosol formulation, the formulation must be aerosolized. That is, it must be broken down into liquid or solid particles in order to ensure that the aerosolized dose actually reaches the alveoli. In general, the mass median dynamic diameter will be 5 micrometers or less in order to ensure that the drug particles reach the lung alveoli (Wearley, L. L., *Crit. Rev. in Ther. Drug Carrier Systems* 8:333 (1991)). The term "aerosol particle" is used herein to describe the liquid or solid particle suitable for pulmonary administration, i.e., that will reach the alveoli. Other considerations such as construction of the delivery device, additional components in the formulation, and particle characteristics are important. These aspects of pulmonary administration of a drug are well known in the art, and manipulation of formulations, aerosolization means and construction of a delivery device require, at most, routine experimentation by one of ordinary skill in the art.

With regard to construction of the delivery device, any form of aerosolization known in the art, including, but not limited to, nebulization, atomization or pump aerosolization of a liquid formulation, and aerosolization of a dry powder formulation, can be used in the practice of the invention. A delivery device that is uniquely designed for administration of solid formulations is envisioned. Often, the aerosolization of a liquid or a dry powder formulation will require a propellent. The propellent may be any propellant generally used in the art. Specific nonlimiting examples of such useful propellants are a chlorofluorocarbon, a hydrofluorocarbon, a hydrochlorofluorocarbon, or a hydrocarbon, including trifluoromethane, dichlorodifluoromethane, dichlorotetrafluoroethanol, and 1,1,1,2-tetrafluoroethane, or combinations thereof.

In a preferred aspect of the invention, the device for aerosolization is a metered dose inhaler. A metered dose inhaler provides a specific dosage when administered, rather than a variable dose depending upon administration. Such a metered dose inhaler can be used with either a liquid or a dry powder aerosol formulation. Metered dose inhalers are well known in the art.

Once the compound reaches the lung, a number of formulation-dependent factors effect the drug absorption. It will be appreciated that in treating a disease or disorder that requires circulatory levels of the compound, such factors as aerosol particle size, aerosol particle shape, the presence or absence of infection, lung disease or emboli may affect the absorption of the compounds. For each of the formulations described herein, certain lubricators, absorption enhancers, protein stabilizers or suspending agents may be appropriate. The choice of these additional agents will vary depending upon the goal. It will be appreciated that in instances where local delivery of the compounds is desired or sought, such variables as absorption enhancement will be less critical.

Liquid Aerosol Formulations

The liquid aerosol formulations of the present invention will typically be used with a nebulizer. The nebulizer can be either compressed-air driven or ultrasonic. Any nebulizer known in the art can be used in conjunction with the present invention, such as, but not limited to: Ultravent, (Mallinckrodt, Inc., St. Louis, Mo.); the Acorn II nebulizer (Marquest Medical Products, Englewood Colo.). Other nebulizers useful in conjunction with the present invention are described in U.S. Pat. Nos. 4,624,251, issued Nov. 25, 1986; U.S. Pat. No. 3,703,173, issued Nov. 21, 1972; U.S. Pat. No. 3,561,444, issued Feb. 9, 1971; and U.S. Pat. No. 4,635,627, issued Jan. 13, 1971.

The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include, but are not limited to, Soya lecithin, oleic acid and sorbitan trioleate, with sorbitan trioleate preferred.

The formulations of the present embodiment may also include other agents useful for protein stabilization or for the regulation of osmotic pressure. Examples of the agents include, but are not limited to, salts, such as sodium chloride, or potassium chloride, and carbohydrates, such as glucose, galactose or mannose, and the like.

Aerosol Dry Powder Formulations

It is also contemplated that the present pharmaceutical formulation will be used as a dry powder inhaler formulation comprising a finely divided powder form of the compound and a dispersant. The form of the compound will generally be a lyophilized powder. Lyophilized forms of peptide compounds can be obtained through standard techniques.

In another embodiment, the dry powder formulation will comprise a finely divided dry powder containing one or more compounds of the present invention, a dispersing agent and also a bulking agent. Bulking agents useful in conjunction with the present formulation include such agents as lactose, sorbitol, sucrose, or mannitol, in amounts that facilitate the dispersal of the powder from the device.

Therapeutic Methods

The compounds of the present invention can be used therapeutically to prevent the biological activity of the TF-FVIIa complex. The inhibition of TF-FVIIa is desirable in indications where the reduction of TF-FVIIa dependent coagulation is implicated. These situations include but are not limited to the prevention of arterial thrombosis in combination with thrombolytic therapy. It has been suggested that the TF-FVIIa plays a significant role in a variety of clinical states including deep venous thrombosis, arterial thrombosis, stroke, DIC, septic shock, cardiopulmonary bypass surgery, adult respiratory distress syndrome, hereditary angioedema. Inhibitors of TF-FVIIa may therefore play important roles in the regulation of inflammatory and/or thrombotic disorders.

Thus the present invention encompasses a method for preventing TF-FVIIa mediated event in a human comprising administering to a patient in need thereof a therapeutically effective amount of the compound of the present invention. A therapeutically effective amount of the compound of the present invention is predetermined to achieve the desired effect. The amount to be employed therapeutically will vary depending upon therapeutic objectives, the routes of administration and the condition being treated. Accordingly, the dosages to be administered are sufficient to bind to available FVII/FVIIa and form an inactive complex leading to decreased coagulation in the subject being treated.

The therapeutic effectiveness is measured by an improvement in one or more symptoms associated with the TF-FVIIa dependant coagulation. Such therapeutically effective dosages can be determined by the skilled artisan and will vary depending upon the age, sex and condition of the subject being treated. Suitable dosage ranges for systemic administration are typically between about 1 µg/kg to up to 100 mg/kg or more and depend upon the route of administration. According to the present invention, a preferred therapeutic dosage is between about 1 µg/kg body weight and about 5 mg/kg body weight. For example, suitable regimens include intravenous injection or infusion sufficient to maintain concentration in the blood in the ranges specified for the therapy contemplated.

The conditions characterized by abnormal thrombosis include those involving the arterial and venous vasculature. With respect to the coronary arterial vasculature, abnormal thrombus formation characterizes, for example, the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA). With respect to the venous vasculature, abnormal thrombus formation characterizes the condition observed in patients undergoing surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy commonly associated with both vascular systems during septic shock, certain viral infections and cancer, a condition wherein there is a rapid consumption of coagulation factors and systemic coagulation which results in the formation of life-threatening thrombi occurring throughout the microvasculature leading to wide-spread organ failure.

The following examples are offered by way of illustration and not by way of limitation. The disclosures of all citations in the specification are expressly incorporated herein by reference.

EXAMPLES

Example 1

In order to identify peptides of the invention that extend from the FVIIa exosite identified by A-183 into the active site of FVIIa, a substrate phage display approach was utilized. This approach required optimal conditions for specific phage binding under conditions where FVIIa is inactive followed by activation of FVIIa in the presence of bound phage in order to select only those phage that are released due to enzymatic cleavage by FVIIa.

Since A-183 inhibits TF-FVIIa activity, albeit incompletely, special conditions were selected. The amidolytic activity of FVIIa has been studied under a variety of different conditions such as changes in pH, different salts at various concentrations and the effect of TF (Neuenschwander, P. F., et al. (1993). Thromb. Haemostasis, 70: 970–977). In the absence of TF, FVIIa exhibits very low enzymatic activity. Addition of TF enhances the activity for the cleavage of FX by about 1000-fold, whereas the increase in amidolytic activity is ca. 70-fold, depending on the pH (Neuenschwander, P. F., et al. (1993). Thromb. Haemostasis, 70: 970–977). In the absence of TF, FVIIa showed no detectable amidolytic activity at or below pH 6.0 or above pH 10.5. The binding of A-183 to FVIIa also varies as a function of pH, having a determined binding constant of Kd=2.8 nM to FVIIa at pH 7.2 (Roberge, M., et al. (2001) Biochemistry, 40: 9522–9531).

Figure 3:
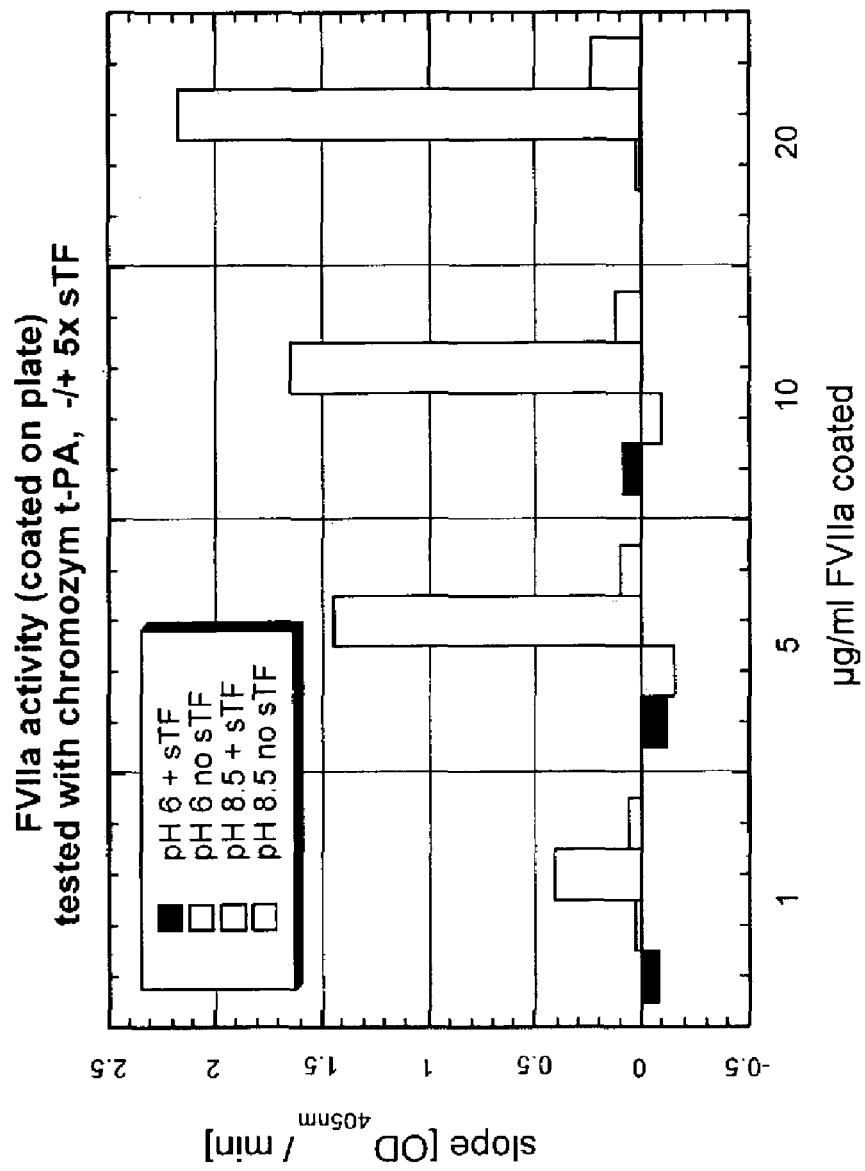
FIG. 3. Amidolytic activity of immoblilized FVIIa. Wells were coated with four different concentrations (1, 5, 10, or 20 µg/ml) of FVIIa. Amidolytic activity was tested with Chromozym t-PA at pH 6.0 and pH 8.5 in the presence and absence of soluble TF (sTF).

The activity of immobilized FVIIa coated on plates was determined and controlled simultaneously. Maxisorp plates were coated with 4 different concentrations of FVIIa (1, 5, 10 and 20 µg). Each concentration was tested in the absence and presence of sTF (soluble TF; $TF_{1-219}$) (Kelley, R. F., et al. (1997) Blood, 89: 3219–3227) at pH 6.0 and pH 8.5. Comparing the activities at the 20 µg FVIIa concentration, the presence of sTF showed an 11-fold increase in activity at pH 8.5, whereas amidolytic actvity was basically undetectable at pH 6.0 and the absence of sTF (FIG. 3). The activity increased with the amount of FVIIa coated on the plate.

As previously described, A-183 shows potent but incomplete inhibition of amidolytic activity (Dennis, M. S., et al. (2001) Biochemistry, 40: 9513–9521). To test whether amidolytic activity was still sufficient in the presence of A-183, we designed a substrate comprising A-183 fused to Z-domain of protein A. This fusion contained a linker with the cleavage sequence of FX (..NLTRIVGG..) where the putative P1 arginine was 11 residues from the C-terminal arginine of A-183. This fusion peptide was incubated with FVIIa in the presence and absence of sTF at pH 6.0 and pH 8.5. The reaction mix was incubated at room temperature for 2 hours and separated by HPLC. Collected peaks were analyzed by SDS-PAGE, N-terminal sequencing and mass spectrometry. This data confirmed that the fusion peptide was cleaved after the putative P1 arginine only under enzymatically favorable conditions (sTF, pH 8.5); no cleavage was observed at pH 6.0 and the absence of sTF the fusion peptide. Based on these studies, suitable conditions for controlling both binding (pH 6.0) and catalysis (sTF, pH 8.5) were determined.

Clotting Assay

The prothrombin time (PT) assay was performed in citrated pooled normal human plasma as described previously (Dennis, M. S., et al., (2000) Nature, 404: 465–470). Clotting times were determined using an ACL 300 Coagulation Analyzer (Coulter Corp., Miami, Fla.) using Innovin (human relipidated TF and Ca2+) from Dade International Inc. to initiate the assay.

Example 2

The crystal structure of the protease domain of FVII in complex with A-183 revealed the orientation of the bound peptide at its binding site (Eigenbrot, C., et al. (2001) Structure, 9: 627–636). FIG. 1 depicts a model based on the crystal structure of peptide A-183 (green) at the A exosite and D-Phe-L-Arg-chloromethylketone (salmon) covalently bound to the active site (Roberge, M. et al., (2001) Biochemistry, 40:9522–9531. The amino and carboxy terminal residues of A-183 are indicated. The C-terminal arginine of A-183 is in close proximity to the protease active site. We modeled a hypothetical extension onto the C-terminus of A-183, attempting to find the shortest path to the active site of FVIIa (FIG. 2). Taking the shape of the surface and the constraints in flexibility due to peptide bonds, an extension of 11 residues was estimated to be sufficient to reach the active site. Substrate phage library design A hexa-His-A183-(protease resistant linker)-g3p fusion was constructed for monovalent display of a A-183-extension peptide library on filamentous phage. The previously described clone AD (Dennis, M. S., et al., (2001) Biochemistry, 40: 9513–9521) was used as a template for Kunkel mutagenesis (Kunkel, T. A, et al., (1987) Methods Enzymol., 154: 367–382) to create a template phagemid containing DNA encoding hexa-His, peptide A-183, 3 stop codons, and the sequence TPTDPPTTPPT (SEQ ID NO:41) (a protease resistant linker), which was fused to the N-terminus of g3. The following primers were used:
(5' TGC TGG ACG TGG GAG ACC TGC GAA CGT GGT GAA GGT CAG TAA TAA TAA ACC CCG ACC GAT CCG CCG ACC ACC CCG CCG ACC GAT TTT GAT TAT3') (SEQ ID NO:42) and (5'-ACA AAT GCC TAT GCA CAT CAC CAT CAC CAT CAC TCC GAA GAG TGG GAG-3') (SEQ ID NO:43).

Four random sequence peptide libraries were constructed based on the template phagemid above, which was used as the template:

hexa-His-A183-XXXXXXXBNLTRIVGG-(protease resistant linker)-g3, library A
hexa-His-A183-XXXXXXXJLTRIVGG-(protease resistant linker)-g3, library B
hexa-His-A183-XXXXXXXUTRIVGG-(protease resistant linker)-g3, library C
hexa-His-A183-GGSGGSGXXXXXXXGG-(protease resistant linker)-g3, library D At positions B, J and U codons were tailored to randomly coding only the residue sets (S,N,K), (N,K) and (L,Q), respectively, whereas at position X all 20 residues were allowed using NNS codons. The oligonucleotides 5'-GAG ACC TGC GAA CGT NNS NNS NNS NNS NNS NNS NNS ARM AAC CTG ACC CGT ATC GTG GGT GGT ACC CCG ACC GAT CCG-3' (SEQ ID NO:44), 5'-GAG ACC TGC GAA CGT NNS NNS NNS NNS NNS NNS NNS AAM CTG ACC CGT ATC GTG GGT GGT ACC CCG ACC GAT CCG-3' (SEQ ID NO:45), 5'-GAG ACC TGC GAA CGT NNS NNS NNS NNS NNS NNS NNS CWG ACC CGT ATC GTG GGT GGT ACC CCG ACC GAT CCG-3' (SEQ ID NO:46) and 5'-GAG ACC TGC GAA CGT GGT GGT AGC GGT GGT AGC GGT NNS NNS NNS NNS NNS NNS NNS GGT GGT ACC CCG ACC GAT CCG-3' (SEQ ID NO:47) were used to generate libraries A, B, C, and D, respectively, which yielded 4.7× $10^{10}$, 3.5×$10^{10}$, 1.5×$10^{10}$, and 1.7×$10^{10}$ E. coli transformanants, respectively. N stands for A, C, G, and T; S stands for G and C; R stands for A and G; M stands for A and C; W stands for A and T.

Next, substrate phage libraries were captured on immobilized FVIIa at pH 6.0. In principle, the change to enzymatically favored conditions (sTF, pH 8.5), should result in the release of only those phage displaying preferred substrate sequences. However, the increase in pH results in a new equilibrium of phage bound, as evidenced by the release of uncleaved phage. In order to overcome this background of uncleaved phage, an N-terminal hexa-His tag was introduced on the A-183 phage libraries. Anti-tetra-His monoclonal antibodies were immobilized to a plate to pull out any uncleaved phage, i.e. those containing both the his tag and the phage, from solution. The cleaved phage, which remained in solution, were then propagated and sorted further for enrichment. Control phage displaying hexa-His-A-183 were captured 1000-fold more selectively by the anti-His antibody compared with phage displaying only A-183. About 2×$10^6$ phage forming units were captured by 500 ng of immobilized antibody, which was determined by propagating a serial dilution of both test phage.

Peptide Library Selection Conditions

Individual wells of Maxi-Sorp plates were separately coated with 100 μl FVIIa (10 μg/ml) and 100 μl Tetra-His monoclonal Antibody (Qiagen, Valencia, Calif.) in 50 mM carbonate buffer pH 9.6 at 4° C. overnight. Wells were blocked for 1 hour with Casein in TBS or Superblock in TBS (Pierce, Rockford, Ill.) at room temperature before each round of panning. FVIIa coated wells were incubated with peptide phage libraries in binding buffer (50 mM MES pH 6.0, 100 mM NaCl, 0.5% BSA and 0.05% Tween 20) for 1 hour. Unbound phage were removed by repetitive washing in binding buffer. Individual wells were immediately treated with 100 μl cleavage buffer (50 mM Tris pH 8.5, 100 mM NaCl, 5 mM CaCl$_2$, 5 mM MgCl$_2$, 0.05% Tween 20, 1% BSA, 100 μg/ml sTF) (Note: sTF stands for soluble TF; TF$_{1-219}$) and incubated for 5 min. The supernatant was removed and incubated with Tetra-His monoclonal Antibody coated wells. After 1 hour, supernatant was removed and phage were propagated in XL-1 Blue cells with VCSM13 helper phage (Stratagene, La Jolla, Calif.). After several rounds of panning, individual clones from each library were picked and sequenced. Enrichment was monitored by titering the number of phage released by FVIIa in cleavage buffer compared to phage released by FVIIa in binding buffer.

FVIIa Control Substrate

Because A-183 inhibits the activity of FVIIa a synthetic substrate was constructed to test whether FVIIa had sufficient activity to cleave the synthetic substrate in the presence of A-183. An expression plasmid was constructed using Kunkel mutagenesis (Kunkel, T. A, et al., (1987) Methods Enzymol., 154: 367–382) by inserting a DNA sequence encoding (GGGSGGSNLTRIVGGSGG) (SEQ ID NO:48) into pA-100-Z (Dennis, M. S., et al., (2001) Biochemistry, 40: 9513–9521) between A-183 and the Z-domain. The A-183-CS-Z-fusion peptide, which contains a FVIIa cleavage site, was expressed and purified as described above for the Z-fusion peptides. 20 μg of A-183-CS-Z-fusion peptide was incubated for 2 hours at room temperature with FVIIa and sTF in a molar ration of 10:1:10, respectively. The reaction mix was separated by reversed-phase HPLC using a water/acetonitrile gradient containing 0.1% TFA. Peaks were collected and analyzed by SDS-PAGE, N-terminal sequencing and MALDI-TOF mass spectrometry.

Figure 5:
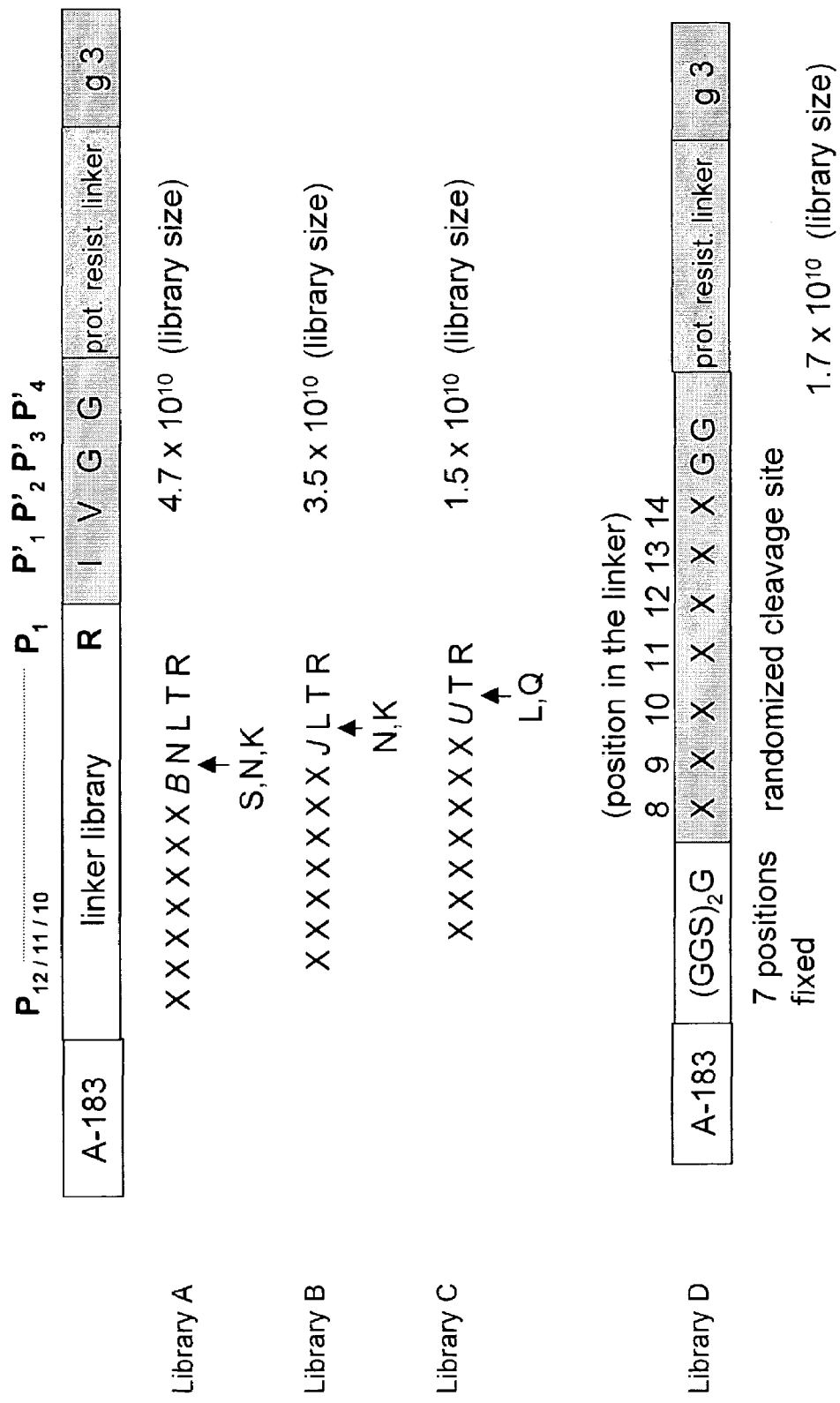
FIG. 5. Library design. Four original libraries designated A, B, C, and D were designed to determine the preferred length and the sequence of the extension which goes into the active site. X refers to any amino acid. . . . P1, P1', P2' . . . refer to the putative . . . P1, P1', P2' . . . residues for serine protease substrates. Cleavage occurs between the P1 and P1' residues. The fixed sequences for libraries A, B, and C are derived from FX, one of the natural protein substrates.
Figure 6:
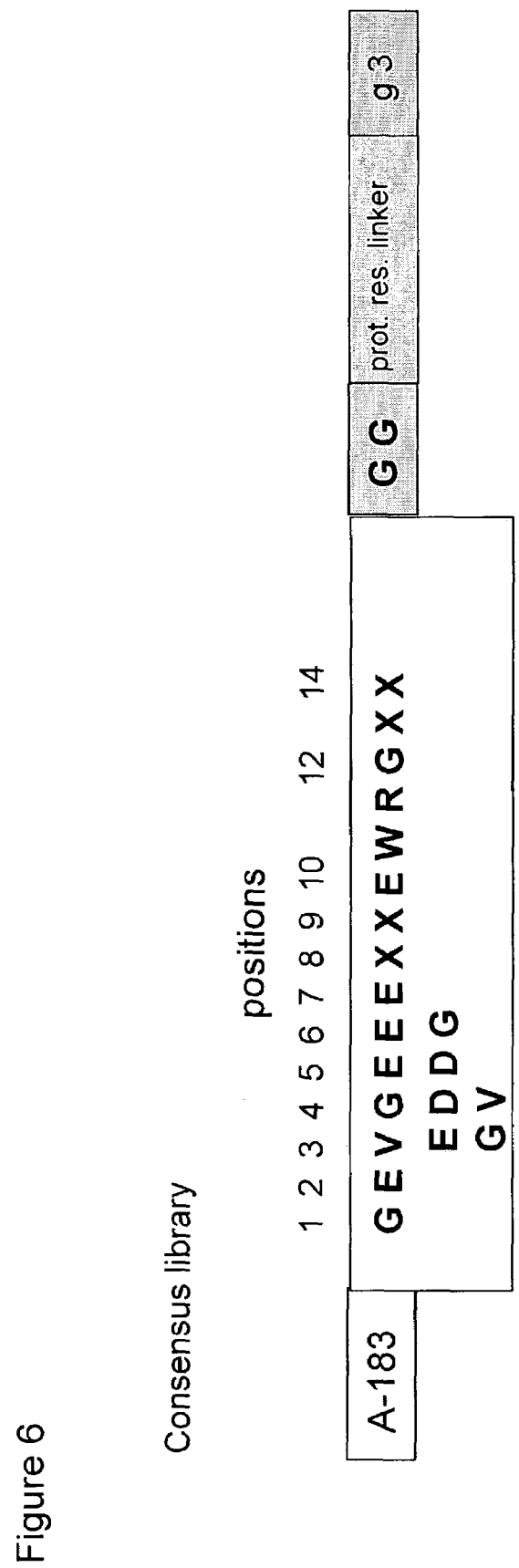
FIG. 6. Consensus Library. A consensus library resulted out of libraries A and D. Residues were either fixed, fally randomized (X) or partially randomized as indicated. The consensus library was sorted to determine the preferred extension of A-183X.

Library Design and Sorting Results 7 positions in the linker were fully randomized at once, which created a theoretical diversity of 6.8×10$^{10}$ variants. Four different libraries were designed to determine the optimal length and sequence of the extension (FIG. 5). Libraries A, B and C contained an arginine at position 10, 11 or 12, respectively, whereas the first 7 residues were fully randomized. The position number refers to the number of residues following the c-terminal arginine of A-183. The residual positions were filled with residues according to those found in the FX cleavage sites of human, bovine and pig. These three libraries were designed to select for preferred residues in the beginning of the linker, considering 3 different positions for the arginine. The linker for Library D contained a flexible (GGS)$_2$G spacer followed by fully randomized residues from positions 8 to 14, addressing the question of which residues are preferred in the cleavage site. In natural and synthetic substrates proteolysis occurs after arginine, defining it as the preferred residue at the P1 position. Thus, the position in which arginine was observed most frequently was used to determine the length of the extension.

After six rounds of sorting, 100 clones were randomly picked from each library and sequenced. A statistical analysis was used to determine the frequency of each residue at any randomized position. The frequencies were normalized by the codon bias to compare the probabilities. In library D, this analysis resulted in the consensus sequence XVEWRGX (SEQ ID NO:49) for positions 8 through 14, respectively, with arginine preferred at position 12, where X represents no clear residue preference. Limiting the statistical analysis for only those sequences containing arginine at position 12 showed consistency in the sequence motif around the arginine (XXEWRGW) (SEQ ID NO:50). These results lead to library A, where arginine was fixed at position 12. Statistical analysis of library A resulted in the consensus sequence GEVGEEE (SEQ ID NO:51) for the first 7 randomized positions, with strong preference for glutamate in position 2, 5 and 7. Glycine was exclusively chosen at position 1. Library B showed similar preferences for acidic residues, comparable to library A.

Randomly picked sequences from library A after 6 rounds of selection.

Shaded positions were partially or fully randomized; others were fixed.

Positions with a dash contained DNA sequence that was not clearly identifiable.

Library A: X X X X X X X K N L T R
                           N
                           S position in linker library A: 1 2 3 4 5 6 7 8

| | | | | | | | | | | | | SEQ ID NO |
|---|---|---|---|---|---|---|---|---|---|---|---|---|
| G | S | V | F | A | E | M | S | N | L | T | R | 52 |
| G | D | D | T | R | G | S | N | N | L | T | R | 53 |
| G | T | D | V | S | S | D | S | N | L | T | R | 54 |
| G | D | V | S | D | R | M | S | N | L | T | R | 55 |
| G | L | V | P | S | A | A | S | N | L | T | R | 56 |
| E | G | G | E | E | S | F | K | N | L | T | R | 57 |
| G | Y | Y | T | D | R | L | S | N | L | T | R | 58 |
| G | V | D | P | V | S | T | S | N | L | T | R | 59 |
| G | L | P | G | - | - | V | R | N | L | T | V | 60 |
| V | V | G | Q | D | G | E | N | N | L | T | R | 61 |
| G | E | P | L | S | F | E | S | N | L | T | R | 62 |
| G | W | G | V | A | V | E | N | N | L | T | R | 63 |
| G | F | L | V | E | D | E | S | N | L | T | R | 64 |
| G | F | G | D | S | Y | W | S | N | L | T | R | 65 |
| G | D | M | L | L | P | E | S | N | L | T | R | 66 |
| G | A | V | S | E | G | S | S | N | L | T | R | 67 |
| S | S | S | L | S | D | G | S | N | L | T | R | 68 |
| G | E | W | D | E | M | D | S | N | L | T | R | 69 |
| G | F | L | T | E | L | D | K | N | L | T | R | 70 |
| G | M | L | G | G | E | M | S | N | L | T | R | 71 |
| G | G | G | D | E | V | N | N | L | T | R | I | 72 |
| W | Y | P | M | Y | G | G | S | N | L | T | R | 73 |
| G | G | P | R | E | N | G | S | N | L | T | R | 74 |
| G | Q | F | M | E | G | V | S | N | L | T | R | 75 |
| G | G | A | V | E | G | E | N | N | L | T | R | 76 |
| G | G | V | D | V | G | G | N | N | L | T | R | 77 |
| G | A | E | G | G | - | E | N | N | L | T | R | 78 |
| G | V | Q | Q | E | S | V | N | N | L | T | R | 79 |
| G | M | A | P | M | G | D | S | N | L | T | R | 80 |
| G | L | V | G | S | E | V | S | N | L | T | R | 81 |
| S | E | A | I | L | N | W | S | N | L | T | - | 82 |
| G | W | G | V | G | A | G | S | N | L | T | R | 83 |
| G | Y | G | E | V | L | E | S | N | L | T | R | 84 |
| D | V | V | W | A | E | S | S | N | L | T | R | 85 |
| G | K | S | V | D | M | E | N | N | L | T | R | 86 |
| G | E | G | E | G | I | A | N | N | L | T | R | 87 |
| G | V | E | V | P | G | S | S | N | L | T | R | 88 |
| G | M | D | G | A | S | E | N | N | L | T | R | 89 |
| G | S | L | G | D | P | I | S | N | L | T | R | 90 |
| G | P | L | D | E | T | M | K | N | L | T | R | 91 |
| T | L | S | G | E | G | E | K | N | L | T | R | 92 |
| G | E | D | M | G | S | P | S | N | L | T | R | 93 |
| D | V | G | D | E | K | E | S | N | L | T | R | 94 |
| G | L | T | N | T | G | L | S | N | L | T | R | 95 |

```
D A Y N E A P S|N L T R    96
G A V D V W D S|N L T R    97
G L S V D S G S|N L T R    98
E W E G Q S V S|N L T R    99
G A A G M E G S|N L T R   100
G V D E W E S S|N L T R   101
G G V - Q E G S|N L T -   102
G E W E G L E S|N L T R   103
G W E G P E E S|N L T R   104
G S M M D D A S|N L T R   105
G E G L E V S S|N L T R   106

G S D D S R G S|N L T R   107
G M E P V A E N|N L T R   108
Y S E G M G G S|N L T R   109
G E - P H C M N|N L T R   110
G N V D W Q P S|N L T R   111
G E E V T E E N|N L T R   112
D L G G V E P R|N L T R   113
G A V N L G D S|N L T R   114
G V T G D T D S|N L T R   115
```

Randomly picked sequences from library D after 6 rounds of selection

Shaded positions were fully randomized; others were fixed.

Positions with a dash contained DNA sequence that was not clearly identifiable.

```
positions in linker    8  9 10 11 12 13 14    SEQ ID
library D                                     NO.
              S G|L R V S D L A|G G   116
              S G|F S R R G P S|G G   117
              S G|S A G W V S V|- R   118
              S G|P H G S V R L|G G   119
              S G|L L E V R D L|G G   120
              S G|L S S V G L L|G G   121
              S G|L L R G L V E|G G   122
              S G|A V V W R Q L|G G   123
              S G|V A A R L K V|G G   124
              S G|V Y R Q F G S|G G   125
              S G|G T E R S V V|G G   126
              S G|L A R G T V G|G G   127
              S -|S V R D V W D|G -   128

S G|S M V W R W S|G G   129
              S G|D V P N A Y R|G G   130
              S G|R L I S R G E|G G   131
              S G|F L E L K S W|G G   132
              S G|- - - - F - |G G   133
              S G|S V K A W S P|G G   134
              S G|D G L V W L R|G G   135
              S G|W G L R S S V|G G   136
              S G|D S S R N W A|G G   137
              S G|S R G L E F W|G G   138
              S G|F R M V E V G|G -   139
              S G|M W D R V M D|G G   140
              S G|F E R M P M G|G G   141
              S G|G D S T R G Y|G G   142
              S G|E V M W K A L|G G   143

S G|F Q D L R G L|G G   144
              S G|M L L G D R R|G G   145
              S G|P D W G R V V|G R   146
              S G|Q E L M F E R|G G   147
              S G|L R V V E Q R|G G   148
              S G|V E N Y L S R|G G   149
              S G|S V R A K E M|G G   150
              S G|T R - - - - T|G G   151
              S G|A R E W R V M|G G   152
              S G|L S L R G L G|G G   153
              S G|W W K S S L A|G G   154
              S G|A E R G R S V|G G   155
              S G|V G R X N R S|G G   156
              S G|K G V G V G R|G G   157
              S G|S S S R S S L|G G   158
```

```
              S G|S R A W L R G|G G   159
              S G|L F K V D F V|G G   160
              S G|L G S F M V R|G G   161
              S G|A S A G L L R|G G   162
              S G|S W W T G L Y|G -   163
              S G|V E R S V V A|G G   164
              S G|L G F G R M W|G G   165
              S G|K A S L L R Y|G G   166
              S G|L G V R S V L|G G   167
              S G|R S L G V A Y|G G   168
              S G|D G L Q K L|G G   169
              S G|E N L L R V S|G G   170
              S G|G R M S S P V|G G   171
              S G|S I G R V L M|G G   172
              S G|S S G R M R P|G G   173

S G|M R S L P S E|G G   174
              S G|R M S W L K L|G G   175
              S G|W A L S R W W|G G   176
              S G|L I K W G S S|G G   177
              S G|S S E Q R L L|G G   178
              S G|R S L L R S S|G G   179
              S G|G V E S V R L|G G   180
              S G|A F G W V G A|G G   181
              S G|P Q E L R L G|G G   182
              S G|L V G E L R G|G G   183
              S G|M R S L E R F|G G   184
              S G|R N V T L G L|G G   185
              S G|S N M W R W W|G G   186
              S G|G K S L W D Y|G G   187
              S G|L V F K S L S|G G   188

S G|G E G S Y S R|G A   189
              S G|S L G L P S A|G G   190
              S G|R L L M G L E|G G   191
              S G|H L E V R G P|G G   192
              S G|M R F L A E V|G G   193
              S G|M S R D A W A|G G   194
              S G|W G M R G W V|G G   195
              S G|V Q T L R S F|G G   196
              S G|W E T R G V S|G G   197
              S G|D H R L L M L|G G   198

S G|G R A L R G G|G G   199
              S G|I M R E W G I|G G   200
              S G|L V V L F S R|G G   201
              S G|- D W V D R G|G G   202
              S G|Y D V R V G T|G G   203
              S G|Q V R P L A R|G G   204
              S G|R V A S S R T|G G   205
              S G|L L R Y N S S|G G   206
              S G|V V T S R V L|G G   207
```

The results from library A and D were combined to create a complete consensus for residues 1 through 14 (GEGVEE-EXXEWRGX) (SEQ ID NO:208). A new library was designed based on these results and positions with limited preference, such as 2, 3, 4 and 6 were patially randomized, whereas positions with no significant preference, such as 8, 9, 14 and 15, were fully randomized again. This new substrate library was panned 6 rounds and 200 clones were picked randomly for sequence analysis. The statistical analysis lead to a consensus sequence (GEGVEEELWEWR) (SEQ ID NO:209) in the context of previously chosen and fixed residues.

Randomly picked sequences from the consensus library after 6 rounds of selection.

Shaded positions were partially or fully randomized; others were fixed.

Positions with a dash contained DNA sequence that was not clearly identifiable.

| position in linker | 1 | 2 | 3 | 4 | 5 | 6 | 7 | 8 | 9 | 10 | 11 | 12 | 13 | 14 | 15 | SEQ ID NO: |
|---|---|---|---|---|---|---|---|---|---|---|---|---|---|---|---|---|
| Consensus Library | G | E | V | G | E | E | E | X | X | E | W | R | G | X | X | G G | 210 |
|  |  |  | E | D | D | G |  |  |  |  |  |  |  |  |  |  | 211 |
|  |  |  | G | V |  |  |  |  |  |  |  |  |  |  |  |  | 212 |

| position in linker | 1 | 2 | 3 | 4 | 5 | 6 | 7 | 8 | 9 | 10 | 11 | 12 | 13 | 14 | 15 | SEQ ID |
|---|---|---|---|---|---|---|---|---|---|---|---|---|---|---|---|---|
|  | G | E | G | G | E | G | V | F | S | E | W | R | G | V | W | G G | 213 |
|  | G | D | E | V | E | G | E | W | S | E | W | R | G | L | R | G G | 214 |
|  | G | E | V | G | D | E | E | H | W | E | W | R | G | L | Q | G G | 215 |
|  | G | E | V | G | E | G | E | E | E | E | W | R | G | R | V | G G | 216 |
|  | G | E | V | G | E | G | E | I | L | E | W | R | - | S | D | P D | 217 |
|  | G | E | G | G | E | G | E | A | F | E | W | R | G | Y | R | G G | 218 |
|  | G | E | V | V | E | E | E | L | S | E | W | R | G | F | F | G G | 219 |
|  | G | E | V | G | D | E | E | I | Q | E | W | R | G | L | S | G G | 220 |
|  | G | E | G | D | G | E | Q | V | E | W | R | G | G | W | G G |  | 221 |
|  | G | E | G | - | - | G | V | F | L | E | W | R | G | - | - | G G | 222 |
|  | G | E | G | V | E | G | E | W | L | E | W | R | G | M | S | G G | 223 |
|  | G | E | G | D | E | G | E | L | L | E | W | R | G | G | F | G G | 224 |
|  | G | E | G | G | D | G | E | Y | W | E | W | R | G | G | R | G G | 225 |
|  | G | E | V | V | E | E | E | A | W | E | W | R | G | L | L | G G | 226 |
|  | G | E | V | V | D | E | E | V | N | E | W | R | G | F | A | G G | 227 |
|  | G | E | G | V | E | G | E | L | Y | E | W | R | G | I | L | G G | 228 |
|  | G | E | G | D | D | E | E | L | F | E | W | R | G | F | L | G V | 229 |
|  | G | E | V | V | E | G | E | T | F | E | W | R | G | L | T | G G | 230 |
|  | G | E | E | V | E | E | E | L | W | E | W | R | G | A | T | G G | 231 |
|  | G | E | E | V | D | G | E | L | - | E | W | R | G | G | L | G G | 232 |
|  | G | E | E | V | - | - | E | L | - | E | W | R | G | G | R | G G | 233 |
|  | G | E | E | G | D | E | D | V | P | E | W | R | G | F | G | G P | 234 |
|  | G | E | G | V | D | G | E | A | I | E | W | R | G | L | L | G G | 235 |
|  | G | E | G | E | G | E | V | T | E | W | R | G | M | L | G G |  | 236 |
|  | G | E | E | G | E | G | E | E | V | E | W | R | G | L | S | G G | 237 |
|  | G | E | V | V | D | G | E | G | M | E | W | R | G | L | A | G G | 238 |
|  | G | E | E | D | D | E | E | A | L | E | W | R | G | L | M | V G | 239 |
|  | G | E | E | V | D | G | E | I | A | E | W | R | G | L | R | G G | 240 |
|  | G | E | V | V | E | G | E | T | V | E | W | R | G | I | L | G G | 241 |
|  | G | E | V | G | E | G | E | M | A | E | W | R | G | F | R | G G | 242 |
|  | G | E | G | G | D | E | E | L | V | E | W | R | G | L | S | G G | 243 |
|  | G | E | V | G | E | G | E | L | S | E | W | R | S | I | W | G G | 244 |
|  | G | E | G | G | D | E | E | F | V | E | W | R | G | L | G | G G | 245 |
|  | G | E | E | G | E | G | E | V | R | E | W | R | G | R | S | G G | 246 |
|  | G | E | V | G | D | G | E | F | M | E | W | R | G | F | L | G G | 247 |
|  | G | E | V | V | E | G | E | T | F | E | W | R | G | L | T | G G | 248 |
|  | G | E | V | G | E | G | E | I | A | E | W | R | G | F | S | G G | 249 |
|  | G | E | E | D | D | E | E | A | L | E | W | R | G | L | M | V G | 239 |
|  | G | E | E | G | E | E | E | V | M | E | W | R | G | A | F | G G | 250 |
|  | G | E | G | D | D | G | E | I | T | E | W | R | G | F | M | G G | 251 |
|  | G | E | G | V | E | E | E | L | S | E | W | R | G | L | G | G G | 252 |
|  | G | E | V | G | E | G | E | I | A | E | W | R | G | F | S | G G | 249 |
|  | G | E | E | V | D | G | E | S | L | E | W | R | G | S | R | G G | 253 |
|  | G | E | G | G | A | E | E | V | I | E | W | R | G | G | F | G G | 254 |
|  | G | E | G | V | E | E | E | F | P | E | W | R | G | Y | W | G G | 255 |
|  | G | E | G | G | E | G | E | T | F | E | W | R | G | L | S | G G | 256 |
|  | G | E | V | G | D | G | E | S | F | E | W | R | G | G | V | G G | 257 |
|  | G | E | V | V | E | G | E | E | F | E | W | R | G | V | R | T P | 258 |
|  | G | E | V | V | D | E | E | S | L | E | W | R | G | L | R | G G | 259 |
|  | G | E | G | G | E | G | E | T | F | E | W | R | G | L | S | G G | 256 |
|  | G | E | E | G | D | E | E | L | V | E | W | R | G | H | V | G G | 260 |
|  | G | E | E | G | E | E | E | G | F | E | W | R | G | L | L | G G | 261 |
|  | G | E | V | V | D | E | E | S | L | E | W | R | G | L | R | G G | 259 |
|  | G | E | G | G | D | G | E | I | A | E | W | R | G | S | L | G G | 262 |
|  | G | E | V | V | E | E | E | L | S | E | W | R | G | F | F | G G | 219 |
|  | G | E | G | V | E | E | E | L | W | E | W | R | G | F | A | G G | 263 |
|  | G | E | G | V | E | E | E | V | S | E | W | R | Y | P | G | G - | 264 |
|  | G | E | V | D | E | G | E | L | L | E | W | R | G | G | L | G G | 265 |
|  | G | E | V | E | E | E | L | F | E | W | R | G | L | G | G - |  | 266 |
|  | G | E | V | V | D | G | E | G | M | E | W | R | G | L | A | G G | 238 |
|  | G | E | V | G | E | G | E | S | S | E | W | R | G | S | F | G G | 267 |
|  | G | E | V | E | E | E | L | S | E | W | R | G | Y | V | G G |  | 268 |
|  | G | E | E | G | D | E | E | S | L | E | W | R | G | F | E | G G | 269 |
|  | G | E | G | G | E | G | E | L | F | E | W | R | G | L | S | G G | 270 |
|  | G | E | G | D | E | D | V | P | E | W | R | G | F | G | G P |  | 234 |
|  | G | E | G | V | E | E | E | L | Q | E | W | R | G | V | W | G G | 271 |
|  | G | E | V | D | D | G | E | G | F | E | W | R | G | A | R | G G | 272 |
|  | G | E | E | G | E | E | E | V | M | E | W | R | G | A | F | G G | 250 |
|  | G | E | G | G | E | G | E | T | F | E | W | R | G | L | S | G G | 256 |
|  | G | E | G | V | E | G | E | P | V | E | W | R | G | L | L | G G | 273 |
|  | G | E | E | G | Q | E | E | R | S | E | W | R | G | G | G | G T | 274 |
|  | G | E | G | D | E | G | E | W | W | E | W | R | G | L | N | G R | 275 |
|  | G | E | V | V | E | G | E | V | L | E | W | R | G | F | I | G G | 276 |
|  | G | E | G | G | D | E | E | L | P | E | W | R | G | L | G | G G | 277 |
|  | G | E | G | V | E | E | E | M | L | E | W | R | G | Y | A | G G | 278 |

```
G E G V E G E S V E W R G F V G G 279
G E E V E E E L I E W R G F G G G 280
G E V D E E E L L E W R G R S G G 281
G E G G E G E A L E W R G V Y G G 282
G E V V E E E L W E W R G S R G G 283
G E V D G E A I E W R G G L G G 284
G E V V E E E A W E W R G L L G G 226
G E V V E E E V M E W R G G S G G 285
G E E V E G E S A E W R G L R G G 286
G E G V D G E R F E W R G L G - - 287
G E E G D G E I L E W R G F A G G 288
G D G G D E E V S E W R G F K G G 289
G E G V E E E L P E W R G F T G G 290
G E E G E E E L L E W R G F L G G 291
G E V G D G E L T A W R G L N G G 292

G E V G D G E L W E W R G L A G G 293
G E E V E G E S A E W R G L R G G 286
G E E G D G E L M E W R G F A G G 294
G E G G E E E L I E W R G G F G G 295
G E V V D G E D V E W R G L N G G 296
G E V V E G E L F E W R G L L G G 297
G E G D D E E L F E W R G F L G - 298
G E V G E E E L S E W R G F R G G 299
G E G G E G E L P E W R G F L G G 300
G E G G D E E L P E W R G L M G G 301
G E G G D G E M V E W R G P G G G 302
G - V G E G E S L E W R G F R G G 303
G E V G E G E L F E W R G L G G G 304
G E V V E G E P T E W R G V R G G 305
G E G V E E E V T E W R G A G G G 306

G E G G A E E V I E W R G G F G G 254
G E V V E E E S P E W R G V W S G 307
G E V V E E E A W E W R G L L G G 226
G E V V D G E L S E W R G F A G G 308
G E E V E E E L W E W R G F G G G 309
G E E D E G E S W E W R G N R G G 310
G E V V E G E L F E W R G L L G G 297
G E V V E E E V T E W R G A G G G 306
G E V G D E E L S E W R G G R G G 311
G E V V E E E A W E W R G L - G G 312
G E G V E G E L L E W R G L - G G 313
G E E V D E E Y F E W R G L L G G 314
G E E V E E E L W E W R G F G G G 309
G E V G D G E L W E W R G L A G G 293
G E V G E G E S N E W R G L F G G 315

G E G V E E E L V E W R G L G G G 316
G E G G E G E T F E W R G P L G G 317
G E E G D G E V F E W R G L M G G 318
G E G G E E E W F E W R G I W G G 319
G E E G E E E L W E W R G G L G G 320
G E V V E G E P T E W R G V R G G 305
G E - - D - E L - E W R G L S G G 321
G E V E E E L W E W R G F A G G 263
G E G V D E E L I E W R G L R G G 322
G E V G E E E L S E W R G F R G G 299
G E V G D G E S A E W R G L S G G 323
G E G G E G E F W E W R G L P G G 324
G E G V E E E L W E W R G F A G G 263
G E E G E G E A L E W R G F R G G 325
G E V V D G E V P E W R G F S G G 326

G E G V D G E S F E W R G G V G G 257
G E V G E E E R A E W R G L R G G 327
G E G V E G E L S E W R G V R G G 328
G E G V - G E - - E W R G - - G G 329
G E V V D G E R F E W R G L L G G 330
G E - G D G E V F E W R G L M G G 331
G E E G E E E L W E W R G G L G G 320
G E G D E E E F P E W R G L L G G 332
G E V G E G E I L E W R G L - - - 333
G E V G D G E S L E W R G G L G G 334

G E G V E E E L W E W R G F A G G 263
G - V G E G E S L E W R G F R G G 303
G E G V D G E T R E W R G G F G G 335
G E V V E G E W L E W R G L L G G 336
G E V V D G E L A E W R G L A G G 337
G E E V E G E I A E W R G L P G G 338
G E G V E G E Y T E W R G K S G G 339
G E V V E G E G P E W R G L W G G 340
G E V G D G E V W E W R G V G G G 341
G E V G D G E F M E W R G L R G G 342
```

Extracted sequences from above containing the LW sequence at 26 positions 8 and 9

| position in linker | 1 | 2 | 3 | 4 | 5 | 6 | 7 | 8 | 9 | 10 | 11 | 12 | 13 | 14 | 15 | | |
|---|---|---|---|---|---|---|---|---|---|---|---|---|---|---|---|---|---|
| | G | E | G | V | E | E | E | L | W | E | W | R | G | F | A | G G | 263 |
| | G | E | E | V | E | E | E | L | W | E | W | R | G | A | T | G G | 343 |
| | G | E | G | V | E | E | E | L | W | E | W | R | G | F | A | G G | 263 |
| | G | E | V | V | E | E | E | L | W | E | W | R | G | S | R | G G | 283 |
| | G | E | V | G | D | G | E | L | W | E | W | R | G | L | A | G G | 293 |
| | G | E | E | V | E | E | E | L | W | E | W | R | G | F | G | G G | 309 |
| | G | E | E | V | E | E | E | L | W | E | W | R | G | F | G | G G | 309 |
| | G | E | V | G | D | G | E | L | W | E | W | R | G | L | A | G G | 293 |
| | G | E | E | G | E | E | E | L | W | E | W | R | G | G | L | G G | 320 |
| | G | E | G | V | E | E | E | L | W | E | W | R | G | F | A | G G | 270 |
| | G | E | G | V | E | E | E | L | W | E | W | R | G | F | A | G G | 270 |
| | G | E | E | G | E | E | E | L | W | E | W | R | G | G | L | G G | 320 |
| | G | E | G | V | E | E | E | L | W | E | W | R | G | F | A | G G | 270 |

Consensus Library—Statistical Analysis

| position in linker | 1 | 2 | 3 | 4 | 5 | 6 | 7 | 8 | 9 | 10 | 11 | 12 | 13 | 14 | 15 | SEQ ID NO: |
|---|---|---|---|---|---|---|---|---|---|---|---|---|---|---|---|---|
| Consensus Library | G | E | V | G | E | E | E | X | X | E | W | R | G | X | X | 344 |
| | | | E | D | D | G | | | | | | | | | | 345 |
| | | | G | V | | | | | | | | | | | | 355 |

Positions 3 through 6 contained tailored (partially randomized) codon usage, allowing only the depicted residues. Only one codon per residue was used. There was no clear preference at these positions for a specific residue. However, Asp at position 4 was less frequently observed than Gly or Val.

Frequency of finding a given residue

| Residue/Position | G | E | D | V |
|---|---|---|---|---|
| 3 | 40.9% | 22.7% | | 35% |
| 4 | 44% | | 5.8% | 49% |
| 5 | | 60% | | 35% |
| 6 | 55.8% | 42% | | |

Consensus Library—Statistical Analysis

| position in linker | 1 | 2 | 3 | 4 | 5 | 6 | 7 | 8 | 9 | 10 | 11 | 12 | 13 | 14 | 15 | SEQ ID NO: |
|---|---|---|---|---|---|---|---|---|---|---|---|---|---|---|---|---|
| Consensus Library | G | E | V | G | E | E | E | X | X | E | W | R | G | X | X | 344 |
| | | | E | D | D | G | | | | | | | | | | 345 |
| | | | G | V | | | | | | | | | | | | 355 |

Positions 8 and 9 were completely randomized. To determine the probability of each residue at positions 8 and 9, the frequency of each residue was normalized by the codon bias. The preference of a given residue at a position is related to the sigma value. The relative significance of any given residue is related to the number of standard deviation units (sigma) above a random chance occurrence of a given residue in the library assuming a binomial distribution of amino acids (see Lowman and Wells, J. Mol. Biol. (1993) 234: 564–578). At position 8, there was a high preference for Leu; Ile, Val, and Phe were also preferred. At position 9, Trp and Phe were highly preferred; Ile, Leu, Pro, and Val were also preferred. Thus positions 8 and 9 had preferences for hydrophobic amino acids.

Example III

Production of Z-A-183-Extension Variants

An expression plasmid for Z-A-183 was constructed using Kunkel mutagenesis (Kunkel, T. A, et al., (1987) Methods Enzymol., 154: 367–382) by inserting a DNA sequence encoding a linker with an enterokinase recognition site (GGSGGDDDDK) (SEQ ID NO:346) and A-183 with a stop codon (EEWEVLCWTWETCERstop) (SEQ ID NO:16) into the vector pZCT after the C-terminus of the Z consensus domain from protein A (Starovasnik, M. A., et al., (1999)Protein Sci., 8: 1423–1431). The resulting plasmid pZCT-A-183 was confirmed by DNA sequencing and used as expression vector as well as a template for Kunkel mutagenesis. The extension variants pZCT-A-183X, pZCT-A-183(GGS)$_3$GGR, pZCT-A-183(GGS)$_4$, pZCT-A-183EWA, pZCT-A-183EW were constructed by Kunkel mutagenesis (Kunkel, T. A, et al., (1987) Methods Enzymol., 154: 367–382) using pZCT-A183 as template by inserting DNA sequence encoding (GEGVEEELWEWR) (SEQ ID NO:209), (GGSGGSGGSGGR) (SEQ ID NO:347), (GGSGGSGGSGGS) (SEQ ID NO:348), (GEGVEEELWEWA) (SEQ ID NO:349), (GEGVEEELWEW) (SEQ ID NO:350), respectively, between the C-terminus of A-183 and the stop codon. All constructs were transformed into E.coli strain 27C7 and grown in low phosphate minimal media as previously described (Dennis, M. S., et al., (2001) Biochemistry, 40: 9513–9521). All Z-fusion peptides were secreted into and harvested from the media and initially purified using IgG-Sepharose (Amersham Pharmacia Biotech, Piscataway, N.J.) as described previously (Dennis, M. S., et al. (1993). Proteins: Struct., Funct., Genet., 15: 312–321). In order to obtain greater purity Z-fusion peptides were further purified by size exclusion on Superdex 75 (Amersham Pharmacia Biotech, Piscataway, N.J.) at 0.5 ml/min flow rate using Tris buffer pH 7.5 and 200 mM NaCl.

Fractions from gel filtration containing monomeric Z-fusion peptides were loaded on a Resource Q (1 ml) column (Amersham Pharmacia Biotech, Piscataway, N.J.) for concentration and final purification by ion exchange chromatography, using a salt gradient from 0.2 M to 0.8 M NaCl over 12 column volumes at 3 ml/min flow rate.

Z-A-183 showed an IC50 of 660 pM. Thus, in addition to the complete inhibition of FX activation, the A-183 C-terminal extension of provided a 55-fold improvement in the affinity for TF-FVIIa.

To address the question whether the extension has to be specific to obtain complete inhibition of FX activation, a

| Peptide | Sequence | SEQ ID NO: |
|---|---|---|
| A-183 | EEWEVLCWTWETCER | 16 |
| Z-A-183 | Z-GGSGGDDDDK-EEWEVLCWTWETCER | 346 and 16 |
| Z-A-183X | Z-GGSGGDDDDK-EEWEVLCWTWETCERGEGVEEELWEWR | 346, 16, 209 |
| Z-A-183 (GGS)₃GGR | Z-GGSGGDDDDK-EEWEVLCWTWETCERGGSGGGSGGSGGR | 346, 16, 347 |
| Z-A-183 (GGS)₄ | Z-GGSGGDDDDK-EEWEVLCWTWETCERGGSGGGSGGSGGS | 346, 16 348 |
| Z-A-183X-EWA | Z-GGSGGDDDDK-EEWEVLCWTWETCERGEGVEEELWEWA | 346, 16 349 |
| Z-A-183X-EW | Z-GGSGGDDDDK-EEWEVLCWTWETCERGEGVEEELWEW | 346, 16, 350 |

Z—Z domain of protein A
GGSGGDDDDK—enterokinase cleavage linker 346

Example IV

Amidolytic Activity of Immobilized FVIIa

Maxi-Sorp plates were separately coated with different concentrations of FVIIa (1, 5, 10 and 20 µg/ml) in 50 mM carbonate buffer pH 9.6 at 4° C. overnight. Amidolytic acivity was monitored at 405 nm over 5 min with 1 mM Chromozym t-PA at pH 6.0 and pH 8.5 in the absence and presence of 5-fold excess of sTF over FVIIa.

Inhibition of FX Activation and Amidolytic Activity

Inhibition of FX activation by TF-VIIa was determined with 300 pM relipidated $TF_{1-243}$, 20 pM FVIIa, and 165 nM FX at 25° C. as a function of peptide concentration essentially as described (Dennis, M. S., et al., (2000) Nature, 404: 465–470; Kelley, R. F., et al., (1997) Blood, 89: 3219–3227). TF was incorporated into phospholipid vesicles and quantified as previously described (Kelley, R. F., et al., (1997) Blood, 89: 3219–3227). The linear rates of FXa generation can be expressed as mOD405/min/min or as fractional activities ($v_i/v_0$). Control experiments showed that the peptides tested did not inhibit the FXa chromogenic activity.

Inhibition of amidolytic activity of TF-FVIIa was monitored as a function of peptide concentration, as described previously (Dennis, M. S., et al., (2000) Nature, 404: 465–470) using Chromozym t-PA as amidolytic substrate. The linear rates of the increase in absorbance at 405 nm can be expressed as $mOD_{405}$/min or as fractional activities (vi/v0).

Figure 7:
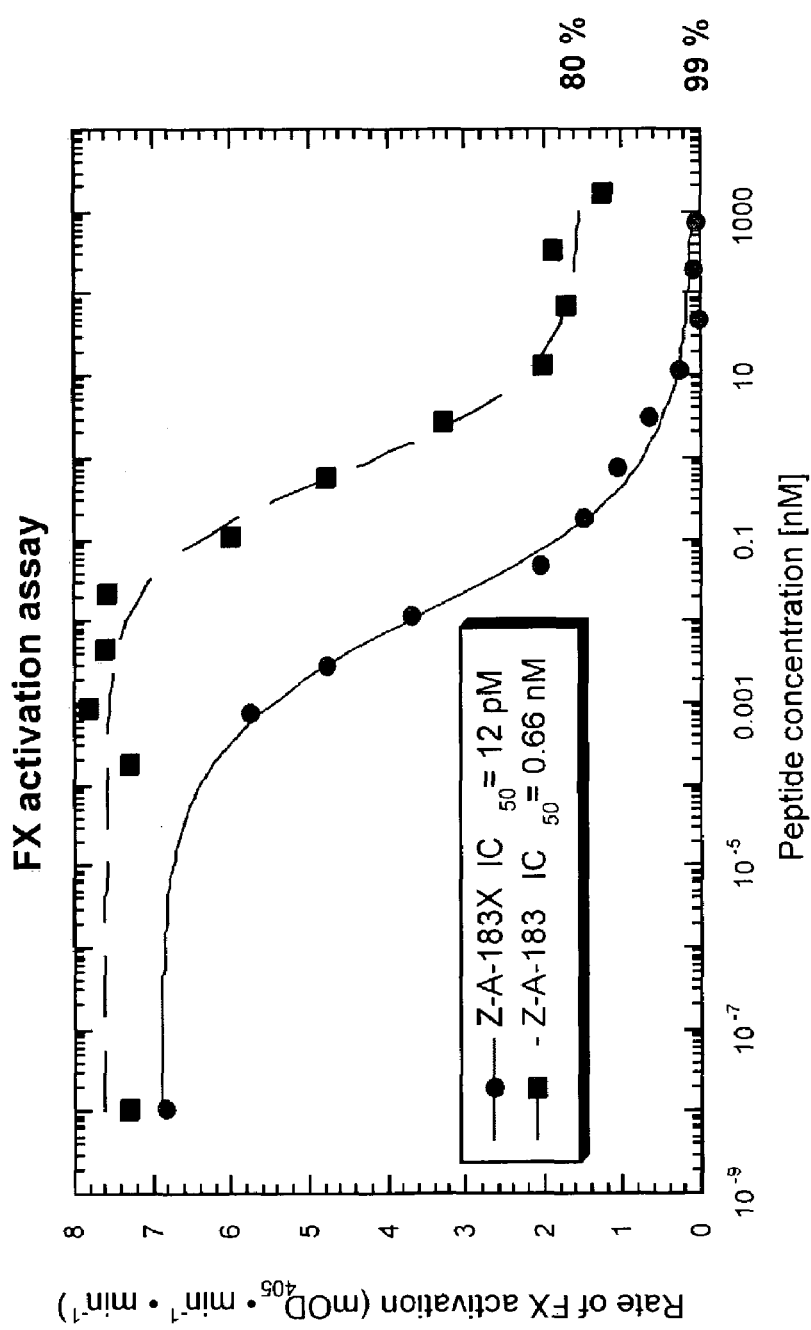
FIG. 7. Inhibition of TF-FVIIa catalyzed activation of FX. The inhibition of FX activation by Z-A-183X and Z-A-183 is shown. Z-A-183X exhibited complete inhibition (ca. 99%) of FX activation and an improvement in potency (IC50=12 pM) relative to Z-A-183, which inhibited the activity to 80% extent with an IC50 of 660 pM.
Figure 8:
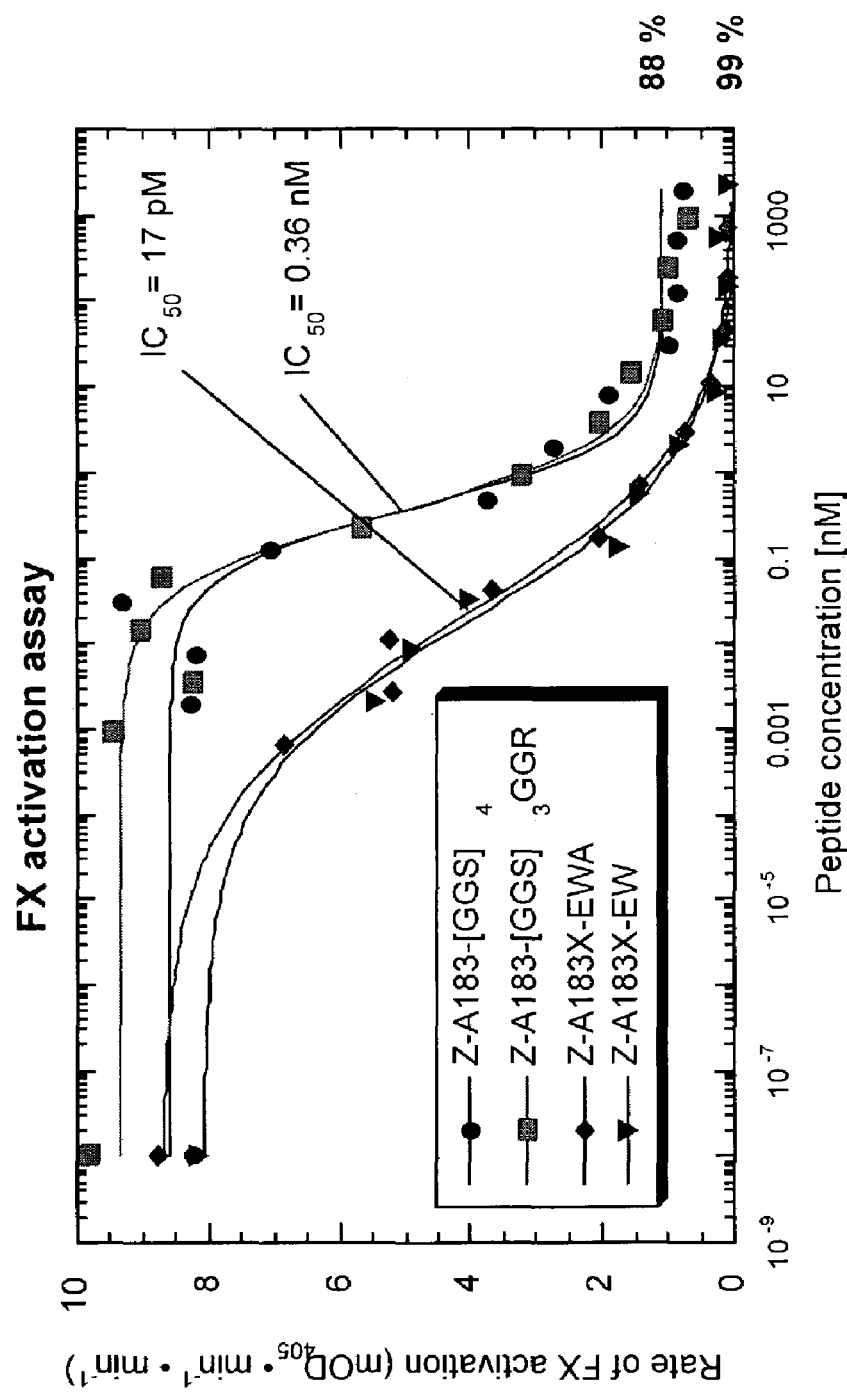
FIG. 8. Inhibition of FX activation with different extensions. The inhibition of FX activation by Z-A-183-[GGS]$_4$, Z-A-183-[GGS]$_3$GGR, Z-A-183X-EW, Z-A-183X-EWA is shown. A random extension showed a greater extent of inhibition of LX activation (88%) compared to Z-A-183 (FIG. 7) or A-183 as observed previously (Dennis, M. S., et al., (2001) Biochemistry, 40:9513–9521), however the inhibition was still not complete. The C-terminal arginine is not required to obtain complete inhibition.

Z-A-183-GEGVEEELWEWR (SEQ ID NO:209) (Z-A-183X) and Z-A-183 were tested for their ability to inhibit the TF-FVIIa catalyzed activation of FX (FIG. 7 and FIG. 8). Z-A-183X inhibited 99% of the activity upon saturation. This is in contrast to the 80% inhibition of activity observed for Z-A-183. Furthermore, the IC50 value in the FX activation assay for Z-A-183X improved to 12 pM, whereas random extension consisting of a GGS-motif with and without arginine at the carboxy-terminus (Z-A-183 [GGS]₃GGR and Z-A-183 [GGS]₄, respectively) was tested. An Arg to Ala mutant Z-A-183-GEGVEEELWEWA (SEQ ID NO:349) (Z-A-183 EW) and an Arg truncation Z-A-183-GEGVEEELWEW (SEQ ID NO:350) (Z-A-183 EW) in the selected extension to determine its importance for blocking the active site and extent of inhibition were also tested. It has been previously shown, that Z-domain C-terminally fused to A-183 increases the extent of inhibition in FX activation. Consistent with these findings, the random extensions do improve the extent of inhibition of FX activation, but only up to 88%, which is independent of the arginine. Interestingly, the specific extension does not depend on the C-terminal arginine as well. Both truncation of the arginine (Z-A-183 EW) or mutation to alanine (Z-A-183 EW) resulted in complete inhibition of FX activation. (FIG. 8)

Example V

Clotting Assay

Figure 9:
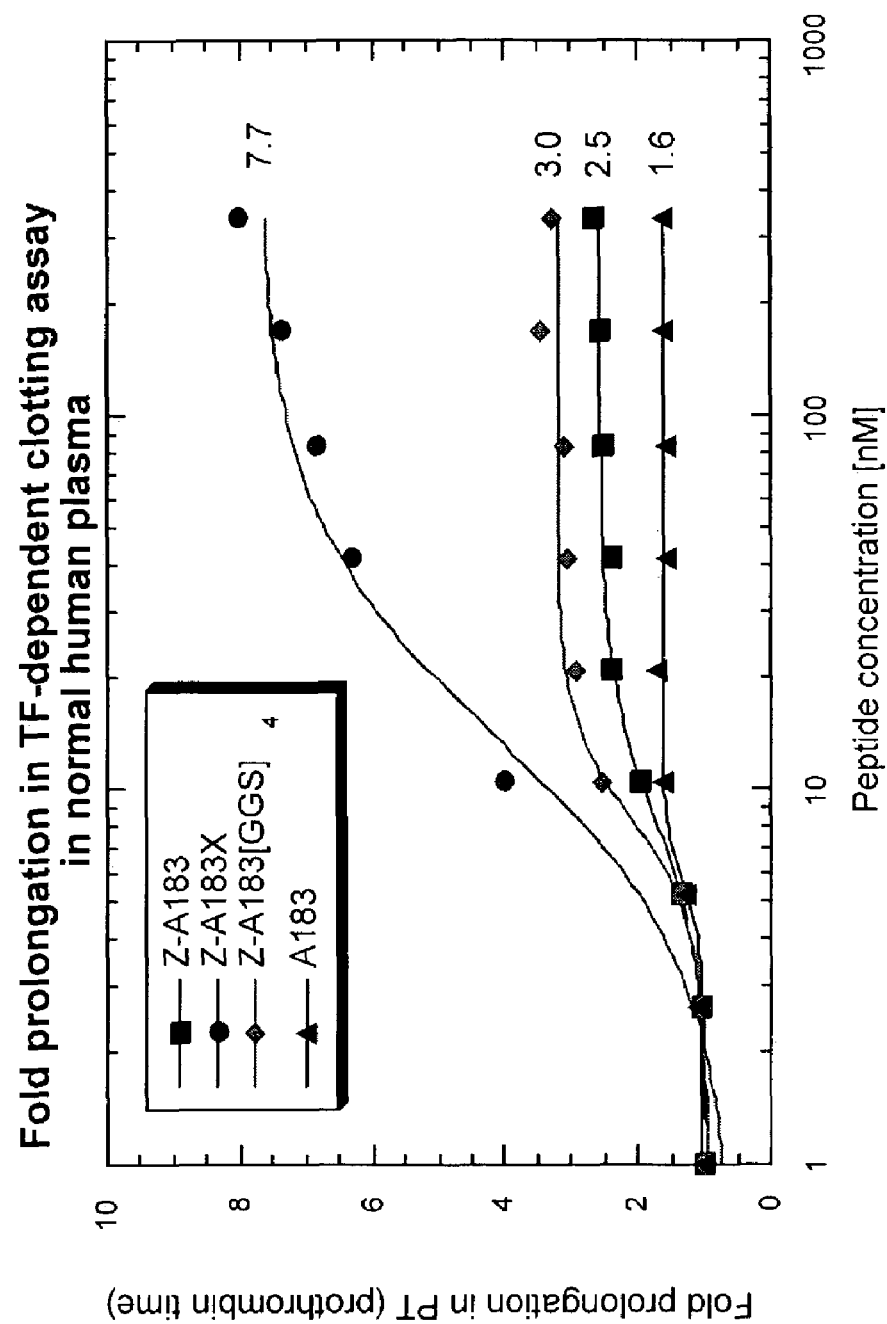
FIG. 9. Prolongation of TE-dependent clotting times. The fold prolongation of the clotting time upon initiation by TF and Ca2+ in the PT assay is shown for Z-A-183, Z-A-183X, Z-A-183-[GGS]$_4$, and A-183. Compared to A-183 (1.6-fold) and the two control peptides, Z-A-183X showed a significant improvement (7.7-fold) in the fold prolongation of clotting.
Figure 11A:
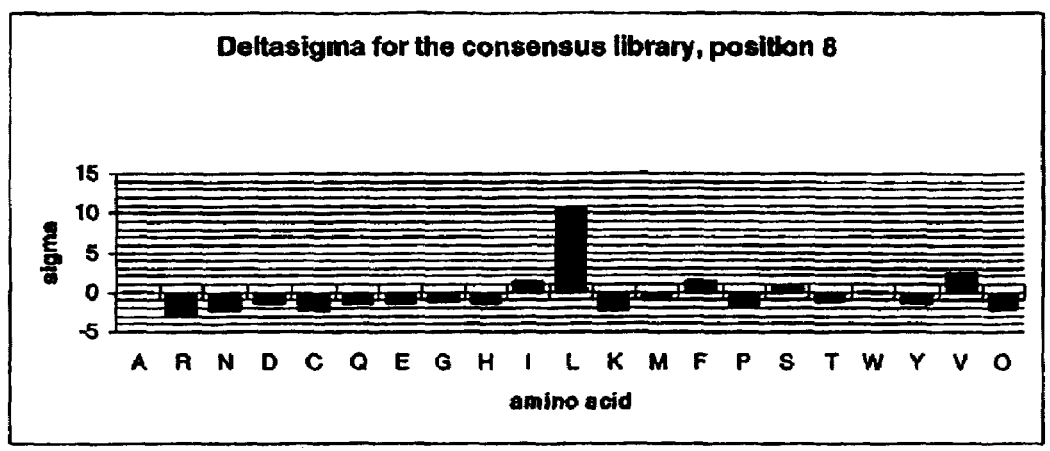
FIGS. 11A & B show the delta sigma values for amino acids at position 8(A) and position 9(B). The preference of a given residue at a position is related to the delta sigma value.
Figure 11B:
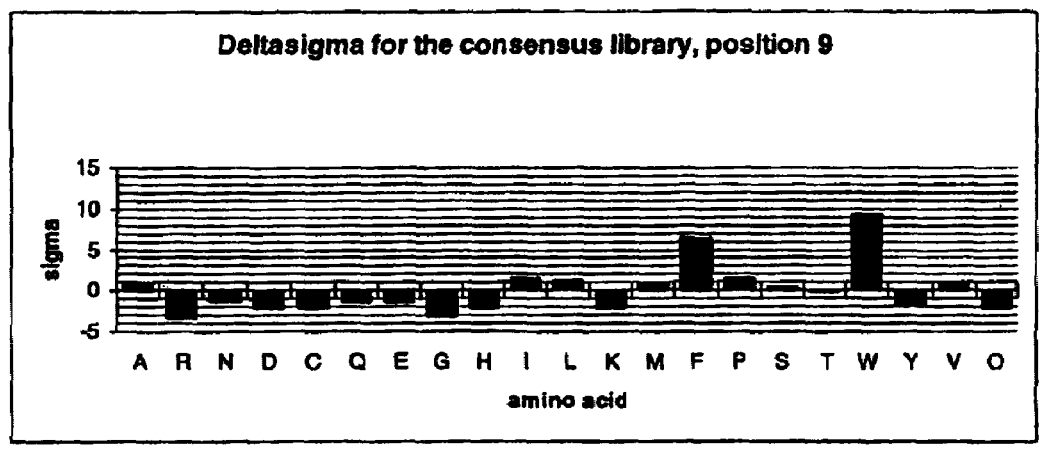

The prothrombin time (PT) assay was performed in citrated pooled normal human plasma as described previously (Dennis, M. S., et al., (2000) Nature, 404: 465–470). Clotting times were determined using an ACL 300 Coagulation Analyzer (Coulter Corp., Miami, Fla.) using Innovin (human relipidated TF and Ca2+) from Dade International Inc. to initiate the assay. The fold prolongation of the clotting time upon initiation by TF and Ca2+ in the PT assay is shown for Z-A-183, Z-A-183X, Z-A-183-[GGS]₄, and A-183. Compared to A-183 (1.6-fold) and the two control peptides, Z-A-183X showed a significant improvement (7.7-fold) in the fold prolongation of clotting. (FIG. 9)

What is claimed is:

1. An isolated peptide which comprises the sequence:

GEGVEEELWEWR (SEQ ID NO:209),
   GEEVEEELWEWR (SEQ ID NO:351),
   GEVVEEELWEWR (SEQ ID NO:352),
   GEVGDGELWEWR (SEQ ID NO:353), or
   GEEGEEELWEWR (SEQ ID NO:354).

2. The isolated peptide of claim 1 which further comprises:
   i) the amino acid sequence $Glu_1$-$Glu_2$-$Trp_1$-$Glu_3$-Val-Leu-$Cys_1$-$Trp_2$-$Thr_1$-$Trp_3$-$Glu_4$-$Thr_2$-$Cys_2$-$Glu_5$-Arg (SEQ ID NO:16), or
   ii) an amino acid sequence that competes with SEQ ID NO:16 for binding FVII/FVIIa in an in vitro assay and having between 1 and 8 amino acids of SEQ ID NO:16 substituted according to the following:
   $Glu_1$ and $Glu_2$ are optionally absent or any amino acid;
   $Trp_1$ is an amino acid selected from the group consisting of Trp, Phe and Leu;
   $Glu_3$ is any amino acid;
   Val is an amino acid selected from the group consisting of Val and Ile;
   Leu is an amino acid selected from the group consisting of Leu, Ile, Met, Val and Ala;
   $Trp_2$ is amino acid selected from the group consisting of Trp, Phe, Tyr, Leu and Met;
   $Thr_1$ is any amino acid;
   $Trp_3$ is an amino acid selected from the group consisting of Trp, Phe and Tyr;
   $Glu_4$ is any amino acid;
   $Thr_2$ is any amino acid;
   $Glu_5$ is any amino acid;
   Arg is an amino acid selected from the group consisting of Arg, Lys, Leu and Trp.

3. A method of inhibiting FVIIa activity comprising the step of contacting FVIIa with the isolated peptide of claim 2 in the presence of tissue factor and under conditions which allow binding of the compound to FVIIa to occur.

4. A pharmaceutical composition comprising the peptide of claim 2 and a pharmaceutically acceptable carrier.

5. The isolated peptide of claim 1 comprising the sequence of GEGVEEELWEWR (SEQ ID NO:209).

6. The isolated peptide of claim 1 comprising the sequence of GEEVEEELWEWR (SEQ ID NO:351).

7. The isolated peptide of claim 1 comprising the sequence of GEVVEEELWEWR (SEQ ID NO:352).

8. The isolated peptide of claim 1 comprising the sequence of GEVGDGELWEWR (SEQ ID NO:353).

9. The isolated peptide of claim 1 comprising the sequence of GEEGEEELWEWR (SEQ ID NO:354).

10. The isolated peptide of claim 2 comprising the sequence of GEGVEEELWEWR (SEQ ID NO:209).

11. The isolated peptide of claim 2 comprising the sequence of GEEVEEELWEWR (SEQ ID NO:351).

12. The isolated peptide of claim 2 comprising the sequence of GEVVEEELWEWR (SEQ ID NO:352).

13. The isolated peptide of claim 2 comprising the sequence of GEVGDGELWEWR (SEQ ID NO:353).

14. The isolated peptide of claim 2 comprising the sequence of GEEGEEELWEWR (SEQ ID NO:354).

15. The isolated peptide of claim 2 comprising the amino acid sequence of EEWEVLCWTWETCERGEGVEEELWEWR (SEQ ID NO:356).

16. The isolated peptide of claim 2 comprising the amino acid sequence of EEWEVLCWTWETCER (SEQ ID NO:16).

17. The isolated peptide of claim 2 comprising the amino acid sequence of EEWEVLCWTWETCERGEGVEEELWEW (SEQ ID NO:357).

18. The isolated peptide of claim 2 comprising the amino acid sequence of EEWEVLCWTWETCERGEGVEEELWEW (SEQ ID NO:358).

19. The method of claim 3, wherein the peptide of claim 2 comprises the sequence of GEGVEEELWEWR (SEQ ID NO:209).

20. The method of claim 3, wherein the peptide of claim 2 comprises the sequence of GEEVEEELWEWR (SEQ ID NO:351).

21. The method of claim 3, wherein the peptide of claim 2 comprises the sequence of GEVVEEELWEWR (SEQ ID NO:352).

22. The method of claim 3, wherein the peptide of claim 2 comprises the sequence of GEVGDGELWEWR (SEQ ID NO:353).

23. The method of claim 3, wherein the peptide of claim 2 comprises the sequence of GEEGEEELWEWR (SEQ ID NO:354).

24. The method of claim 3, wherein the peptide of claim 2 comprises the amino acid sequence of EEWEVLCWTWETCERGEGVEEELWEWR (SEQ ID NO:356).

25. The method of claim 3, wherein the peptide of claim 2 comprises the amino acid sequence of EEWEVLCWTWETCER (SEQ ID NO:16).

26. The method of claim 3, wherein the peptide of claim 2 comprises the amino acid sequence of EEWEVLCWTWETCERGEGVEEELWEWA (SEQ ID NO:357).

27. The method of claim 3, wherein the peptide of claim 2 comprises the amino acid sequence of EEWEVLCWTWETCERGEGVEEELWEW (SEQ ID NO:358).

* * * * *